United States Patent
Noble et al.

(10) Patent No.: US 7,494,999 B2
(45) Date of Patent: *Feb. 24, 2009

(54) SULFONYL-SUBSTITUTED BICYCLIC COMPOUNDS AS MODULATORS OF PPAR

(75) Inventors: Stewart A. Noble, San Diego, CA (US); Guy Oshiro, San Diego, CA (US); James W. Malecha, San Diego, CA (US); Cunxiang Zhao, San Diego, CA (US); Carmen Robinson, San Diego, CA (US); Sergio G. Duron, San Diego, CA (US); Michael Sertic, Del Mar, CA (US); Andrew K. Lindstrom, Encinitas, CA (US); Andrew K. Shiau, San Diego, CA (US); Christopher D. Bayne, Honolulu, HI (US); Mehmet Kahraman, San Diego, CA (US); Boliang Lou, Louisville, KY (US); Steven P. Govek, San Diego, CA (US)

(73) Assignee: Kalypsys, Inc, San Diego, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 11/258,463

(22) Filed: Oct. 25, 2005

(65) Prior Publication Data
US 2006/0167012 A1   Jul. 27, 2006

Related U.S. Application Data

(60) Provisional application No. 60/679,813, filed on May 11, 2005, provisional application No. 60/623,252, filed on Oct. 29, 2004.

(51) Int. Cl.
A61K 31/4965 (2006.01)
C07D 241/04 (2006.01)
(52) U.S. Cl. .................. 514/255.02; 514/255.03; 544/383; 544/392; 544/403
(58) Field of Classification Search ........... 514/255.02, 514/255.03; 544/383, 392, 399
See application file for complete search history.

(56) References Cited

U.S. PATENT DOCUMENTS

| | | | |
|---|---|---|---|
| 5,464,788 A | 11/1995 | Bock et al. | |
| 5,756,504 A | 5/1998 | Bock et al. | |
| 6,465,468 B1 | 10/2002 | Baxter et al. | |
| 6,673,799 B1 | 1/2004 | Taniguchi et al. | |
| 6,852,718 B2 | 2/2005 | Burkamp et al. | |
| 6,939,875 B2 | 9/2005 | Auerbach et al. | |
| 7,157,452 B2 * | 1/2007 | Li et al. | 514/232.8 |
| 2004/0180925 A1 | 9/2004 | Matsuno et al. | |
| 2004/0224957 A1 | 11/2004 | Sharma et al. | |
| 2005/0070532 A1 | 3/2005 | Liu et al. | |
| 2005/0107445 A1 | 5/2005 | Watkins et al. | |
| 2005/0124625 A1 | 6/2005 | Salvati et al. | |
| 2005/0153981 A1 | 7/2005 | Li et al. | |
| 2005/0203151 A1 | 9/2005 | Malecha et al. | |
| 2005/0234046 A1 | 10/2005 | Zhao et al. | |
| 2006/0199820 A1 | 9/2006 | Bannen et al. | |
| 2006/0205736 A1 * | 9/2006 | Noble et al. | 514/255.02 |
| 2007/0093504 A1 * | 4/2007 | Bennett et al. | 514/255.03 |

FOREIGN PATENT DOCUMENTS

| | | |
|---|---|---|
| EP | 0548798 | 6/1993 |
| EP | 01651605 | 5/2006 |
| EP | 01651606 | 5/2006 |
| EP | 01651616 | 5/2006 |
| EP | 01651620 | 5/2006 |
| EP | 01613326 | 9/2006 |
| JP | 2001261657 | 9/2001 |
| WO | WO 95/25443 | 9/1995 |
| WO | WO 97/25042 | 7/1997 |
| WO | WO 98/57949 | 12/1998 |
| WO | WO 99/37304 A1 | 7/1999 |
| WO | WO 00/12074 | 3/2000 |
| WO | WO 00/56704 | 9/2000 |
| WO | WO 01/74797 A1 | 10/2001 |
| WO | WO 02/100822 | 12/2002 |
| WO | WO 03/082288 A1 | 10/2003 |
| WO | WO 2004/073606 | 9/2004 |
| WO | WO 2004/092117 | 10/2004 |
| WO | WO 2004/092130 | 10/2004 |
| WO | WO 2004/093879 | 11/2004 |
| WO | WO 2005/011654 | 2/2005 |
| WO | WO 2005/011656 | 2/2005 |
| WO | WO 2005/011657 | 2/2005 |
| WO | WO 2005/011657 A2 | 2/2005 |
| WO | WO 2005/040136 | 5/2005 |
| WO | WO 2005/044797 | 5/2005 |

(Continued)

OTHER PUBLICATIONS

Wikipedia encyclopedia under Hypercholesterolemia.*

*Primary Examiner*—Joseph McKane
*Assistant Examiner*—Yong Chu
(74) *Attorney, Agent, or Firm*—Dennis A. Bennett; Cynthia Hathaway

(57) ABSTRACT

Compounds as modulators of peroxisome proliferator activated receptors, pharmaceutical compositions comprising the same, and methods of treating disease using the same are disclosed.

9 Claims, No Drawings

FOREIGN PATENT DOCUMENTS

| | | |
|---|---|---|
| WO | WO 2005/060958 | 7/2005 |
| WO | WO 2005/115983 | 12/2005 |
| WO | WO 2006/014168 | 2/2006 |
| WO | WO 2006/034279 | 3/2006 |
| WO | WO 2006/034312 | 3/2006 |
| WO | WO 2006/034315 | 3/2006 |
| WO | WO 2006/034338 | 3/2006 |
| WO | WO 2006/034341 | 3/2006 |
| WO | WO 2006/034440 | 3/2006 |
| WO | WO 2006/034441 | 3/2006 |
| WO | WO 2006/034446 | 3/2006 |

* cited by examiner

SULFONYL-SUBSTITUTED BICYCLIC COMPOUNDS AS MODULATORS OF PPAR

This application claims priority to U.S. provisional applications 60/623,252 filed on Oct. 29, 2004 and 60/679,813 filed on May 11, 2005 both of which are hereby incorporated by reference as if written herein in their entirety.

FIELD OF THE INVENTION

The present invention relates to novel sulfonyl-substituted bicyclic aryl derivatives and methods for treating various diseases by modulation of nuclear receptor mediated processes using these compounds, and in particular processes mediated by peroxisome proliferator activated receptors (PPARs).

BACKGROUND OF THE INVENTION

Peroxisome proliferators are a structurally diverse group of compounds whicH, when administered to mammals, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, *Ann. Rev. Cell Biol.* 1:489-530 (1985); Vamecq and Draye, *Essays Biochem.* 24:1115-225 (1989); and Nelali et al., *Cancer Res.* 48:5316-5324 (1988)). Compounds that activate or otherwise interact with one or more of the PPARs have been implicated in the regulation of triglyceride and cholesterol levels in animal models. Compounds included in this group are the fibrate class of hypolipidemic drugs, herbicides, and phthalate plasticizers (Reddy and Lalwani, *Crit. Rev. Toxicol.* 12:1-58 (1983)). Peroxisome proliferation can also be elicited by dietary or physiological factors such as a high-fat diet and cold acclimatization.

Biological processes modulated by PPAR are those modulated by receptors, or receptor combinations, which are responsive to the PPAR receptor ligands. These processes include, for example, plasma lipid transport and fatty acid catabolism, regulation of insulin sensitivity and blood glucose levels, which are involved in hypoglycemia/hyperinsulinemia (resulting from, for example, abnormal pancreatic beta cell function, insulin secreting tumors and/or autoimmune hypoglycemia due to autoantibodies to insulin, the insulin receptor, or autoantibodies that are stimulatory to pancreatic beta cells), macrophage differentiation which lead to the formation of atherosclerotic plaques, inflammatory response, carcinogenesis, hyperplasia, and adipocyte differentiation.

Subtypes of PPAR include PPAR-alpha, PPAR-delta (also known as NUC1, PPAR-beta and FAAR) and two isoforms of PPAR-gamma. These PPARs can regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endodn. Met.* 291-296, 4 (1993)).

Insight into the mechanism whereby peroxisome proliferators exert their pleiotropic effects was provided by the identification of a member of the nuclear hormone receptor superfamily activated by these chemicals (Isseman and Green, *Nature* 347-645-650 (1990)). The receptor, termed PPAR-alpha (or alternatively, PPARα), was subsequently shown to be activated by a variety of medium and long-chain fatty acids and to stimulate expression of the genes encoding rat acyl-CoA oxidase and hydratase-dehydrogenase (enzymes required for peroxisomal β-oxidation), as well as rabbit cytochrome P450 4A6, a fatty acid ω-hydroxylase (Gottlicher et al., *Proc. Natl. Acad. Sci. USA* 89:4653-4657 (1992); Tugwood et al., *EMBO J* 11:433-439 (1992); Bardot et al., *Biochem. Biophys. Res. Comm.* 192:37-45 (1993); Muerhoff et al., *J Biol. Chem.* 267:19051-19053 (1992); and Marcus et al., *Proc. Natl. Acad Sci. USA* 90(12): 5723-5727 (1993).

Activators of the nuclear receptor PPAR-gamma (or alternatively, PPARγ), for example troglitazone, have been clinically shown to enhance insulin-action, to reduce serum glucose and to have small but significant effects on reducing serum triglyceride levels in patients with Type 2 diabetes. See, for example, D. E. Kelly et al., *Curr. Opin. Endocrinol. Diabetes,* 90-96, 5 (2), (1998); M. D. Johnson et al., *Ann. Pharmacother.,* 337-348, 32 (3), (1997); and M. Leutenegger et al., *Curr. Ther. Res.,* 403-416, 58 (7), (1997).

The third subtype of PPAR, PPAR-delta (or alternatively, PPARδ, PPARβ, or NUC1) initially received much less attention than the other PPARs because of its ubiquitous expression and the unavailability of selective ligands. However, genetic studies and recently developed synthetic PPAR-δ agonists have helped reveal its role as a powerful regulator of fatty acid catabolism and energy homeostasis. Studies in adipose tissue and muscle have begun to uncover the metabolic functions of PPAR-δ. Transgenic expression of an activated form of PPAR-δ in adipose tissue produces lean mice that are resistant to obesity, hyperlipidemia and tissue steatosis induced genetically or by a high-fat diet. The activated receptor induces genes required for fatty acid catabolism and adaptive thermogenesis. Interestingly, the transcription of PPAR-γ target genes for lipid storage and lipogenesis remain unchanged. In parallel, PPAR-δ-deficient mice challenged with a high-fat diet show reduced energy uncoupling and are prone to obesity. Together, these data identify PPAR-δ as a key regulator of fat-burning, a role that opposes the fat-storing function of PPAR-γ. Thus, despite their close evolutionary and structural kinship, PPAR-γ and PPAR-δ regulate distinct genetic networks. In skeletal muscle, PPAR-δ likewise upregulates fatty acid oxidation and energy expenditure, to a far greater extent than does the lesser-expressed PPAR-α. (Evans R M et al 2004 *Nature Med* 1-7, 10 (4), 2004)

PPARδ is broadly expressed in the body and has been shown to be a valuable molecular target for treatment of dyslipidemia and other diseases. For example, in a recent study in insulin-resistant obese rhesus monkeys, a potent and selective PPARδ compound was shown to decrease VLDL and increase HDL in a dose response manner (Oliver et al., *Proc. Natl. Acad. Sci. U.S.A.* 98: 5305, 2001). Also, in a recent study in wild-type and HDL-lacking, ABCA1$^{-/-}$ mice, a different potent and selective PPARδ compound was shown to reduce fractional cholesterol absorption in the intestine, and coincidently reduce expression of the cholesterol-absorption protein NPC1L1 (van der Veen et al., *J. Lipid Res.* 2005 46: 526-534).

Because there are three isoforms of PPAR and all of them have been shown to play important roles in energy homeostasis and other important biological processes in human body and have been shown to be important molecular targets for treatment of metabolic and other diseases (see Wilson, et al. *J. Med. Chem.* 43: 527-550 (2000)), it is desired in the art to identify compounds which are capable of interacting with multiple PPAR isoforms or compounds which are capable of selectively interacting with only one of the PPAR isoforms. Such compounds would find a wide variety of uses, such as, for example, in the treatment or prevention of obesity, for the treatment or prevention of diabetes, dyslipidemia, metabolic syndrome X and other uses.

Several PPAR-modulating drugs have been approved for use in humans. Fenofibrate and gemfibrozil are PPARα modulators; pioglitazone (Actos, Takeda Pharmaceuticals and Eli Lilly) and rosiglitazone (Avandia, GlaxoSmithKline) are PPARγ modulators. All of these compounds have liabilities as potential carcinogens, however, having been demonstrated to have proliferative effects leading to cancers of various types (colon; bladder with PPARα modulators and liver with PPARγ modulators) in rodent studies. Therefore, a need exists to identify modulators of PPARs that lack these liabilities.

Additionally, recent evidence points to a role for PPAR-δ in the development of cancers, including colon, skin, and lung cancers. Modulators of PPAR could therefore find use in the treatment of cancers of various types.

SUMMARY OF THE INVENTION

The present invention relates to sulfonyl-substituted bicyclic compounds, useful as modulators of PPAR and methods of treating metabolic disorders. One embodiment of the invention are compounds having structural Formula (I)

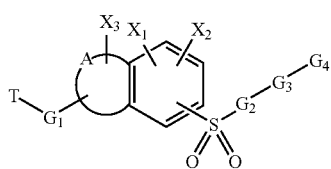

(I)

Or a salt, ester, or prodrug thereof, wherein;

A is a saturated or unsaturated hydrocarbon chain or a heteroatom-comprising hydrocarbon chain having from 3 to 5 atoms, forming a five- to seven-membered ring;

T is selected from the group consisting of —C(O)OH, —C(O)NH$_2$, and tetrazole;

$G_1$ is selected from the group consisting of —$(CR^1R^2)_n$—, —$Z(CR^1R^2)_n$—, —$(CR^1R^2)_nZ$—, —$(CR^1R^2)_rZ(CR^1R^2)_s$—;

Z is O, S or NR;

n is 0, 1, or 2;

r and s are independently 0 or 1;

$R^1$ and $R^2$ are independently selected from the group consisting of hydrogen, halo, optionally substituted lower alkyl, optionally substituted lower heteroalkyl, optionally substituted lower alkoxy, and lower perhaloalkyl or together may form an optionally substituted cycloalkyl;

$X_1$, $X_2$, and $X_3$ are independently selected from the group consisting of hydrogen, optionally substituted lower alkyl, optionally substituted cycloalkyl, halogen, perhaloalkyl, hydroxy, optionally substituted lower alkoxy, nitro, cyano, and NH$_2$;

$G_2$ is selected from the group consisting of a saturated or unsaturated cycloalkyl or heterocycloalkyl linker, optionally substituted with $X_4$ and $X_5$;

$X_4$ and $X_5$ are independently selected from the group consisting of hydrogen, optionally substituted lower alkyl, halogen, lower perhaloalkyl, hydroxy, optionally substituted lower alkoxy, nitro, cyano, NH$_2$, and CO$_2$R;

R is selected from the group consisting of optionally substituted lower alkyl and hydrogen;

$G_3$ is selected from the group consisting of a bond, a double bond, —$(CR^3R^4)_m$—, carbonyl, and —$(CR^3R^4)_m$CR$^3$=CR$^4$—;

m is 0, 1, or 2;

$R^3$ and $R^4$ are independently selected from the group consisting of hydrogen, optionally substituted lower alkyl, optionally substituted lower alkoxy, optionally substituted aryl, lower perhaloalkyl, cyano, and nitro;

$G_4$ is selected from the group consisting of hydrogen, optionally substituted aryl, optionally substituted heteroaryl, optionally substituted cycloalkyl, optionally substituted cycloheteroalkyl, optionally substituted cycloheteroaryl, optionally substituted cycloalkenyl, and —N=(CR$^5$R$^6$); and $R^5$ and $R^6$ are independently selected from the group consisting of hydrogen, optionally substituted aryl, optionally substituted heteroaryl, optionally substituted cycloalkyl, optionally substituted cycloalkenyl, and optionally substituted cycloheteroalkyl.

The present invention also provides for pharmaceutical compositions comprising the compounds of the invention together with a pharmaceutically acceptable diluent or carrier.

The present invention also discloses that bicyclic moieties substituted with an acid or ester moiety and a sulfonyl moiety can modulate at least one peroxisome proliferator-activated receptor (PPAR) function. Compounds described herein may be modulating both PPAR-delta and PPAR-gamma or PPAR-alpha and PPAR-delta, or all three PPAR subtypes, or selectively modulating predominantly PPAR-gamma, PPAR-alpha or PPAR-delta. Thus, the present invention provides for a method of modulating PPAR comprising contacting said PPAR with a compound of the invention. In certain preferred embodiments, said modulation is selective for PPARδ over PPARα and PPARγ. In certain more preferred embodiments, said modulation of PPARδ is 100-fold selective or greater over said other isoforms. Most preferably, said modulation is 200- to 500-fold selective over said other isoforms.

The present invention also relates to a method of modulating at least one peroxisome proliferator-activated receptor (PPAR) function comprising the step of contacting the PPAR with a compound of Formula I, as described herein. The change in cell phenotype, cell proliferation, activity of the PPAR, expression of the PPAR or binding of the PPAR with a natural binding partner may be monitored. Such methods may be modes of treatment of disease, biological assays, cellular assays, biochemical assays, or the like.

The present invention also describes methods of treating a disease comprising identifying a patient in need thereof, and administering a therapeutically effective amount of a compound of Formula I, as described herein, to the patient. Thus, in certain embodiments, the disease to be treated by the methods of the present invention is selected from the group consisting of obesity, diabetes, hyperinsulinemia, metabolic syndrome X, polycystic ovary syndrome, climacteric, disorders associated with oxidative stress, inflammatory response to tissue injury, pathogenesis of emphysema, ischemia-associated organ injury, doxorubicin-induced cardiac injury, drug-induced hepatotoxicity, atherosclerosis, and hypertoxic lung injury. In another aspect, the present invention relates to a method of modulating at least one peroxisome proliferator-activated receptor (PPAR) function comprising the step of contacting the PPAR with a compound of Formula I, as described herein. The change in cell phenotype, cell proliferation, activity of the PPAR, or binding of the PPAR with a natural binding partner may be monitored. Such methods may be modes of treatment of disease, biological assays, cellular assays, biochemical assays, or the like. In certain embodiments, the PPAR may be selected from the group consisting of PPARα, PPARδ, and PPARγ.

DETAILED DESCRIPTION OF THE INVENTION

In certain embodiments, the invention provides compounds of Formula I wherein T is —C(O)OH.

In other embodiments, the invention provides compounds of Formula I wherein A has three atoms and forms a five-membered ring.

In related embodiments, at least one of said three atoms of A is a heteroatom selected from the group consisting of N, O, and S.

In other embodiments, the invention provides compounds of Formula I having structural formulae selected from the group consisting of:

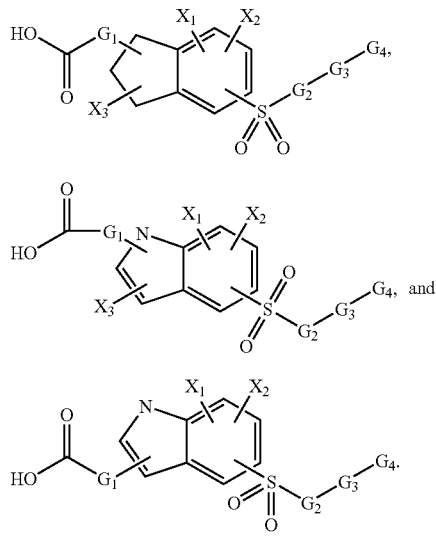

In other embodiments, the invention provides compounds of Formula I having structural formula (III) selected from the group consisting of:

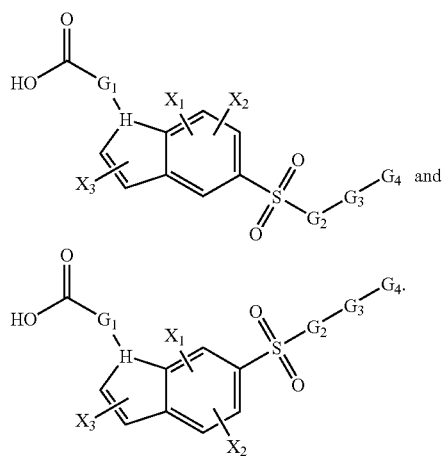

In other embodiments, the invention provides compounds of Formula I having structural formula (IV) selected from the group consisting of:

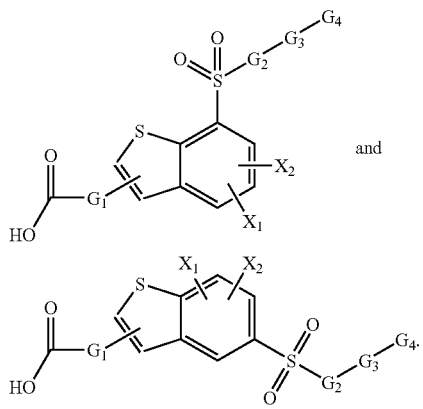

In other embodiments, the invention provides compounds of Formula I having structural formula selected from the group consisting of:

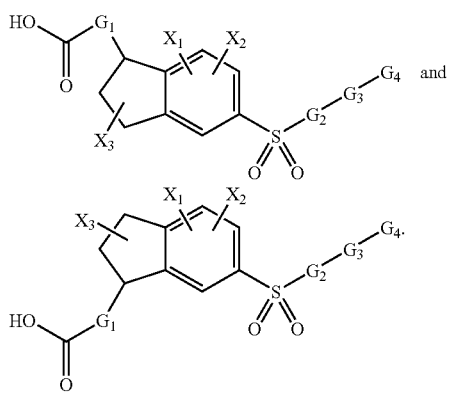

In other embodiments, the invention provides compounds of Formula I having structural formula selected from the group consisting of:

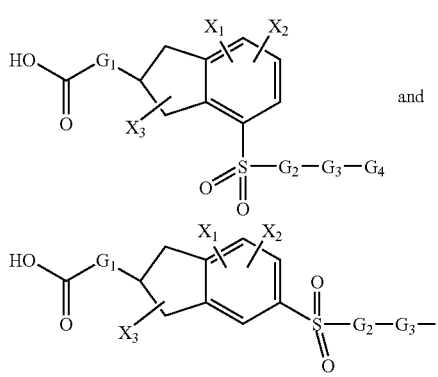

In certain embodiments, the invention provides compounds Formula I wherein:

$G_1$ is —$(CR^1R^2)_n$—;

With the proviso that if A is a 5 carbon chain, n is 0 or 1;

$G_2$ has the structure:

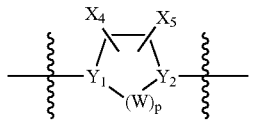

$Y_1$ and $Y_2$ are independently selected from the group consisting of N and C—$X_6$;

$X_4$ and $X_5$ are independently selected from the group consisting of hydrogen, optionally substituted lower alkyl, halogen, lower perhaloalkyl, hydroxy, optionally substituted lower alkoxy, nitro, cyano, $NH_2$, and $CO_2R$, or $X_4$ and $X_5$ together may form a carbocycle;

R is selected from the group consisting of lower alkyl and hydrogen;

p is 1, 2 or 3;

W is selected from the group consisting of —$CX_4X_5$— and N—$X_7$;

$X_4$ and $X_5$ are independently selected from the group consisting of hydrogen, optionally substituted lower alkyl, halogen, lower perhaloalkyl, hydroxy, optionally substituted lower alkoxy, nitro, cyano, $NH_2$, and $CO_2R$;

$X_6$ is selected from the group consisting of hydrogen, alkyl, hydroxy, alkoxy, cyano, halogen, lower perhaloalkyl and $NH_2$ or null when forming a double bond with an adjacent ring atom; and $X_7$ is selected from the group consisting of hydrogen, alkyl, hydroxy, and lower perhaloalkyl, or null when forming a double bond with $Y_2$.

In certain preferred embodiments, the invention provides compounds Formula I wherein p is 2, W is —$CX_4X_5$—, and $Y_1$ is N. In other preferred embodiments, p is 2, W is —$CX_4X_5$—, and $Y_1$ and $Y_2$ are N.

In certain embodiments, the invention provides compounds of Formula I wherein $G_1$ is —$(CR^1R^2)_n$—. In certain preferred embodiments, n is 0 or 1. In other preferred embodiments, $R^1$ and $R^2$ may be independently selected from the group consisting of hydrogen, methyl, ethyl, and propyl, or together may form a cyclopropyl, cyclobutyl, cyclopentyl, or cyclohexyl. In even more preferred embodiments, $R^1$ and $R^2$ are hydrogen.

In certain embodiments, the invention provides compounds of Formula I wherein $G_3$ is a bond.

In certain embodiments, the invention provides compounds of Formula I wherein $G_4$ is selected from the group consisting of optionally substituted aryl and optionally substituted heteroaryl. In certain preferred embodiments, $G_4$ may be optionally substituted phenyl or optionally substituted pyridinyl. In even more preferred embodiments, $G_4$ may be singly or doubly substituted with halogen, lower alkyl, lower perhaloalkyl, lower haloalkoxy, or lower perhaloalkoxy. In related embodiments, $G_4$ may have a structural formula selected from the group consisting of:

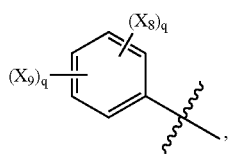

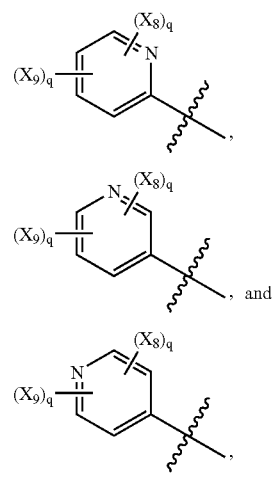

wherein:

q is 1 to 3;

$X_8$ and $X_9$ are independently selected from the group consisting of hydrogen, alkyl, halogen, lower perhaloalkyl, lower perhaloalkoxy or mono- or di-haloalkoxy, hydroxy, alkoxy, nitro, cyano, $NH_2$, and $CO_2R$; and R is selected from the group consisting of lower alkyl and hydrogen.

In certain preferred embodiments, the invention provides compounds of Formula I having structural formulae selected from the group consisting of:

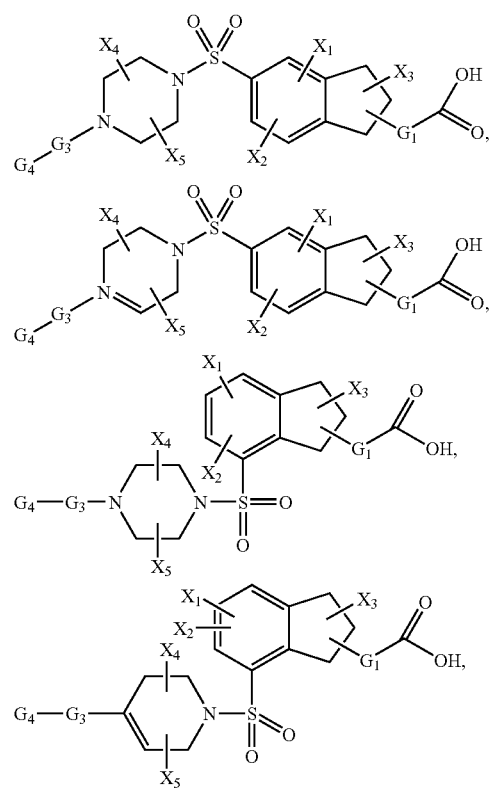

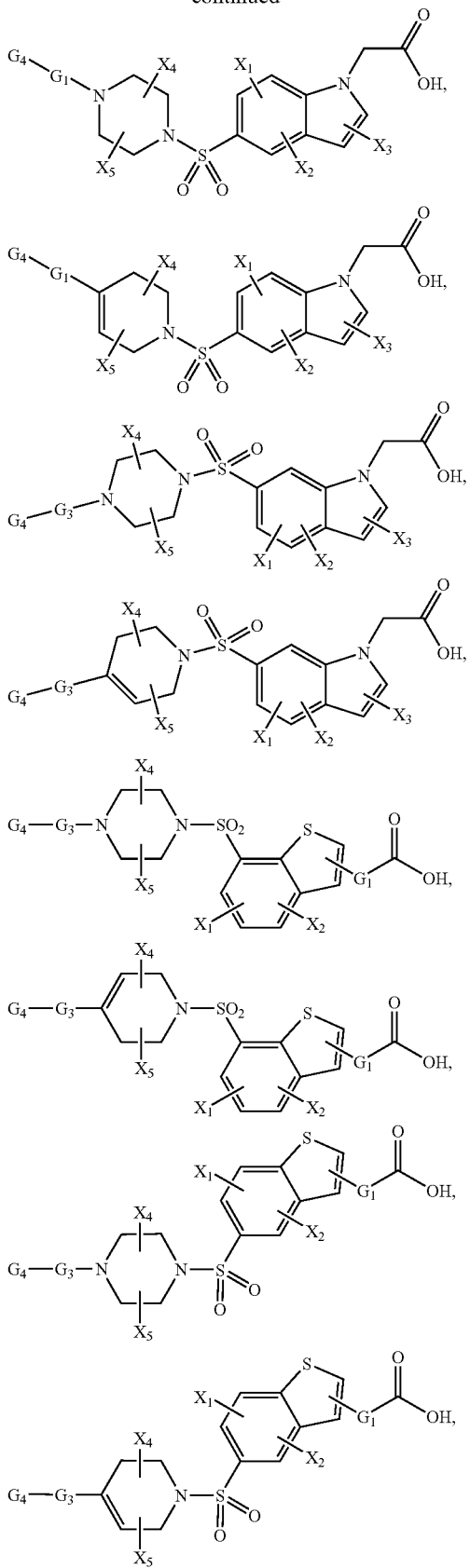

wherein $G_1$ is selected from the group consisting of —$(CR^1R^2)_n$— and —$(CR^1R^2)_nO$—, and other groups are as previously defined.

In certain preferred embodiments, the invention provides compounds of Formula I wherein $X_1$, $X_2$, and $X_3$ are independently selected from the group consisting of hydrogen, halogen, lower alkyl, and lower alkoxy. In certain preferred embodiments, $X_1$, $X_2$, and $X_3$ are independently selected from the group consisting of hydrogen, methyl, ethyl, propyl, and halogen. In other preferred embodiments, $X_1$, $X_2$, and $X_3$ may be independently selected from the group consisting of hydrogen and methyl.

Another aspect of the invention are pharmaceutical compositions comprising compounds of Formula I together with pharmaceutically acceptable diluents or carriers.

The present invention discloses that novel compounds of Formula I, disclosed herein, can modulate at least one peroxisome proliferator-activated receptor (PPAR) function. Compounds described herein may be activating both PPARδ and PPARγ or PPARα and PPARδ, or all three PPAR subtypes, or selectively activating predominantly PPARγ, PPARα or PPARδ.

Thus, in one aspect, the present invention discloses a method of modulating at least one peroxisome proliferator-activated receptor (PPAR) function comprising the step of contacting the PPAR with a compound of Formula I, as described herein. The change in cell phenotype, cell proliferation, activity of the PPAR, expression of the PPAR or binding of the PPAR with a natural binding partner may be monitored. Such methods may be modes of treatment of disease, biological assays, cellular assays, biochemical assays, or the like.

In another aspect, the present invention discloses methods of treatment of a PPAR-delta mediated disease or condition comprising identifying a patient in need, administering a therapeutically effective amount of a compound of Formula I or a pharmaceutically acceptable salt, ester, amide, or prodrug thereof. In certain embodiments of this aspect, the present invention discloses methods: for raising HDL, lowering LDLc, shifting LDL particle size from small dense to normal LDL, or inhibiting cholesterol absorption in a subject; for decreasing insulin resistance or lowering blood pressure in a subject; for treating obesity, diabetes, especially Type 2 diabetes, hyperinsulinemia, metabolic syndrome X, dyslipidemia, and hypercholesterolemia; for treating cardiovascular diseases including vascular disease, atherosclerosis, coronary heart disease, cerebrovascular disease, heart failure and peripheral vessel disease in a subject; for treating cancers including colon, skin, and lung cancers in a subject; for treating inflammatory diseases, including asthma, rheumatoid arthritis, osteoarthritis, disorders associated with oxidative stress, inflammatory response to tissue injury, psoriasis, ulcerative colitis, dermatitis, and autoimmune disease in a subject; and for treating polycystic ovary syndrome, climacteric pathogenesis of emphysema, ischemia-associated organ injury, doxorubicin-induced cardiac injury, drug-induced hepatotoxicity, hypertoxic lung injury, scarring, wound healing, anorexia nervosa and bulimia nervosa in a subject, all comprising the administration of a therapeutic amount of a compound of Formula I. Preferably, the PPAR may be selected from the group consisting of PPARα, PPARδ, and PPARγ. More preferably, the PPAR is PPARδ.

In yet another aspect, the invention further discloses compounds of Formula I or pharmaceutical compositions thereof for use in the manufacture of a medicament for the prevention or treatment of a disease or condition ameliorated by the modulation of a PPAR. The invention also discloses the use of a compound of Formula I according to the invention for the manufacture of a medicament: for raising HDL, lowering LDLc, shifting LDL particle size from small dense to normal LDL, or inhibiting cholesterol absorption in a subject; for decreasing insulin resistance or lowering blood pressure in a subject; for treating obesity, diabetes, especially Type 2 diabetes, hyperinsulinemia, metabolic syndrome X, dyslipidemia, and hypercholesterolemia; for treating cardiovascular diseases including vascular disease, atherosclerosis, coronary heart disease, cerebrovascular disease, heart failure and peripheral vessel disease in a subject; for treating cancers including colon, skin, and lung cancers in a subject; for treating inflammatory diseases, including asthma, rheumatoid arthritis, osteoarthritis, disorders associated with oxidative stress, inflammatory response to tissue injury, psoriasis, ulcerative colitis, dermatitis, and autoimmune disease in a subject; and for treating polycystic ovary syndrome, climacteric, pathogenesis of emphysema, ischemia-associated organ injury, doxorubicin-induced cardiac injury, drug-induced hepatotoxicity, hypertoxic lung injury, scarring, wound healing, anorexia nervosa and bulimia nervosa in a subject, all comprising the administration of a therapeutic amount of a compound of Formula I. Preferably, the PPAR may be selected from the group consisting of PPAR$\alpha$, PPAR$\delta$, and PPAR$\gamma$. More preferably, the PPAR is PPAR$\delta$.

In yet another aspect, the present invention provides for compounds of Formula I or pharmaceutical compositions thereof for use in the treatment of a disease or condition ameliorated by the modulation of a PPAR. Such PPAR-mediated diseases and conditions may be selected without limitation from those listed in the preceding paragraphs. Preferably, the PPAR may be selected from the group consisting of PPAR$\alpha$, PPAR$\delta$, and PPAR$\gamma$. More preferably, the PPAR is PPAR$\delta$.

Another aspect of the invention are compounds of Formula I, pharmaceutically acceptable prodrugs, pharmaceutically active metabolites, or pharmaceutically acceptable salts thereof having an $EC_{50}$ value less than 5 µM against PPAR as measured by functional cell assay. Preferably, said compounds have $EC_{50}$ values less than 5 µM against PPAR$\delta$.

Another aspect of the invention are compounds which modulate a peroxisome proliferator-activated receptor (PPAR) function, wherein said PPAR is selected from the group consisting of PPAR$\alpha$, PPAR$\delta$, and PPAR$\gamma$. Preferably, said modulation is selective for PPAR$\delta$ over the other isoforms. More preferably, said modulation is 100-fold selective or greater for PPAR$\delta$. Most preferably, said modulation is 200-500 fold selective for PPAR$\delta$.

As used in the present specification the following terms have the meanings indicated:

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$, group.

The term "acylamino" embraces an amino radical substituted with an acyl group. An example of an "acylamino" radical is acetylamino (CH$_3$C(O)NH—).

The term "alkenyl," as used herein, alone or in combination, refers to a straight-chain or branched-chain hydrocarbon radical having one or more double bonds and containing from 2 to 20 carbon atoms. Alkenylene refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy, ethoxyethoxy, methoxypropoxyethoxy, ethoxypentoxyethoxyethoxy and the like.

The term "alkoxyalkoxy," as used herein, alone or in combination, refers to an alkoxy group attached to the parent molecular moiety through another alkoxy group.

The term "alkoxyalkyl," as used herein, alone or in combination, refers to an alkoxy group attached to the parent molecular moiety through an alkyl group.

The term "alkoxycarbonyl," as used herein, alone or in combination, refers to an alkoxy group attached to the parent molecular moiety through a carbonyl group.

The term "alkyl," as used herein, alone or in combination, refers to a straight-chain or branched-chain alkyl radical containing from 1 to and including 20 carbon atoms. Alkyl, alone or in combination, refers to an alkyl radical which is optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "alkylamino," as used herein, alone or in combination, refers to an amino group attached to the parent molecular moiety through an alkyl group.

The term "alkylcarbonyl" and "alkanoyl," as used herein, alone or in combination, refers to an alkyl group attached to the parent molecular moiety through a carbonyl group. Examples of such groups include methylcarbonyl and ethylcarbonyl.

The term "alkylene," as used herein, alone or in combination, refers to a saturated aliphatic group derived from a straight or branched chain saturated hydrocarbon attached at two or more positions, such as methylene (—CH$_2$—).

The term "alkylidene," as used herein, alone or in combination, refers to an alkenyl group in which one carbon atom of the carbon-carbon double bond belongs to the moiety to which the alkenyl group is attached.

The term "alkylsulfinyl," as used herein, alone or in combination, refers to an alkyl group attached to the parent molecular moiety through a sulfinyl group.

The term "alkylsulfonyl," as used herein, alone or in combination, refers to an alkyl group attached to the parent molecular moiety through a sulfonyl group.

The term "alkylthio," as used herein, alone or in combination, refers to an alkyl thioether (R—S—) radical wherein the term alkyl is as defined above. Examples of suitable alkyl thioether radicals include methylthio, ethylthio, n-propylthio, isopropylthio, n-butylthio, iso-butylthio, sec-butylthio, tert-butylthio, ethoxyethylthio, methoxypropoxyethylthio, ethoxypentoxyethoxyethylthio and the like.

The term "alkynyl," alone or in combination, alone or in combination, refers to a straight-chain or branched chain hydrocarbon radical having one or more triple bonds and containing preferably from 2 to 20 carbon atoms. Alkynylene refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl, and the like.

The term "amido," as used herein, alone or in combination, refers to an amino group as described below attached to the parent molecular moiety through a carbonyl group. The term "C-amido" as used herein, alone or in combination, refers to a —C(=O)—NR$_2$ group with R as defined herein. The term "N-amido" as used herein, alone or in combination, refers to a RC(=O)NH— group, with R as defined herein.

The term "amino," as used herein, alone or in combination, refers to —NRR', wherein R and R' are independently selected from the group consisting of hydrogen, alkenyl, alkoxy, alkoxyalkyl, alkoxycarbonyl, alkyl, alkylcarbonyl, aryl, arylalkenyl, arylalkyl, cycloalkyl, haloalkylcarbonyl, heteroaryl, heteroarylalkenyl, heteroarylalkyl, heterocycle, heterocycloalkenyl, and heterocycloalkyl, wherein the aryl, the aryl part of the arylalkenyl, the arylalkyl, the heteroaryl, the heteroaryl part of the heteroarylalkenyl and the heteroarylalkyl, the heterocycle, and the heterocycle part of the heterocycloalkenyl and the heterocycloalkyl can be optionally substituted with one, two, three, four, or five substituents independently selected from the group consisting of alkenyl, alkoxy, alkoxyalkyl, alkyl, cyano, halo, haloalkoxy, haloalkyl, hydroxy, hydroxy-alkyl, nitro, and oxo.

The term "aminoalkyl," as used herein, alone or in combination, refers to an amino group attached to the parent molecular moiety through an alkyl group.

The terms "aminocarbonyl" and "carbamoyl," as used herein, alone or in combination, refer to an amino-substituted carbonyl group, wherein the amino group can be a primary or secondary amino group containing substituents selected from alkyl, aryl, aralkyl, cycloalkyl; cycloalkylalkyl radicals and the like.

The term "aralkenyl" or "arylalkenyl," as used herein, alone or in combination, refers to an aryl group attached to the parent molecular moiety through an alkenyl group.

The term "aralkoxy" or "arylalkoxy," as used herein, alone or in combination, refers to an aryl group attached to the parent molecular moiety through an alkoxy group.

The term "aralkyl" or "arylalkyl," as used herein, alone or in combination, refers to an aryl group attached to the parent molecular moiety through an alkyl group.

The term "aralkylamino" or "arylalkylamino," as used herein, alone or in combination, refers to an arylalkyl group attached to the parent molecular moiety through a nitrogen atom, wherein the nitrogen atom is substituted with hydrogen.

The term "aralkylidene" or "arylalkylidene," as used herein, alone or in combination, refers to an aryl group attached to the parent molecular moiety through an alkylidene group The term "aralkylthio" or "arylalkylthio," as used herein, alone or in combination, refers to an arylalkyl group attached to the parent molecular moiety through a sulfur atom.

The term "aralkynyl" or "arylalkynyl," as used herein, alone or in combination, refers to an aryl group attached to the parent molecular moiety through an alkynyl group.

The term "aralkoxycarbonyl," as used herein, alone or in combination, refers to a radical of the formula aralkyl-O—C(O)— in which the term "aralkyl," has the significance given above. Examples of an aralkoxycarbonyl radical are benzyloxycarbonyl (Z or Cbz) and 4-methoxyphenylmethoxycarbonyl (MOS).

The term "aralkanoyl," as used herein, alone or in combination, refers to an acyl radical derived from an aryl-substituted alkanecarboxylic acid such as benzoyl, phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl" refers to an acyl radical derived from an arylcarboxylic acid, "aryl" having the meaning given below. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aryl", alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The terms "arylcarbonyl" and "aroyl," as used herein, alone or in combination, refer to an aryl group attached to the parent molecular moiety through a carbonyl group.

The term "aryloxy," as used herein, alone or in combination, refers to an aryl group attached to the parent molecular moiety through an oxygen atom.

The term "arylsulfonyl," as used herein, alone or in combination, refers to an aryl group attached to the parent molecular moiety through a sulfonyl group.

The term "arylthio," as used herein, alone or in combination, refers to an aryl group attached to the parent molecular moiety through a sulfur atom.

The terms "benzo" and "benz," as used herein, alone or in combination, refer to the divalent radical $C_6H_4$= derived from benzene. Examples include benzothiophene and benzimidazole.

The term "O-carbamyl" as used herein, alone or in combination, refers to a —OC(O)NR, group-with R as defined herein.

The term "N-carbamyl" as used herein, alone or in combination, refers to a ROC(O)NH— group, with R as defined herein.

The term "carbonyl," as used herein, when alone includes formyl [—C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by bicyclo[2,2,2] octane, bicyclo[2,2,2]octane, bicyclo[1,1,1]pentane, camphor and bicyclo[3,2,1]octane.

The term "cycloalkylalkyl," as used herein, alone or in combination, refers to an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

The term "cycloalkylcarbonyl," as used herein, alone or in combination, refers to an acyl radical of the formula cycloalkyl-(C=O)— in which the term "cycloalkyl" has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like.

The term "ester," as used herein, alone or in combination, refers to an alkoxy, aryloxy, cycloalkoxy, heteroaryloxy, and heterocyclooxy attached to a carbonyl group.

The term "ether," as used herein, alone or in combination, refers to an oxy group bridging two moieties linked at carbon atoms.

The term "halo," or "halogen," as used herein, alone or in combination, refers to F, Cl, Br, or I.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a halohydrocarbyl group attached at two or more positions. Examples include fluoromethylene (—CFH—), difluoromethylene (—CF$_2$—), chloromethylene (—CHCl—) and the like. Examples of such haloalkyl radicals include chloromethyl, 1-bromoethyl, fluoromethyl, difluoromethyl, trifluoromethyl, 1,1,1-trifluoroethyl, perfluorodecyl and the like.

The term "haloalkylcarbonyl," as used herein, alone or in combination, refers to a haloalkyl group attached to the parent molecular moiety through a carbonyl group.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH2—NH—OCH3.

The term "heteroaryl" embraces unsaturated heterocyclic radicals. Such unsaturated heterocyclic radicals, also termed "heteroaryl" radicals, refer to 3 to 7 membered, preferably 5 to 7 membered, rings wherein at least one atom is selected from the group consisting of O, S, and N. Heteroaryl groups are exemplified by: unsaturated 3 to 7 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic groups containing an oxygen atom, for example, pyranyl, furyl, etc.; unsaturated 3 to 6-membered heteromonocyclic groups containing a sulfur atom, for example, thienyl, etc.; unsaturated 3- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic groups containing 1 to 2 oxygen atoms and 1 to 3 nitrogen atoms [e.g. benzoxazolyl, benzoxadiazolyl, etc.]; unsaturated 3 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] and isothiazolyl; unsaturated condensed heterocyclic groups containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like.

The term "heteroarylalkenyl," as used herein, alone or in combination, refers to a heteroaryl group attached to the parent molecular moiety through an alkenyl group.

The term "heteroarylalkoxy," as used herein, alone or in combination, refers to a heteroaryl group attached to the parent molecular moiety through an alkoxy group.

The term "heteroarylalkyl," as used herein, alone or in combination, refers to a heteroaryl group attached to the parent molecular moiety through an alkyl group.

The term "heteroarylalkylidene," as used herein, alone or in combination, refers to a heteroaryl group attached to the parent molecular moiety through an alkylidene group.

The term "heteroaryloxy," as used herein, alone or in combination, refers to a heteroaryl group attached to the parent molecular moiety through an oxygen atom.

The term "heteroarylsulfonyl," as used herein, alone or in combination, refers to a heteroaryl group attached to the parent molecular moiety through a sulfonyl group.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "heterocycloalkenyl," as used herein, alone or in combination, refers to a heterocycle group attached to the parent molecular moiety through an alkenyl group.

The term "heterocycloalkoxy," as used herein, alone or in combination, refers to a heterocycle group attached to the parent molecular group through an oxygen atom.

The term "heterocycloalkyl," as used herein, alone or in combination, refers to an alkyl radical as defined above in which at least one hydrogen atom is replaced by a heterocyclo radical as defined above, such as pyrrolidinylmethyl, tetrahydrothienylmethyl, pyridylmethyl and the like.

The term "heterocycloalkylidene," as used herein, alone or in combination, refers to a heterocycle group attached to the parent molecular moiety through an alkylidene group.

The term "hydrazinyl" as used herein, alone or in combination, refers to two amino groups joined by a single bond, i.e., —N—N—.

The term "hydroxy," as used herein, alone or in combination, refers to OH, The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptoalkyl" refers to a R'SR— group, where R and R' are as defined herein.

The term "mercaptomercaptyl" refers to a RSR'S— group, where R is as defined herein.

The term "mercaptyl" refers to a RS— group, where R is as defined herein.

The term "null" refers to a lone electron pair.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" refers to an alkyl group where all of the hydrogen atoms are replaced by halogen atoms.

The terms "sulfonate," "sulfonic acid, " and "sulfonic," as used herein, alone or in combination, refer the —$SO_3H$ group and its anion as the sulfonic acid is used in salt formation.

The term "sulfanyl," as used herein, alone or in combination, refers to —S and —S—.

The term "sulfinyl," as used herein, alone or in combination, refers to —S(O)—.

The term "sulfonyl," as used herein, alone or in combination, refers to —$SO_2$—.

The term "N-sulfonamido" refers to a RS(=O)$_2$NH— group with R as defined herein.

The term "S-sulfonamido" refers to a —S(=O)$_2$NR$_2$, group, with R as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thioether," as used herein, alone or in combination, refers to a thio group bridging two moieties linked at carbon atoms.

The term "thiol," as used herein, alone or in combination, refers to an —SH group. The term "thiocarbonyl," as used herein, when alone includes thioformyl [—(C=S)—H] and in combination is a —C=S— group.

The term "N-thiocarbamyl" refers to an ROC(=S)NH— group, with R as defined herein.

The term "O-thiocarbamyl" refers to a —OC(=S)—NR, group with R as defined herein.

The term "thiocyanato" refers to a —CNS group.

The term "trihalomethanesulfonamido" refers to a $X_3$CS(=O)$_2$NR— group with X is a halogen and R as defined herein.

The term "trihalomethanesulfonyl" refers to a $X_3$CS(=O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, or mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "optionally substituted" means the anteceding group may be substituted or unsubstituted. When substituted, the substituents of an "optionally substituted" group may include, without limitation, one or more substituents independently selected from the following groups or designated subsets thereof, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower haloalkoxy, oxo, lower alkoxy, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, $NHCH_3$, $N(CH_3)_2$, SH, $SCH_3$, $C(O)CH_3$, $CO_2CH_3$, $CO_2H$, $C(O)NH_2$, pyridinyl, thiophene, furanyl, lower carbamate, and lower urea. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended.

The term R or the term R', appearing by itself and without a number designation, unless otherwise defined, refers to an optionally substituted moiety selected from the group consisting of alkyl, cycloalkyl, heteroalkyl, aryl, heteroaryl and heterocycloalkyl. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence.

The term "bond" refers to a covalent linkage between two atoms, or two moieties when the atoms joined by the bond are considered to be part of larger substructure. A bond may be single, double, or triple unless otherwise specified.

In the event that $G_3$ is designated to be "a bond", the structure shown below (right side) is intended: the entity designated $G_3$ collapses to a single bond connecting $G_2$ and $G_4$:

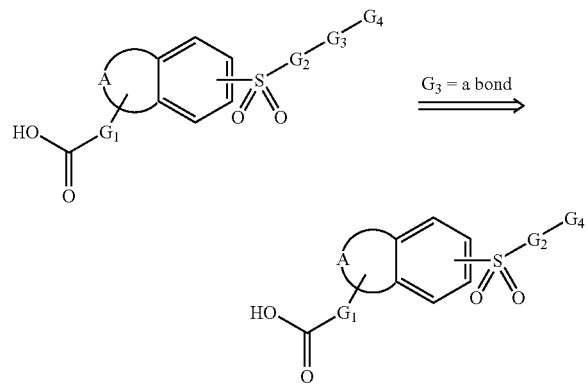

Similarly, when, within $G_1$, n is 0 or both r and s are 0, $G_1$ collapses to a bond connecting A and T.

The compounds of the present invention can exist as therapeutically acceptable salts.

The term "therapeutically acceptable salt," as used herein, represents salts or zwitterionic forms of the compounds of the present invention which are water or oil-soluble or dispersible, which are suitable for treatment of diseases without undue toxicity, irritation, and allergic-response; which are commensurate with a reasonable benefit/risk ratio, and which are effective for their intended use. The salts can be prepared during the final isolation and purification of the compounds or separately by reacting a basic group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, male-ate, mesitylenesulfonate, methanesulfonate, naphthylene-sulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "prodrug" refers to a compound that is made more active in vivo. The present compounds can also exist as prodrugs. Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

The term "activate" refers to increasing the cellular function of a PPAR.

The term "inhibit" refers to decreasing the cellular function of a PPAR. The PPAR function may be the interaction with a natural binding partner or catalytic activity.

The term "modulate" refers to the ability of a compound of the invention to alter the function of a PPAR. A modulator may activate the activity of a PPAR. The term "modulate" also refers to altering the function of a PPAR by increasing or decreasing the probability that a complex forms between a PPAR and a natural binding partner. A modulator may increase the probability that such a complex forms between the PPAR and the natural binding partner, may increase or decrease the probability that a complex forms between the PPAR and the natural binding partner depending on the concentration of the compound exposed to the PPAR, and or may decrease the probability that a complex forms between the PPAR and the natural binding partner.

As used herein, reference to "treatment" of a patient is intended to include prophylaxis. The term "patient" means all mammals including humans. Examples of patients include humans, cows, dogs, cats, goats, sheep, pigs, and rabbits.

The term "therapeutically effective amount" as used herein refers to that amount of the compound being administered which will relieve to some extent one or more of the symptoms of the disease, condition or disorder being treated. In reference to the treatment of diabetes or dyslipidemia a therapeutically effective amount may refer to that amount which has the effect of (1) reducing the blood glucose levels; (2) normalizing lipids, e.g. triglycerides, low-density lipoprotein; (3) relieving to some extent (or, preferably, eliminating) one or more symptoms associated with the disease, condition or disorder to be treated; and/or (4) raising HDL.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition (including, but not limited to, metabolic disorders), previous therapy, the patient's health status and response to the drugs, and the judgment of the treating physician. It is considered well within the skill of the art for one to determine such enhancing-effective amounts by routine experimentation.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

In another aspect, the present invention relates to a method of treating a disease comprising identifying a patient in need thereof, and administering a therapeutically effective amount of a compound of Formula I, as described herein, to the patient.

The compounds of the invention are useful in the treatment of a disease or condition ameliorated by the modulation of an PPAR-delta. Specific diseases and conditions modulated by PPAR-delta and for which the compounds and compositions are useful include but are not limited to dyslipidemia, syndrome X, heart failure, hypercholesteremia, cardiovascular disease, type II diabetes mellitus, type I diabetes, insulin resistance hyperlipidemia, obesity, anorexia bulimia, inflammation and anorexia nervosa. Other indications include reduction of scarring and wound healing.

The compounds of the invention may also be used (a) for raising HDL in a subject; (b) for treating Type 2 diabetes, decreasing insulin resistance or lowering blood pressure in a subject; (c) for decreasing LDLc in a subject; (d) for shifting LDL particle size from small dense to normal dense LDL in a subject; (e) for reducing cholesterol absorption or increasing cholesterol excretion in a subject; (f) for reducing the expression of NPC1L1 in a subject; (g) for treating atherosclerotic diseases including vascular disease, coronary heart disease, cerebrovascular disease and peripheral vessel disease in a subject; and (h) for treating inflammatory diseases, including asthma, rheumatoid arthritis, osteoarthritis, disorders associated with oxidative stress, inflammatory response to tissue injury, psoriasis, ulcerative colitis, dermatitis, and autoimmune disease in a subject.

The compounds of the invention may also be used for treating, ameliorating, or preventing a disease or condition selected from the group consisting of obesity, diabetes, hyperinsulinemia, metabolic syndrome X, polycystic ovary syndrome, climacteric, disorders associated with oxidative stress, inflammatory response to tissue injury, pathogenesis of emphysema, ischemia-associated organ injury, doxorubicin-induced cardiac injury, drug-induced hepatotoxicity, atherosclerosis, and hypertoxic lung injury.

The compositions containing the compound(s) described herein can be administered for prophylactic and/or therapeutic treatments. In therapeutic applications, the compositions are administered to a patient already suffering from a disease, condition or disorder mediated, modulated or involving the PPARs, including but not limited to metabolic diseases, conditions, or disorders, as described above, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

In prophylactic applications, compositions containing the compounds described herein are administered to a patient susceptible to or otherwise at risk of a particular disease, disorder or condition mediated, modulated or involving the PPARs, including but not limited to metabolic diseases, conditions, or disorders, as described above. Such an amount is defined to be a "prophylactically effective amount or dose." In this use, the precise amounts also depend on the patient's state of healtH, weight, and the like. It is considered well within the skill of the art for one to determine such prophylactically effective amounts by routine experimentation (e.g., a dose escalation clinical trial).

Once improvement of the patient's conditions has occurred, a maintenance dose is administered if necessary. Subsequently, the dosage or the frequency of administration, or botH, can be reduced, as a function of the symptoms, to a level at which the improved disease, disorder or condition is retained. When the symptoms have been alleviated to the desired level, treatment can cease. Patients can, however, require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day.

In certain instances, it may be appropriate to administer at least one of the compounds described herein (or a pharmaceutically acceptable salt, ester, amide, prodrug, or solvate) in combination with another therapeutic agent. By way of example only, if one of the side effects experienced by a patient upon receiving one of the compounds herein is hypertension, then it may be appropriate to administer an antihypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the compound of formula (I) with: (a) statin and/or other lipid lowering drugs for example MTP inhibitors and LDLR upregulators; (b) antidiabetic agents, e.g. metformin, sulfonylureas, or PPAR-gamma, PPAR-alpha and PPAR-alpha/gamma modulators (for example thiazolidinediones such as e.g. Pioglitazone and Rosiglitazone); and (c) antihypertensive agents such as angiotensin antagonists, e.g., telmisartan, calcium channel antagonists, e.g. lacidipine and ACE inhibitors, e.g., enalapril.

In any case, the multiple therapeutic agents (at least one of which is a compound of Formula I, described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

While it may be possible for the compounds of the subject invention to be administered as the raw chemical, it is also possible to present them as a pharmaceutical formulation. Accordingly, the subject invention provides a pharmaceutical formulation comprising a compound or a pharmaceutically acceptable salt, ester, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions of the present invention may be manufactured in a manner that is itself known, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual, ophthalmic, and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Alternately, one may administer the compound in a local rather than systemic manner, for example, via injection of the compound directly into an organ, often in a depot or sustained release formulation. Furthermore, one may administer the drug in a targeted drug delivery system, for example, in a liposome coated with organ-specific antibody. The liposomes will be targeted to and taken up selectively by the organ. Topical formulations provided for local delivery include, but are not limited to, gels, creams, ointments, sprays, salves, and patches.

For intravenous injections, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For other parenteral injections, the agents of the invention may be formulated in aqueous or nonaqueous solutions, preferably with physiologically compatible buffers or excipients. Such excipients are generally known in the art.

For oral administration, the compounds can be formulated readily by combining the active compounds with pharmaceutically acceptable carriers or excipients well known in the art. Such carriers enable the compounds of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more compound of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starcH, wheat starcH, rice starcH, potato starcH, gelatin, gum tragacantH, methylcellulose, microcrystalline cellulose, hydroxypropylmethylcellulose, sodium carboxymethyl cellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. All formulations for oral administration should be in dosages suitable for such administration.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

The compounds may also be formulated in rectal compositions such as suppositories or retention enemas, e.g., containing conventional suppository bases such as cocoa butter, polyethylene glycol, or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

One example of a pharmaceutical carrier for the hydrophobic compounds of the invention is a cosolvent system comprising benzyl alcohol, a nonpolar surfactant, a water-miscible organic polymer, and an aqueous phase. The cosolvent system may be a 10% ethanol, 10% polyethylene glycol 300, 10% polyethylene glycol 40 castor oil (PEG40 castor oil) with 70% aqueous solution. This cosolvent system dissolves hydrophobic compounds well, and itself produces low toxicity upon systemic administration. Naturally, the proportions of a cosolvent system may be varied considerably without destroying its solubility and toxicity characteristics. Furthermore, the identity of the cosolvent components may be varied: for example, other low-toxicity nonpolar surfactants may be used instead of PEG-40 castor oil, the fraction size of polyethylene glycol 300 may be varied; other biocompatible polymers may replace polyethylene glycol, e.g., polyvinyl pyrrolidone; and other sugars or polysaccharides maybe included in the aqueous solution.

Alternatively, other delivery systems for hydrophobic pharmaceutical compounds may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Besides being useful for human treatment, these compounds are also useful for veterinary treatment of companion animals, exotic animals and farm animals, including mammals, rodents, and the like. More preferred animals include horses, dogs, and cats.

Many of the compounds of the invention may be provided as salts with pharmaceutically compatible counterions. Acid addition salts can be obtained by contacting the neutral form of such compounds with a sufficient amount of the desired acid, either neat or in a suitable inert solvent. Examples of pharmaceutically acceptable acid addition salts include, but are not limited to: those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like; as well as the salts derived from relatively nontoxic organic acids like acetic; propionic; isobutyric; lactic; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids like glucuronic or galactunoric acids and the like (see, for example, Berge et al. J. Pharm. Sci. 66:1-19 (1977)). Salts tend to be more soluble in aqueous or other protonic solvents than are the corresponding free acid or base forms. Salts useful with the compounds of the present invention include, without limitation, calcium, sodium, potassium, magnesium, hydrochloride, phosphate, sulfate, and p-toluenesulfonate salts. The salts can be prepared by contacting the compounds of the invention with an appropriate acid, either neat or in a suitable inert solvent, to yield the salt forms of the invention. In preferred embodiments, the p-toluenesulfonate (tosylate) is used with the disclosed compounds.

For example, 4-[4-(4-trifluoromethyl-pyridin-2-yl)-piperazine-1-sulfonyl]-indan-2-carboxylic acid prepared by any method can be contacted with a reagent selected from the group consisting of calcium acetate, hydrochloric acid, phosphoric acid, sulfuric acid, sodium hydroxide, potassium hydroxide, magnesium acetate, and p-toluenesulfonic acid, preferably in a 1:1 ratio, in a suitable solvent. Such solvents include but are not limited to diisopropyl ether, toluene, dichloromethane, and acetonitrile. Any technique known in the art can be used to vary conditions to induce precipitation or crystallization, including, without limitation: stirring for varying lengths of time at varying ambient conditions, the addition of hexanes or diethyl ether, evaporation, and reduction of temperature. In particular, 4-[4-(4-trifluoromethyl-pyridin-2-yl)-piperazine-1-sulfonyl]-indan-2-carboxylic acid can be contacted with p-toluenesulfonic acid to yield the tosylate salt form of the invention, to form 4-[4-(4-trifluoromethyl-pyridin-2-yl)-piperazine-1-sulfonyl]-indan-2-carboxylic acid p-toluenesulfonate salt. The present invention provides for 4-[cis-2,6-dimethyl-4-(4-trifluoromethoxy-phenyl)-piperazine-1-sulfonyl]-indan-2-carboxylic acid p-toluenesulfonate salt. The present invention provides for 4-[4-(4-trifluoromethyl-pyridin-2-yl)-piperazine-1-sulfonyl]-indan-2-carboxylic acid p-toluenesulfonate salt. Additionally, the present invention provides for pharmaceutical compositions comprising a salt of a compound of Formula I together with a pharmaceutically acceptable diluent or carrier.

All references, patents or applications, U.S. or foreign, cited in the application are hereby incorporated by reference as if written herein.

The following schemes can be used to practice the present invention.

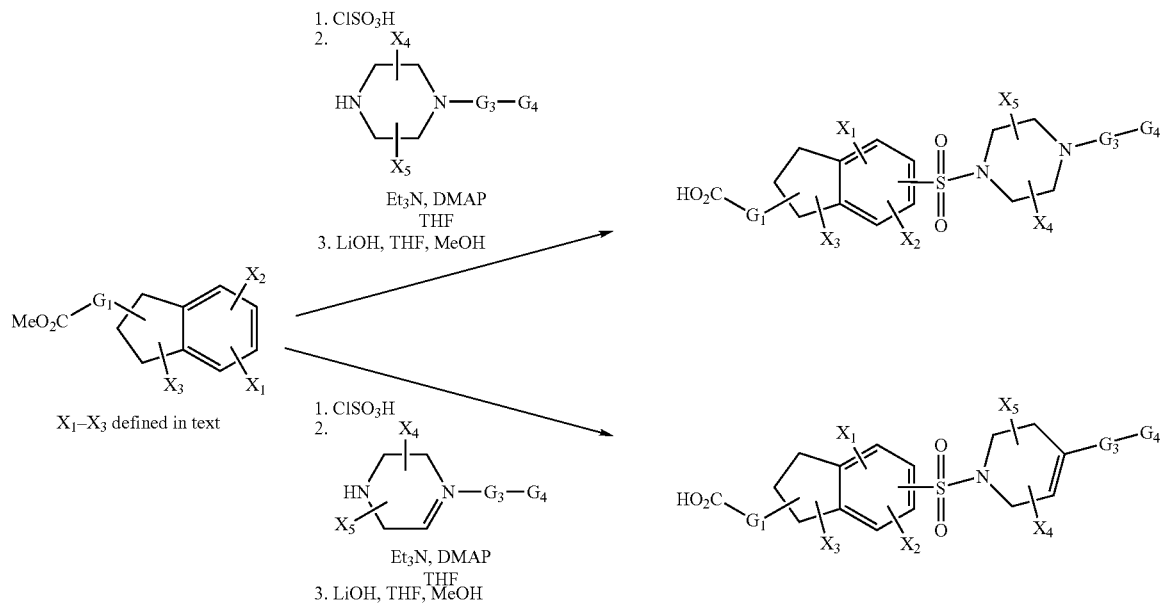

Various indane-carboxylic acids were prepared starting from their corresponding indanyl-2-acetic acid, indan-2-carboxylic acid, indan-1-carboxylic acid or 6-methoxy indan-1-acetic acid ester head group. The indane was first chlorosulfonylated with neat chlorosulfonic acid. Sulfonamide formation was induced by reaction with the appropriate piperazine or piperidine either at room temperature or at elevated temperatures when sterically hindered piperazines were used. Finally, base hydrolysis of the ester moiety was accomplished using lithium hydroxide.

Scheme II

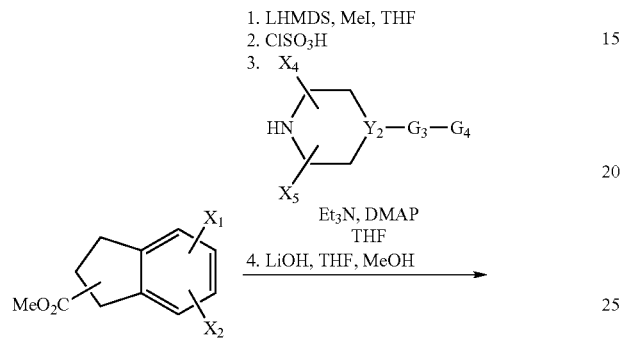

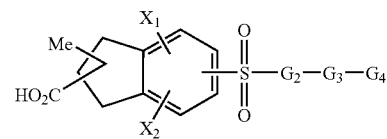

The methylated indan-carboxylic acids were synthesized in a similar manner with the addition of an initial α-methylation using LHMDS and methyl iodide (Scheme II).

Scheme III

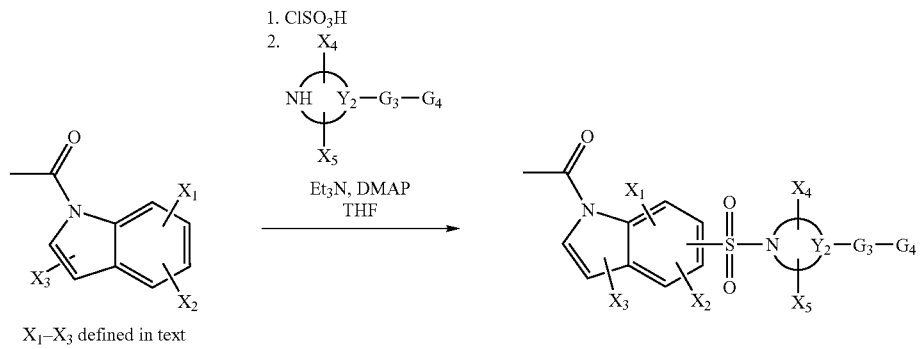

$X_1$–$X_3$ defined in text

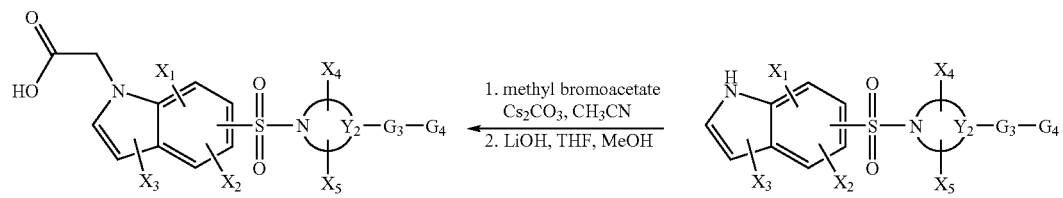

Scheme III outlines the synthesis of indol-1-yl embodiments of the present invention. A 1-(2,3-dihydro-indol-1-yl)-ethanone was first chlorosulfonylated using chlorosulfonic acid, followed by sulfonamide formation by reaction with the appropriate piperazine or piperidine. The indole was then accessed by first removal of the acetyl protecting group under acidic conditions, followed by DDQ oxidation of the indoline. The indole is then N-alkylated with methyl bromoacetate and further hydrolyzed with lithium hydroxide to provide the desired carboxylic acid.

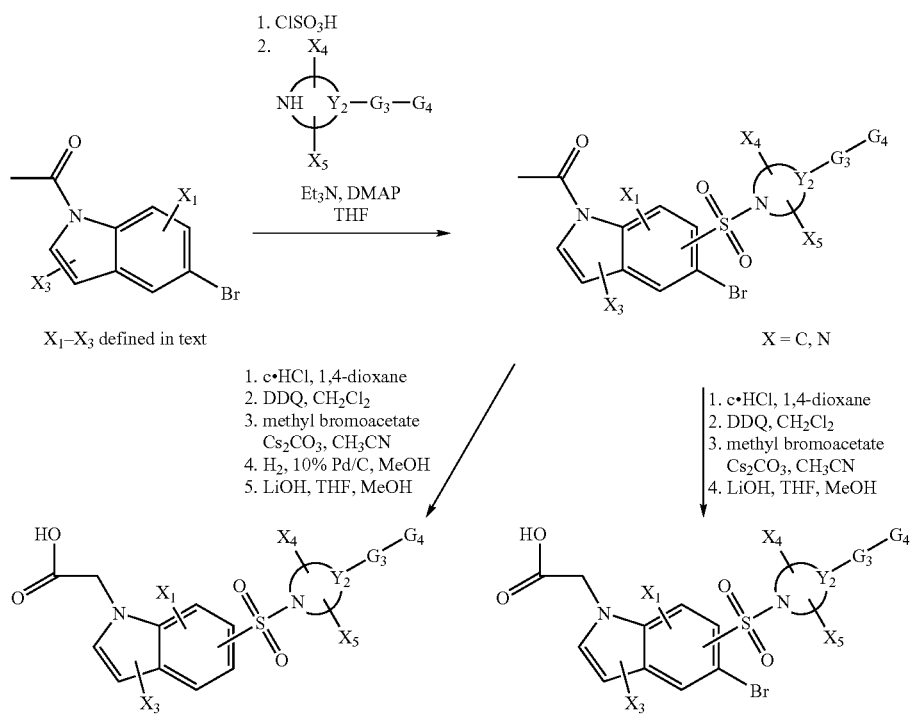

The compounds in Scheme IV show a sulfonamide substituted at the 6-position of the indole. Access to the 6-sulfonamide-5-bromo indoles begins with chlorosulfonylation of 1-(5-Bromo-2,3-dihydro-indol-1-yl)-ethanone, followed by sulfonamide formation with the appropriate piperazine or piperidine. The acetyl protecting group is then removed with conc. HCl in 1,4-dioxane, followed by DDQ oxidation yielding the indole head group. The indole is N-alkylated with methyl bromoacetate, followed by hydrolysis of the ester with lithium hydroxide. In turn, the 6-sulfonamide-indoles can be accessed by hydrogenation of the 5-bromo functionality before the hydrolysis step using catalytic hydrogenation with 10% Pd/C under a hydrogen atmosphere.

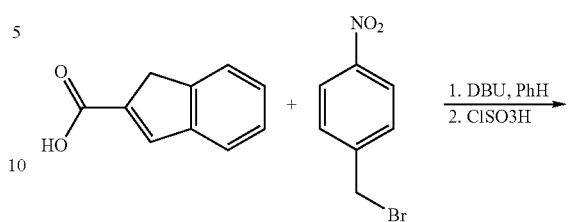

-continued

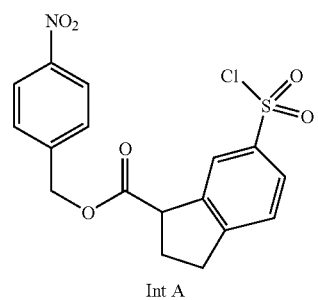

Int A

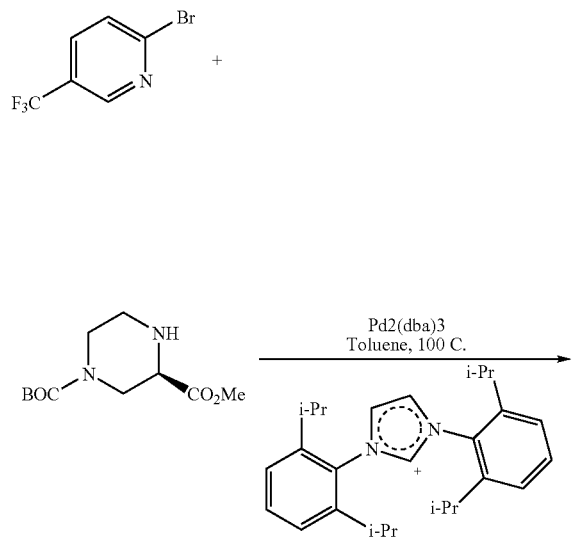
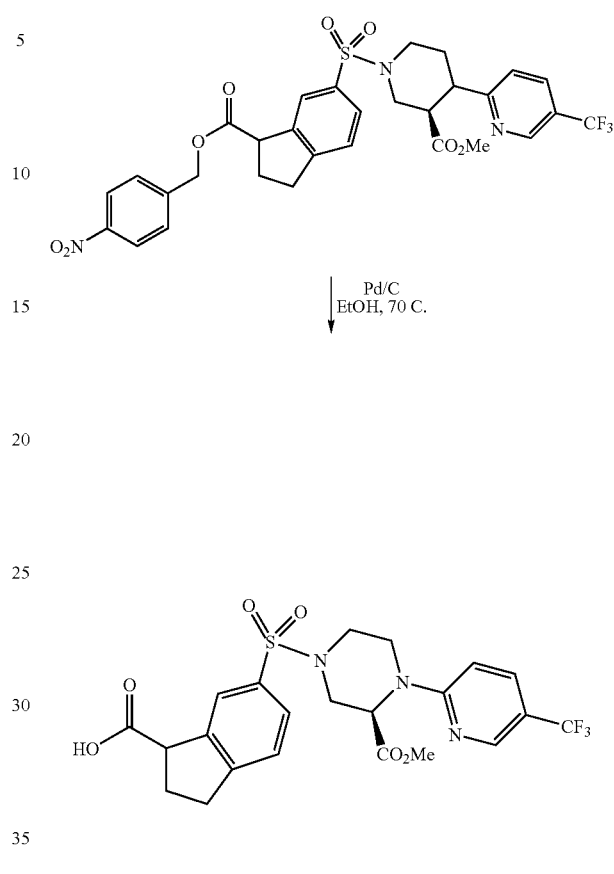
Scheme VI
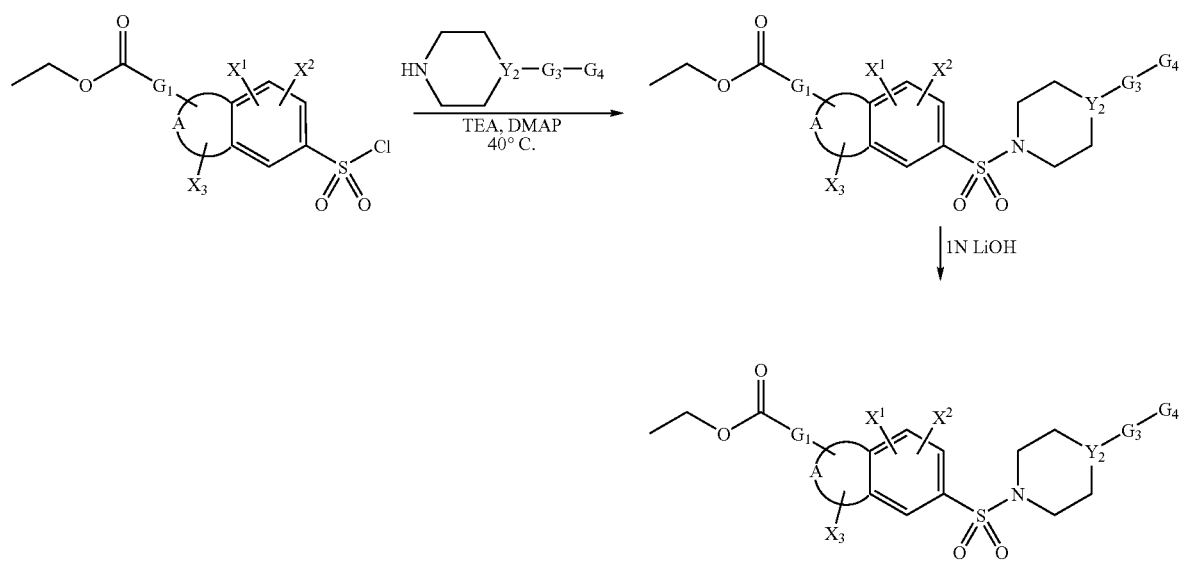

Scheme VI depicts a general method for coupling $G_2$-$G_4$ moieties to intermediate embodiments of the present invention and a general method for hydrolytically cleaving acid-protected intermediates to produce embodiments of the present invention.

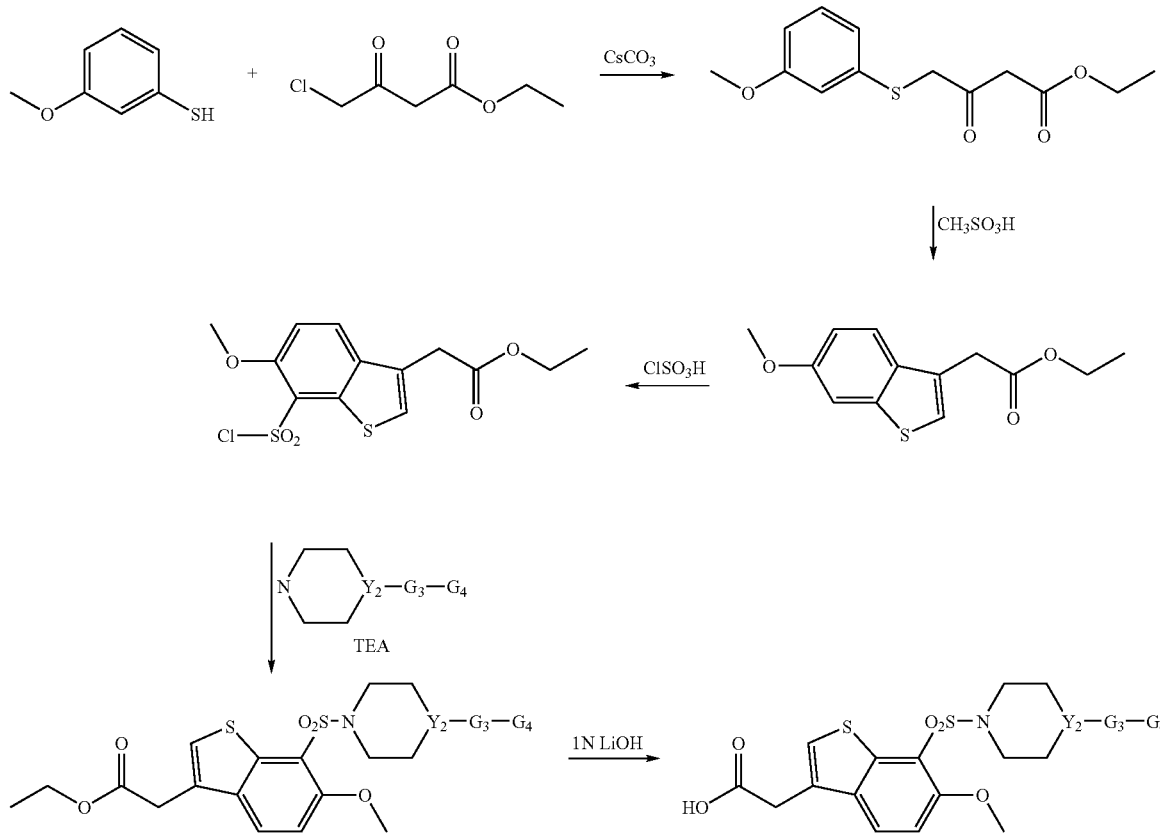

Scheme VII depicts a general method for preparing 6-methoxy benzthiophene embodiments of the present invention.

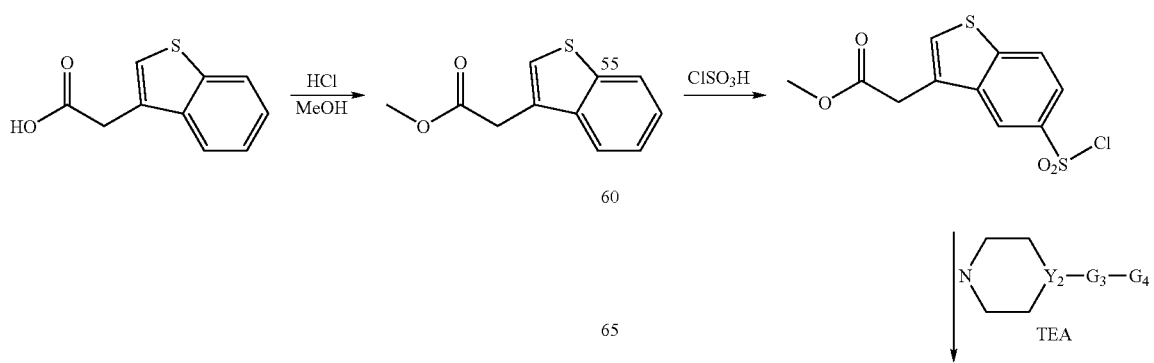

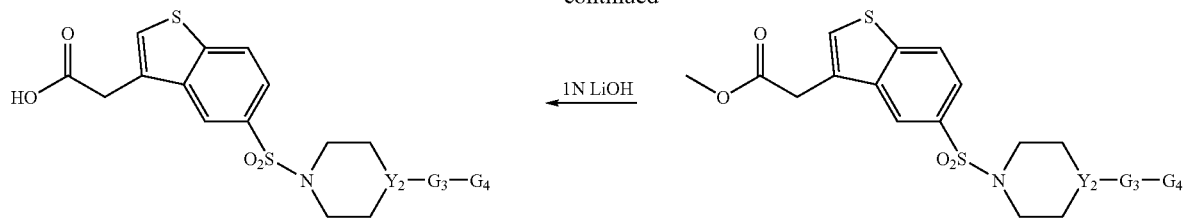

-continued

1N LiOH

Scheme VIII depicts a general method for preparing benzothiophene embodiments of the present invention. Several schemes present a general method for preparing a sulfonamide bond using a sulfonyl electrophile and a nitrogen nucleophile. In this way, a wide variety of $G_2$-$G_3$-$G_4$ groups may be introduced in a modular way.

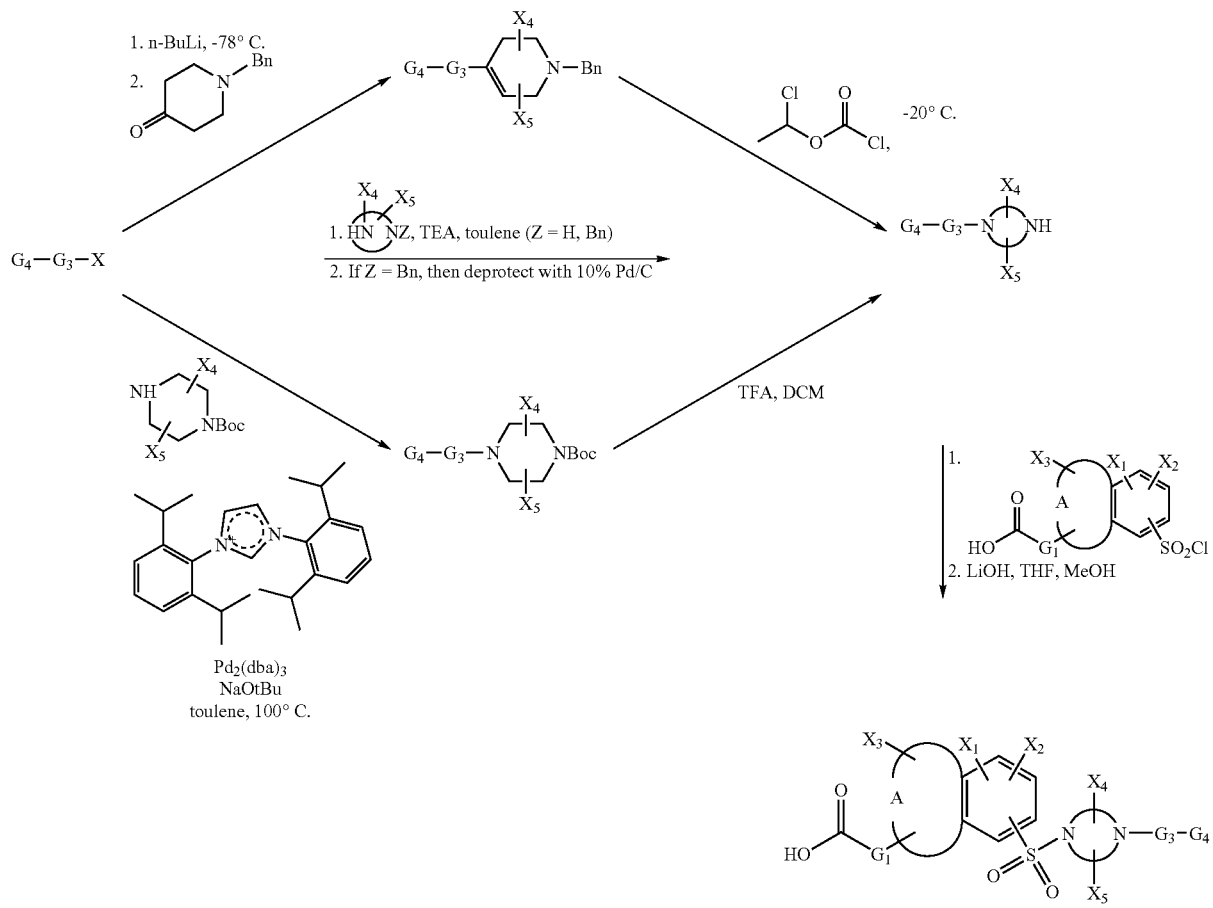

Scheme IX outlines the synthesis of various $G_2$-$G_3$-$G_4$ moieties starting from coupling the halogenated aryl $G_4$ groups with the appropriate piperazine or piperidine. Sulfonamide formation was induced by reaction with the chlorosulfonylated indane-carboxylic acid ester head groups (see Scheme I). Finally, base hydrolysis of the ester moiety was accomplished using lithium hydroxide.

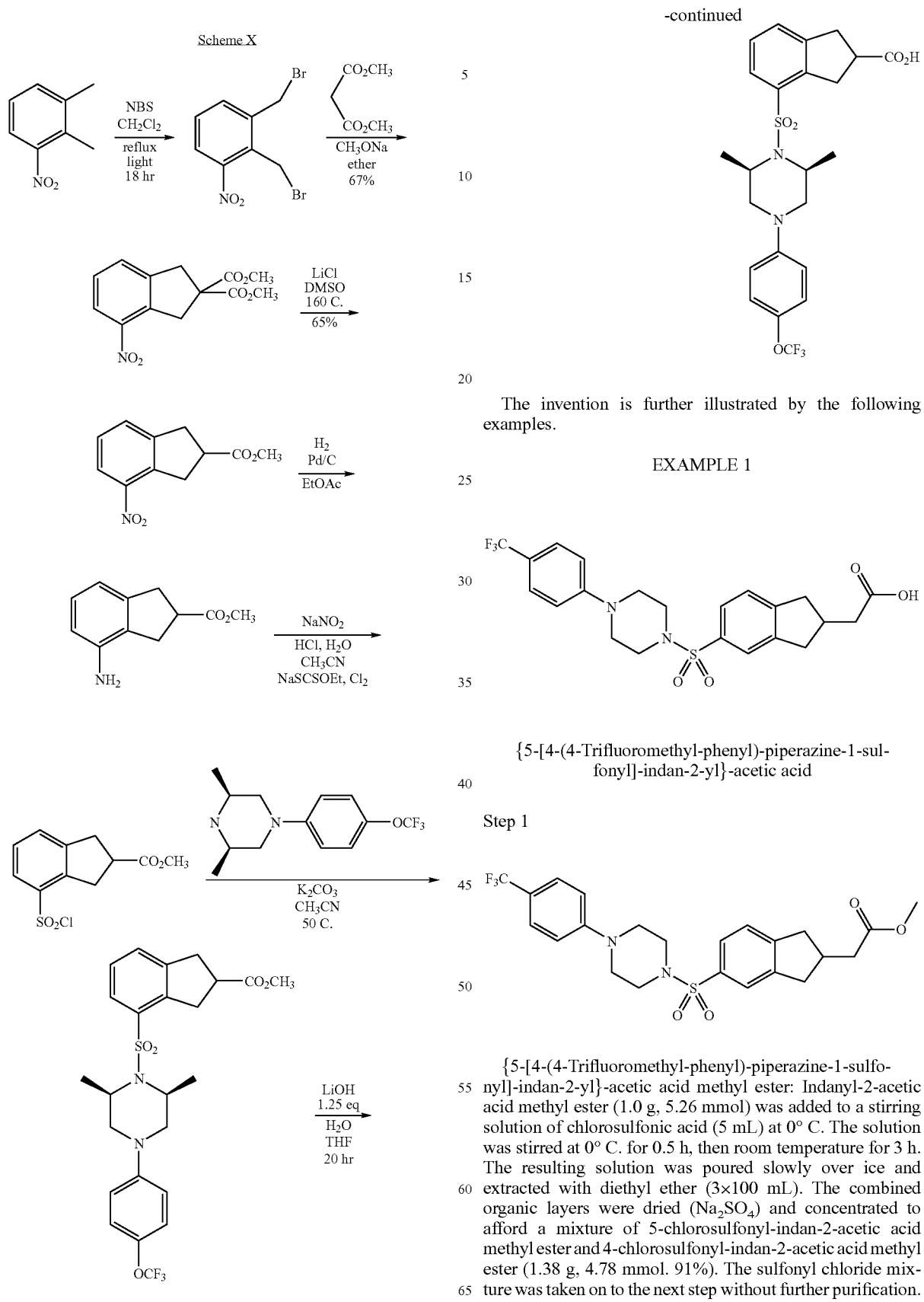

The invention is further illustrated by the following examples.

EXAMPLE 1

{5-[4-(4-Trifluoromethyl-phenyl)-piperazine-1-sulfonyl]-indan-2-yl}-acetic acid

Step 1

{5-[4-(4-Trifluoromethyl-phenyl)-piperazine-1-sulfonyl]-indan-2-yl}-acetic acid methyl ester: Indanyl-2-acetic acid methyl ester (1.0 g, 5.26 mmol) was added to a stirring solution of chlorosulfonic acid (5 mL) at 0° C. The solution was stirred at 0° C. for 0.5 h, then room temperature for 3 h. The resulting solution was poured slowly over ice and extracted with diethyl ether (3×100 mL). The combined organic layers were dried (Na$_2$SO$_4$) and concentrated to afford a mixture of 5-chlorosulfonyl-indan-2-acetic acid methyl ester and 4-chlorosulfonyl-indan-2-acetic acid methyl ester (1.38 g, 4.78 mmol. 91%). The sulfonyl chloride mixture was taken on to the next step without further purification. The mixture of sulfonyl chlorides (370 mg, 1.28 mmol) were dissolved in dry THF (10 mL). To this solution was added 1-(4-trifluoromethylphenyl)piperazine (315 mg, 1.37 mmol), triethylamine (600 μL, 4.3 mmol) and DMAP (catalytic amount). The reaction was stirred at room temperature for 1 h, concentrated and directly purified by silica gel flash column chromatography to separate the regioisomers (25% ethyl acetate in hexanes) affording {5-[4-(4-trifluoromethyl-phenyl)-piperazine-1-sulfonyl]-indan-2-yl}-acetic acid methyl ester (118 mg, 19%) and {4-[4-(4-trifluoromethyl-phenyl)-piperazine-1-sulfonyl]-indan-2-yl}-acetic acid methyl ester (40 mg, 6%) as clear colorless oils. {5-[4-(4-trifluoromethyl-phenyl)-piperazine-1-sulfonyl]-indan-2-yl}-acetic acid methyl ester: $^1$H NMR (400 MHz, CDCl$_3$) δ7.57 (s, 1H), 7.56 (d, 1H), 7.45 (d, 2H), 7.33 (d, 1H), 6.87 (d, 2H), 3.69 (s, 3H), 3.33 (m, 4H), 3.21 (dd, 2H), 3.14 (m, 4H), 2.95 (m, 1H), 2.71 (dd, 2H), 2.52 (d, 2H).

Step 2

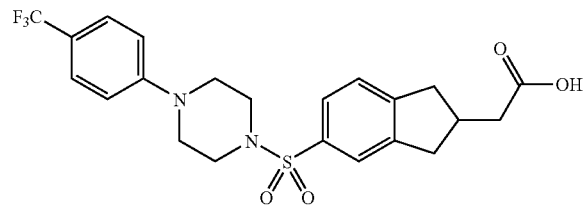

{5-[4-(4-Trifluoromethyl-phenyl)-piperazine-1-sulfonyl]-indan-2-yl}-acetic acid: {5-[4-(4-Trifluoromethyl-phenyl)-piperazine-1-sulfonyl]-indan-2-yl}-acetic acid methyl ester (118 mg, 0.245 mmol) was dissolved in THF (10 mL). To this solution was added 1M LiOH (5 mL) and was stirred at room temperature for 3 h. TLC indicated that the reaction was complete. The reaction mixture was then quenched with Dowex 50WX4-50 until neutral and then filtered to afford pure {5-[4-(4-trifluoromethyl-phenyl)-piperazine-1-sulfonyl]-indan-2-yl}-acetic acid (112 mg, 98%) as a white solid. The product can be further purified by silica gel flash column chromatography (dichloromethane/MeOH/AcOH 95:5:0.1). $^1$H NMR (400 MHz, MeOH-d$_4$) δ7.60 (s, 1H), 7.56 (d, 1H), 7.45 (d, 2H), 7.41 (d, 1H), 7.00 (d, 2H), 3.32 (m, 4H), 3.22 (m, 2H), 3.17 (m, 4H), 2.88 (m, 1H), 2.72 (m, 2H), 2.47 (d, 2H); LCMS: 468.8 (M+1)$^+$.

EXAMPLE 2

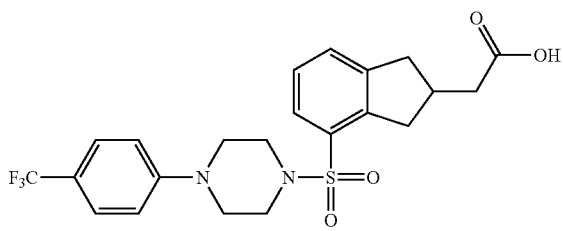

{4-[4-(4-Trifluoromethyl-phenyl)-piperazine-1-sulfonyl]-indan-2-yl}-acetic acid: The compound {4-[4-(4-trifluoromethyl-phenyl)-piperazine-1-sulfonyl]-indan-2-yl}-acetic acid was synthesized according to the procedure from Example 1 using {4-[4-(4-trifluoromethyl-phenyl)-piperazine-1-sulfonyl]-indan-2-yl}-acetic acid methyl ester from Example 1, Step 1. $^1$H NMR (400 MHz, MeOH-d$_4$) δ7.60 (d, 1H), 7.52 (d, 2H), 7.51 (d, 1H), 7.31 (t, 1H), 7.15 (d, 2H), 3.53 (dd, 1H), 3.42 (m, 4H), 3.25 (m, 4H), 3.20 (m, 1H), 3.00 (dd, 1H), 2.87 (m, 1H), 2.72 (m, 1H), 2.47 (m, 2H); LCMS: 468.8 (M+1)$^+$.

EXAMPLE 3

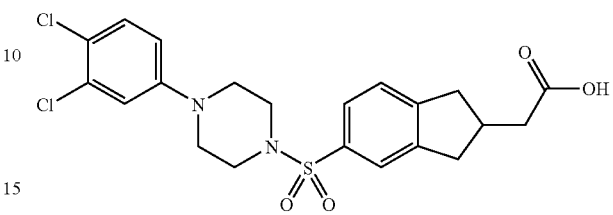

{5-[4-(3,4-Dichlorophenyl)-piperazine-1-sulfonyl]-indan-2-yl}-acetic acid: The compound {5-[4-(3,4-dichlorophenyl)-piperazine-1-sulfonyl]-indan-2-yl}-acetic acid was synthesized according to the procedure from Example 1 using 3,4-(dichlorophenyl)-piperazine. $^1$H NMR (400 MHz, MeOH-d$_4$) δ7.60 (s, 1H), 7.56 (d, 1H), 7.42 (d, 1H), 7.29 (d, 1H), 7.04 (d, 1H), 6.83 (dd, 1H), 3.31 (m, 2H), 3.23 (m, 4H), 3.18 (m, 1H), 3.08 (m, 3H), 2.90 (m, 1H), 2.74 (m, 2H), 2.46 (d, 2H); LCMS: 468.8 (M+1)$^+$.

EXAMPLE 4

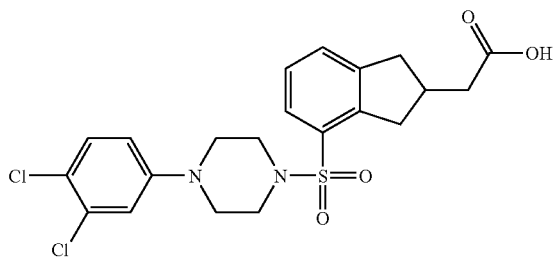

{4-[4-(3,4-Dichlorophenyl)-piperazine-1-sulfonyl]-indan-2-yl}-acetic acid: The compound {4-[4-(3,4-dichlorophenyl)-piperazine-1-sulfonyl]-indan-2-yl}-acetic acid was synthesized according to the procedure from Example 1 using 3,4-(dichlorophenyl)-piperazine. $^1$H NMR (400 MHz, MeOH-d$_4$) δ7.59 (d, 1H), 7.52 (d, 1H), 7.38 (dd, 1H), 7.29 (d, 1H), 7.04 (d, 1H), 6.85 (dd, 1H), 3.50 (dd, 1H), 3.20 (m, 8H), 2.98 (dd, 1H), 2.86 (m, 1H), 2.72 (dd, 1H), 2.48 (m, 1H), 2.18 (m, 2H); LCMS: 468.9 (M+1)$^+$.

EXAMPLE 5

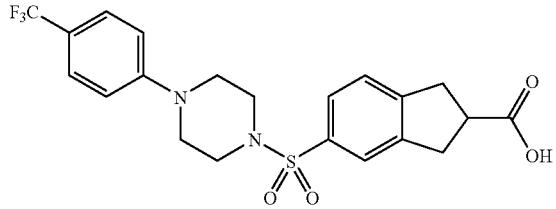

5-[4-(4-Trifluoromethyl-phenyl)-piperazine-1-sulfonyl]-indan-2-carboxylic acid: The compound 5-[4-(4-trifluoromethyl-phenyl)-piperazine-1-sulfonyl]-indan-2-carboxylic acid was synthesized according to the procedure outlined in Example 1 using indane-2-carboxylic acid methyl ester. $^1$H NMR (400 MHz, MeOH-d$_4$) δ 7.64 (s, 1H), 7.60 (d, 1H), 7.46 (d, 2H), 7.46 (m, 1H), 7.01 (d, 2H), 3.41 (m, 1H), 3.30 (m, 8H), 3.10 (m, 4H).

EXAMPLE 6

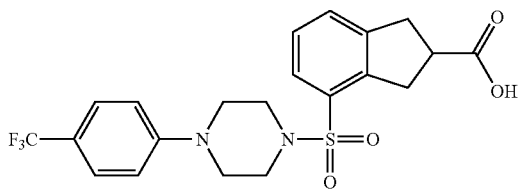

4-[4-(4-Trifluoromethyl-phenyl)-piperazine-1-sulfonyl]-indan-2-carboxylic acid: The compound 4-[4-(4-trifluoromethyl-phenyl)-piperazine-1-sulfonyl]-indan-2-carboxylic acid was synthesized according to the procedure outlined in Example 1 using indane-2-carboxylic acid methyl ester. $^1$H NMR (400 MHz, MeOH-d$_4$) δ 7.63 (d, 1H), 7.53 (d, 1H), 7.46 (d, 2H), 7.40 (t, 1H), 7.03 (d, 2H), 3.58-3.56 (m, 2H), 3.42-3.34 (m, 5H), 3.32-3.18 (m, 6H); LCMS: 455.0 (M+1)$^+$.

EXAMPLE 7

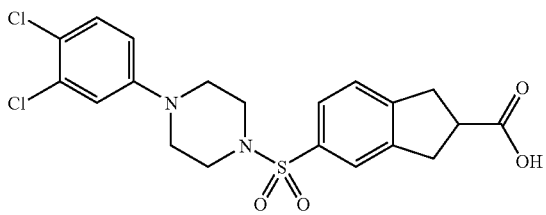

5-[4-(3,4-Dichlorophenyl)-piperazine-1-sulfonyl]-indan-2-carboxylic acid: The compound 5-[4-(3,4-dichlorophenyl)-piperazine-1-sulfonyl]-indan-2-carboxylic acid was synthesized according to the procedure outlined in Example 1 using indane-2-carboxylic acid methyl ester and 3,4-(dichlorophenyl)-piperazine. $^1$H NMR (400 MHz, MeOH-d$_4$) δ 7.61 (s, 1H), 7.56 (d, 1H), 7.42 (d, 1H), 7.28 (d, 1H), 7.03 (d, 1H), 6.89 (dd, 1H), 3.30 (m, 1H), 3.28 (m, 4H), 3.32 (m, 4H), 3.08 (m, 4H).

EXAMPLE 8

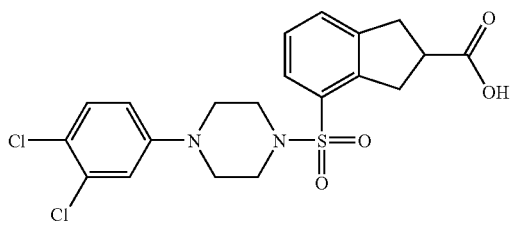

4-[4-(3,4-Dichlorophenyl)-piperazine-1-sulfonyl]-indan-2-carboxylic acid: The compound 4-[4-(3,4-dichlorophenyl)-piperazine-1-sulfonyl]-indan-2-carboxylic acid was synthesized according to the procedure outlined in Example 1 using indane-2-carboxylic acid methyl ester and 3,4-(dichlorophenyl)-piperazine. $^1$H NMR (400 MHz, MeOH-d$_4$) δ 7.62 (d, 1H), 7.54 (d, 1H), 7.40 (t, 1H), 7.30 (d, 1H), 7.06 (d, 1H), 6.86 (dd, 1H), 3.57-3.55 (m, 2H), 3.42-3.34 (m, 1H), 3.32-3.29 (m, 2H), 3.26-3.16 (m, 8H); LCMS: 454.9 (M+1)$^+$.

EXAMPLE 9

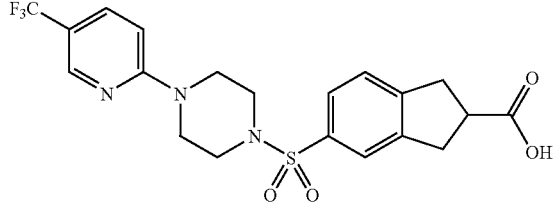

5-[4-(4-Trifluoromethyl-pyridin-2-yl)-piperazine-1-sulfonyl]-indan-2-carboxylic acid: The compound 5-[4-(3,4-trifluoromethyl-pyridin-2-yl)-piperazine-1-sulfonyl]-indan-2-carboxylic acid was synthesized according to the procedure outlined in Example 1 using indane-2-carboxylic acid methyl ester and 1-[5-(trifluoromethyl)-pyrid-2-yl]-piperazine. $^1$H NMR (400 MHz, MeOH-d$_4$) δ 8.01 (s, 1H), 7.69 (d, 1H), 7.61 (s, 1H), 7.56 (d, 1H), 7.41 (d, 1H), 6.85 (d, 1H), 3.75 (m, 3H), 3.32 (m, 1H), 3.31 (m, 3H), 3.28 (m, 3H), 3.05 (m, 3H); LCMS: 455.9 (M+1)$^+$.

EXAMPLE 10

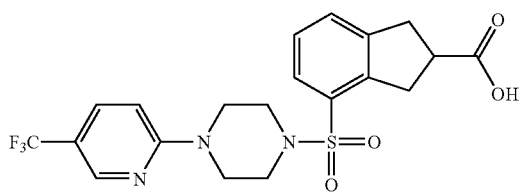

4-[4-(4-Trifluoromethyl-pyridin-2-yl)-piperazine-1-sulfonyl]-indan-2-carboxylic acid: The compound 4-[4-(4-trifluoromethyl-pyridin-2-yl)-piperazine-1-sulfonyl]-indan-2-carboxylic acid was synthesized according to the procedure outlined in Example 1 using indane-2-carboxylic acid methyl ester and 1-[5-(trifluoromethyl)-pyrid-2-yl]-piperazine. $^1$H NMR (400 MHz, MeOH-D$_4$) δ 8.35 (s, 1H), 7.74 (d, 1H), 7.65 (d, 1H), 7.55 (d, 1H), 7.42 (t, 1H), 6.90 (d: 1H), 3.78 (m, 4H), 3.59 (d, 2H), 3.41 (m, 1H), 3.34 (m, 2H), 3.20 (m, 4H); LCMS: 456.0 (M+1)$^+$.

EXAMPLE 11

This single enantiomer of Example 10 was obtained by chiral HPLC (chiralpak ADH 0.46×15 cm Hex/IPA 94:6 (v/v) with 0.1% TFA, flow rate 1 mL/min) separation from the racemate.

EXAMPLE 12

This single enantiomer of Example 10 was obtained by chiral HPLC (chiralpak ADH 0.46×15 cm Hex/IPA 94:6 (v/v) with 0.1% TFA, flow rate 1 ml/min) separation from the racemate.

EXAMPLE 13

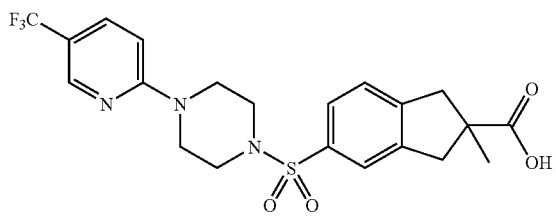

2-Methyl-5-[4-(5-trifluoromethyl-pyridin-2-yl)-piperazine-1-sulfonyl]-indan-2-carboxylic acid Step 1

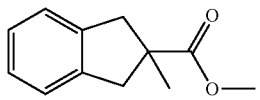

2-Methyl-indan-2-carboxylic acid methyl ester: Indane-2-carboxylic acid methyl ester (550 mg, 3.125 mmol) was dissolved in THF (20 mL). At −78° C. LiHMDS (1M solution in THF, 3.75 mL) was added into the reaction mixture. The solution was stirred for 15 min at −78° C., warmed to 0° C. for 15 min and then −78° C. for an additional 15 min. Methyl iodide (250 µL, 4.01 mmol) was then added into the reaction mixture followed by stirring at −78° C. for 15 min, room temperature for 30 min and then quenched with saturated ammonium chloride. The solution was then diluted with diethyl ether and washed with saturated sodium bicarbonate, brine, dried (MgSO$_4$), filtered and concentrated. The crude mixture was then purified by silica gel flash column chromatography to afford 2-methyl-indan-2-carboxylic acid methyl ester (52 mg, 9%) as a white solid. $^1$H NMR (400 MHz, CDCl$_3$) δ 7.16 (m, 4H), 3.72 (t, 3H), 3.48 (d, 2H), 2.81 (d, 2H), 1.36 (s, 3H).

Step 2

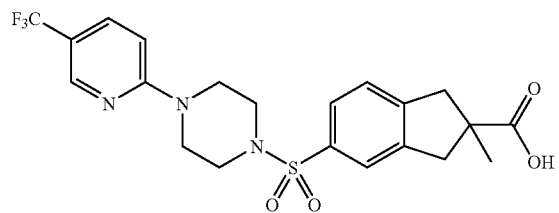

2-Methyl-5-[4-(5-trifluoromethyl-pyridin-2-yl)-piperazine-1-sulfonyl]-indan-2-carboxylic acid: The compound 2-methyl-5-[4-(5-trifluoromethyl-pyridin-2-yl)-piperazine-1-sulfonyl]-indan-2-carboxylic acid was synthesized according to the procedure outlined in Example 1 using 1-[5-(trifluoromethyl)-pyrid-2-yl]-piperazine and 2-methyl-indan-2-carboxylic acid methyl ester to afford 2-methyl-5-[4-(5-trifluoromethyl-pyridin-2-yl)-piperazine-1-sulfonyl]-indan-2-carboxylic acid. $^1$H NMR (400 MHz, MeOH-d$_4$) δ 8.30 (s, 1H), 7.70 (dd, 1H), 7.61 (s, 1H), 7.58 (d, 1H), 7.41 (d, 1H), 6.86 (d, 1H), 3.74 (s, 4H), 3.50 (dd, 2H), 3.06 (m, 4H), 2.90 (dd, 2H), 1.35 (s, 3H); LCMS: 470.5 (M+1)$^+$.

EXAMPLE 14

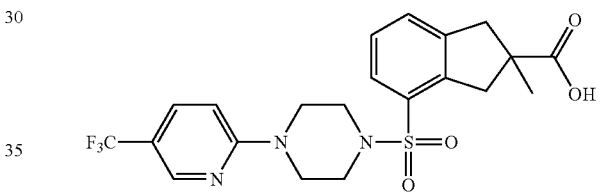

2-Methyl-4-[4-(5-trifluoromethyl-pyridin-2-yl)-piperazine-1-sulfonyl]-indan-2-carboxylic acid: The compound 2-methyl-4-[4-(5-trifluoromethyl-pyridin-2-yl)-piperazine-1-sulfonyl]-indan-2-carboxylic acid was synthesized according to the procedure outlined in Example 13. $^1$H NMR (400 MHz, MeOH-d$_4$) δ 8.32 (s, 1H), 7.74 (dd, 1H), 7.61 (d, 1H), 7.50 (d, 1H), 7.39 (t, 1H), 6.92 (d, 1H), 3.90 (m, 1H), 3.75 (m, 5H), 3.50 (d, 1H), 3.19 (m, 4H), 2.91 (d, 1H), 1.40 (s, 3H); LCMS: 470.0 (M+1)$^+$.

EXAMPLE 15

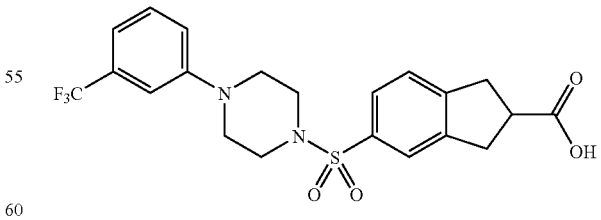

5-[4-(3-Trifluoromethyl-phenyl)-piperazine-1-sulfonyl]-indan-2-carboxylic acid: The compound 5-[4-(3-trifluoromethyl-phenyl)-piperazine-1-sulfonyl]-indan-2-carboxylic acid was synthesized according to the procedure outlined in Example 1 using indane-2-carboxylic acid methyl ester and 1-(3-trifluoromethylphenyl)-piperazine. $^1$H NMR (400 MHz, MeOH-d$_4$) $\delta$7.65 (s, 1H), 7.60 (d, 1H), 7.45 (d, 1H), 7.38 (t, 1H), 7.15 (d, 1H), 7.08 (d, 1H), 3.41 (m, 1H), 3.30 (m, 8H), 3.11 (m, 4H).

EXAMPLE 16

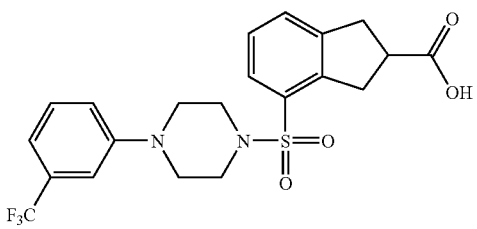

4-[4-(3-Trifluoromethyl-phenyl)-piperazine-1-sulfonyl]-indan-2-carboxylic acid: The compound 4-[4-(3-trifluoromethyl-phenyl)-piperazine-1-sulfonyl]-indan-2-carboxylic acid was synthesized according to the procedure outlined in Example 1 using indane-2-carboxylic acid methyl ester and 1-(3-trifluoromethylphenyl)-piperazine. $^1$H NMR (400 MHz, MeOH-d$_4$) $\delta$7.62 (d, 1H), 7.53 (d, 1H), 7.39 (dd, 1H), 7.40 (m, 1H), 7.16 (d, 1H), 7.16 (s, 1H), 7.09 (d, 1H), 3.57 (m, 2H), 3.36 (m, 1H), 3.30 (m, 6H), 3.23 (m, 4H).

EXAMPLE 17

5-[4-(4-Trifluoromethyl-phenyl)-3,6-dihydro-2H-pyridine-1-sulfonyl]-indan-2-carboxylic acid

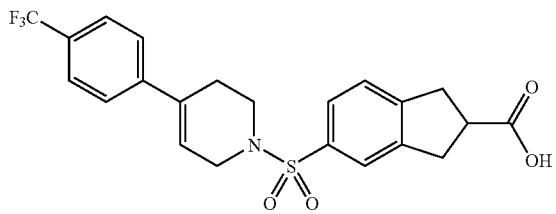

Step 1

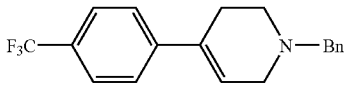

1-Benzyl-4-(4-trifluoromethyl-phenyl)-1,2,3,6-tetrahydro-pyridine: 4-Iodobenzo trifluoride (2.97 g, 10.92 mmol) in THF (50 mL) was added dropwise over 0.5 h to a solution of n-BuLi (7.5 ml, 1.6 M, 12 mmol) in THF (50 mL) at −78° C. The reaction mixture was stirred an additional 0.5 h upon which N-benzyl-4-piperidone (2.13 g, 11.69 mmol) in THF (10 mL) was added over 10 minutes. Stirring was continued for 0.5 h at −78° C., followed by room temperature overnight. The reaction was quenched with saturated ammonium chloride and the organic layer was separated. The aqueous layer was extracted with THF and the combined organic layers were dried (MgSO$_4$), filtered and concentrated to afford a brown oil. The crude product was then dissolved in conc. HCl (30 mL) and 1,4-dioxane (6 mL) and stirred at 100° C. overnight. The reaction was poured into saturated sodium bicarbonate and extracted with ethyl acetate (3×200 mL). The combined organic layers were dried (MgSO$_4$), filtered and concentrated. The product was purified by silica gel flash column chromatography (20% ethyl acetate in hexanes) to afford 1-benzyl-4-(4-trifluoromethyl-phenyl)-1,2,3,6-tetrahydro-pyridine (981 mg, 28%). $^1$H NMR (400 MHz, CDCl$_3$) $\delta$7.61 (d, 2H), 7.52 (d, 2H), 7.40 (m, 5H), 6.21 (m, 1H), 3.70 (s, 2H), 3.25 (q, 2H), 2.78 (t, 2H), 2.62 (m, 2H); LCMS: 318.4 (M+1)$^+$.

Step 2

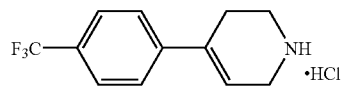

4-(4-Trifluoromethyl-phenyl)-1,2,3,6-tetrahydro-pyridine (HCl): 1-Benzyl-4-(4-trifluoromethyl-phenyl)-1,2,3,6-tetrahydro-pyridine was dissolved in THF (10 mL). The reaction was cooled to −20° C. and 1-chloroethylchloroformate (0.5 mL) in THF (2 ml) was added. The reaction was stirred at −10° C. for 3 h and then concentrated. MeOH (10 mL) was added to the crude mixture and refluxed for 2 h. The solvent was removed to provide 4-(4-trifluoromethyl-phenyl)-1,2,3,6-tetrahydro-pyridine (HCl) which was used without further purification. $^1$H NMR (400 MHz, DMSO-d$_6$) $\delta$9.40 (s, 2H), 7.74 (m, 4H), 6.39 (m, 1H), 3.79 (m, 2H), 3.33 (m, 2H), 2.74 (m, 2H).

Step 3

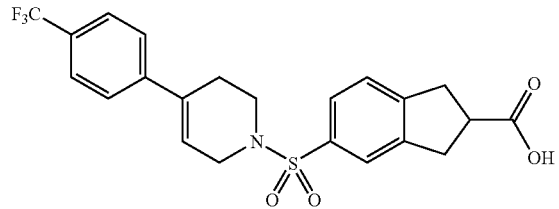

5-[4-(4-Trifluoromethyl-phenyl)-3,6-dihydro-2H-pyridine-1-sulfonyl]-indan-2-carboxylic acid: The compound 5-[4-(4-trifluoromethyl-phenyl)-3,6-dihydro-2H-pyridine-1-sulfonyl]-indan-2-carboxylic acid was prepared according to the procedure outlined in Example 1 using indane-2-carboxylic acid methyl ester and 4-(4-trifluoromethyl-phenyl)-1,2,3,6-tetrahydro-pyridine. $^1$H NMR (400 MHz, CDCl$_3$)

δ 7.66 (m, 2H), 7.57 (d, 2H), 7.39 (m, 3H), 6.06 (m, 1H), 3.79 (m, 2H), 3.50-3.26 (m, 7H), 2.63 (m, 2H); LCMS: 451.9 (M+1)+.

EXAMPLE 18

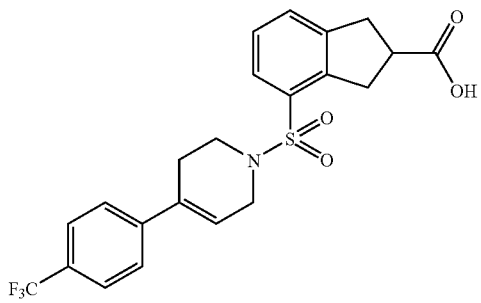

4-[4-(4-Trifluoromethyl-phenyl)-3,6-dihydro-2H-pyridine-1-sulfonyl]-indan-2-carboxylic acid: The compound 4-[4-(4-trifluoromethyl-phenyl)-3,6-dihydro-2H-pyridine-1-sulfonyl]-indan-2-carboxylic acid was prepared according to the procedure outlined in Example 17. $^1$H NMR (400 MHz, CDCl$_3$) δ 7.69 (d, 1H), 7.57 (d, 2H), 7.44 (d, 1H), 7.41 (d, 2H), 7.34 (t, 1H), 6.08 (m, 1H), 3.89 (m, 2H), 3.80-3.31 (m, 7H), 2.61 (m, 2H); LCMS: 451.9 (M+1)+.

EXAMPLE 19

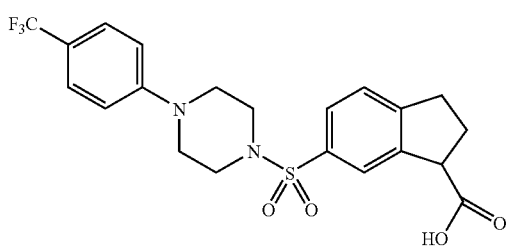

6-[4-(4-Trifluoromethyl-phenyl)-piperazine-1-sulfonyl]-indan-1-carboxylic acid: The compound 6-[4-(4-trifluoromethyl-phenyl)-piperazine-1-sulfonyl]-indan-1-carboxylic acid was prepared according to the procedure outlined in Example 1 using indane-1-carboxylic acid methyl ester. $^1$H NMR (400 MHz, DMSO-d$_6$) δ 12.71 (s, 1H), 7.75 (s, 1H), 7.65 (d, 1H), 7.57 (d, 1H), 7.53 (d, 2H), 7.06 (d, 2H), 4.17 (t, 1H), 3.40 (m, 4H), 3.03 (m, 6H), 2.36 (m, 2H); LCMS: 454.9 (M+1)+.

EXAMPLE 20

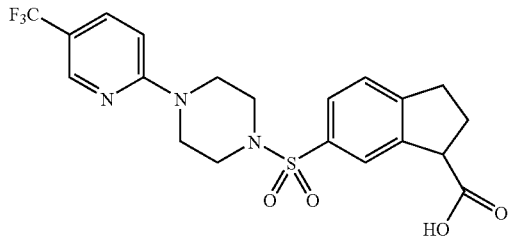

6-[4-(5-Trifluoromethyl-pyridin-2-yl)-piperazine-1-sulfonyl]-indan-1-carboxylic acid: The compound 6-[4-(5-trifluoromethyl-pyridin-2-yl)-piperazine-1-sulfonyl]-indan-1-carboxylic acid was prepared according to the procedure outlined in Example 1 using indane-1-carboxylic acid methyl ester and 1-[5-(trifluoromethyl)-pyrid-2-yl]-piperazine. $^1$H NMR (400 MHz, CDCl$_3$) δ 8.35 (s, 1H), 7.83 (s, 1H), 7.64 (dd, 1H), 7.61 (dd, 1H), 7.39 (d, 1H), 6.61 (d; 1H), 4.13 (t, 1H), 3.75 (m, 4H), 3.23-3.10 (m, 1H), 3.11 (m, 4H), 3.40-2.94 (m, 1H), 2.48 (m, 2H).

EXAMPLE 21

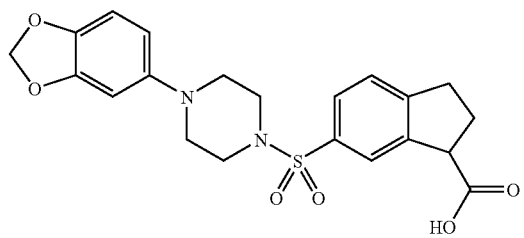

6-(4-Benzo[1,3]dioxol-5-yl-piperazine-1-sulfonyl)-indan-1-carboxylic acid: The compound 6-(4-Benzo[1,3]dioxol-5-yl-piperazine-1-sulfonyl)-indan-1-carboxylic acid was synthesized according to the procedure outlined in Example 1 using 1-(3,4-methylendioxybenzyl)piperazine and indane-1-carboxylic acid methyl ester. $^1$H NMR (400 MHz, MeOH-D$_4$) δ 7.77 (s, 1H) 7.60 (dd, 1H), 7.47 (d, 1H), 6.78 (s, 1H), 6.73 (m, 2H), 5.90 (s, 2H), 4.11 (t, 1H), 3.16-3.09 (m, 1H), 3.04-2.96 (m, 5H), 2.58-2.55 (m, 4H), 2.45-2.39 (m, 2H); LCMS.

EXAMPLE 22

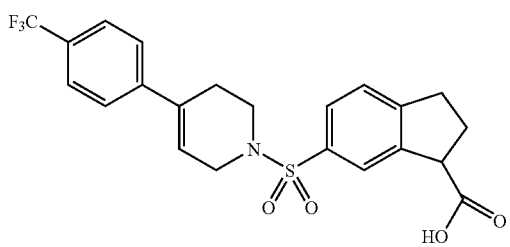

6-[4-(4-Trifluoromethyl-phenyl)-3,6-dihydro-2H-pyridine-1-sulfonyl]-indan-1-carboxylic acid: The compound 6-[4-(4-trifluoromethyl-phenyl)-3,6-dihydro-2H-pyridine-1-sulfonyl]-indan-1-carboxylic acid was synthesized according to the procedure outlined in Example 17 using indane-1-carboxylic acid methyl ester. $^1$H NMR (400 MHz, DMSO-d$_6$) δ12.72 (s, 1H), 7.80 (s, 1H), 7.73-7.69 (m, 3H), 7.61 (d, 2H), 7.55 (d, 1H), 6.28 (m, 1H), 4.16 (t, 1H), 3.72 (m, 2H), 3.26 (t, 2H), 3.12-2.92 (m, 2H), 2.62 (m, 2H), 2.36 (2H); LCMS: 451.9 (M+1)$^+$.

EXAMPLE 23

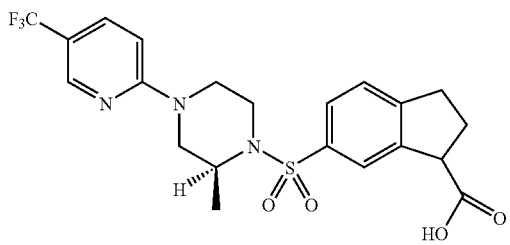

6-[2-(S)-methyl-4-(5-Trifluoromethyl-pyridin-2-yl)-piperazine-1-sulfonyl]-indan-1-carboxylic acid Step 1

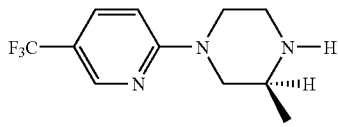

3-(S)-Methyl-1-(5-trifluoromethyl-pyridin-2-yl)-piperazine: 2-Bromo-5-trifluoromethyl-pyridine (1.06 g, 4.69 mmol), (S)-2-methylpiperazine (1.03 g, 10.28 mmol) and triethylamine (1.5 mL, 10.76 mmol) were stirred in toluene (10 mL) at 110° C. for 26 h. The reaction was cooled to room temperature, diluted with ethyl acetate (150 mL) and washed with water and brine. The organic layer was dried (MgSO$_4$), filtered and concentrated. The crude mixture was purified by automated silica gel flash column chromatography (gradient eluent 0-20% MeOH/dichloromethane) to afford 3-(S)-methyl-1-(5-trifluoromethyl-pyridin-2-yl)-piperazine (926 mg, 81%) as a yellow solid. $^1$H NMR (400 MHz, CDCl$_3$) δ8.38 (s, 1H), 7.62 (dd, 1H), 7.63 (d, 1H), 4.29-4.20 (m, 2H), 3.16-3.12 (m, 1H), 3.02-2.85 (m, 3H), 2.64-2.52 (m, 2H), 1.18 (d, 3H).

Step 2

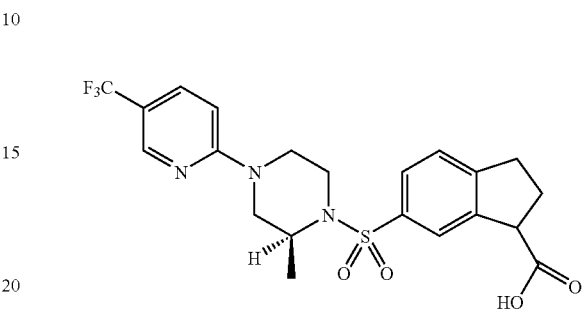

6-[2-(S)-Methyl-4-(5-Trifluoromethyl-pyridin-2-yl)-piperazine-1-sulfonyl]-indan-1-carboxylic acid: The compound 6-[2-(S)-methyl-4-(5-trifluoromethyl-pyridin-2-yl)-piperazine-1-sulfonyl]-indan-1-carboxylic acid was synthesized according to the procedure outlined in Example 1 using 3-(S)-methyl-1-(5-trifluoromethyl-pyridin-2-yl)-piperazine and indane-1-carboxylic acid methyl ester. $^1$H NMR (400 MHz, MeOH-d$_4$) δ8.33 (s, 1H), 7.90 (d, 1H, J=5.89 Hz), 7.71-7.67 (m, 1H), 7.62-7.57 (m, 1H), 7.35-7.31 (m, 1H), 6.58-6.52 (m, 1H), 4.27-3.96 (m, 4H), 3.80-3.69 (m, 1H), 3.37-3.21 (m, 2H), 3.15-2.92 (m, 3H), 2.52-2.40 (m, 2H), 1.11-1.08 (m, 3H); LCMS: 470.1 (M+1)$^+$.

EXAMPLE 24

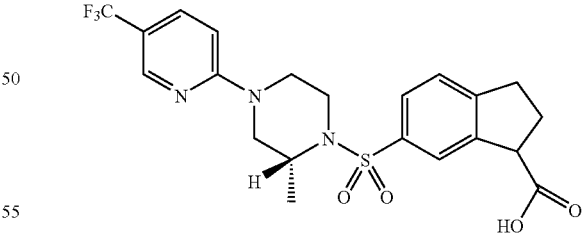

6-[2-(R)-Methyl-4-(5-trifluoromethyl-pyridin-2-yl)-piperazine-1-sulfonyl]-indan-1-carboxylic acid: The compound 6-[2-(R)-methyl-4-(5-trifluoromethyl-pyridin-2-yl)-piperazine-1-sulfonyl]-indan-1-carboxylic acid was synthesized according to the procedure outlined in Example 23 using 3-(R)-methyl-1-(5-trifluoromethyl-pyridin-2-yl)-piperazine and indan-1-carboxylic acid methyl ester. $^1$H NMR (400 MHz, MeOH-d$_4$) δ8.33 (s, 1H), 7.90 (d, 1H), 7.71-7.67 (m, 1H), 7.62-7.57 (m, 1H), 7.35-7.31 (m, 1H), 6.58-6.52 (m, 1H), 4.27-3.96 (m, 4H), 3.80-3.69 (m, 1H), 3.37-3.21 (m, 2H), 3.15-2.92 (m, 3H), 2.52-2.40 (m, 2H), 1.11-1.08 (m, 3H); LCMS: 470.0 (M+1)+.

EXAMPLE 25

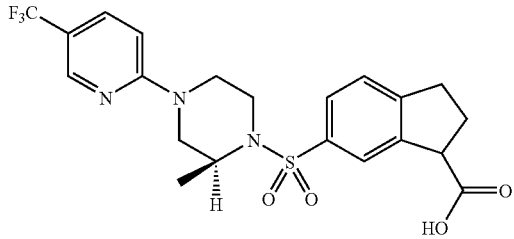

6-[3-(R)-Methyl-4-(5-trifluoromethyl-pyridin-2-yl)-piperazine-1-sulfonyl]-indan-1-carboxylic acid Step 1

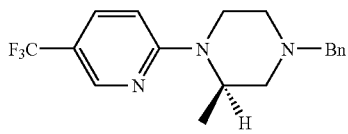

4-Benzyl-2-(R)-methyl-1-(5-trifluoromethyl-pyridin-2-yl)-piperazine: The compound 4-benzyl-2-(R)-methyl-1-(5-trifluoromethyl-pyridin-2-yl)-piperazine was synthesized according to the procedure outlined in Example 23 (step 1) using 1-benzyl-3-(R)-methyl-piperazine. $^1$H NMR (400 MHz, MeOH-D$_4$) δ8.38 (s, 1H), 7.76 (dd, 1H), 6.90 (d, 1H), 4.80-4.70 (m, 1H), 4.36-4.32 (m, 1H), 3.30-3.16 (m, 4H), 3.20-2.92 (m, 1H), 1.29 (d, 3H); LCMS: 336.1 (M+1)+.

Step 2

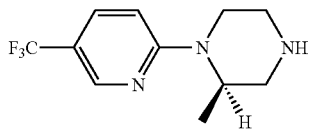

2-(R)-methyl-1-(5-trifluoromethyl-pyridin-2-yl)-piperazine: A solution of 4-benzyl-2-(R)-methyl-1-(5-trifluoromethyl-pyridin-2-yl)-piperazine (175 mg, 0.522 mmol) and 10% Pd/C (cat) in ethanol (5 mL) was stirred under a hydrogen atmosphere (50 psi) for 3 d. The reaction mixture was then filtered through Celite and purified by silica gel column chromatography (gradient eluent: 0-20% MeOH in dichloromethane) to provide the desired product (117 mg, 99%). $^1$H NMR (400 MHz, MeOH-D$_4$) δ8.39 (s, 1H), 7.60 (dd, 1H), 7.39-7.28 (m, 5H), 6.58 (d, 1H), 4.49 (br s, 1H), 4.10 (br d, 1H), 3.62 (br d, 1H), 3.47 (br d, 1H), 3.24 (br t, 1H), 2.95 (br d, 1H), 2.77 (br d, 1H), 2.35-2.15 (m, 2H), 1.25 (d, 3H); LCMS: 246.1 (M+1)+.

Step 3

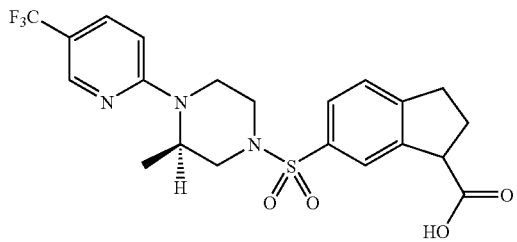

6-[3-(R)-Methyl-4-(5-trifluoromethyl-pyridin-2-yl)-piperazine-1-sulfonyl]-indan-1-carboxylic acid: The compound 6-[3-(R)-methyl-4-(5-trifluoromethyl-pyridin-2-yl)-piperazine-1-sulfonyl]-indan-1-carboxylic acid was synthesized according to the procedure outlined in Example 1 using 2-(R)-methyl-1-(5-trifluoromethyl-pyridin-2-yl)-piperazine and indane-1-carboxylic acid methyl ester. $^1$H NMR (400 MHz, MeOH-D$_4$) δ8.33 (s, 1H), 7.80 (s, 1H), 7.72-7.62 (m, 2H), 7.46 (dd, 1H), 6.80 (dd, 1H), 4.76-4.66 (m, 1H), 4.28 (br d, 1H), 4.14 (br t, 1H), 3.79 (br d, 1H), 3.61 (br d, 1H), 3.29-3.20 (m, 1H), 3.16-3.06 (m, 1H), 3.03-2.94 (m, 1H), 2.56-2.32 (m, 4H), 1.26 (m, 3H); LCMS: 470.0 (M+1)+.

EXAMPLE 26

6-[4-(3-Fluoro-4-trifluoromethyl-phenyl)-piperazine-1-sulfonyl]-indan-1-carboxylic acid

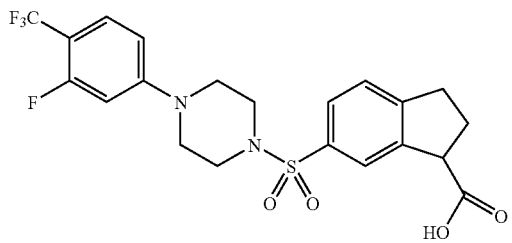

Step 1

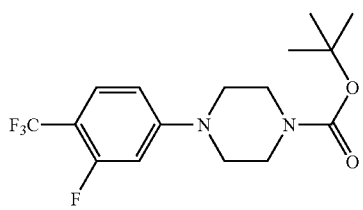

4-(3-Fluoro-4-trifluoromethyl-phenyl)-piperazine-1-carboxylic acid tert-butyl ester: Tert-butyl-1-piperazine-carboxylate (740 mg, 3.05 mmol) and 4-bromo-2-fluoro-1-trifluoromethyl-benzene (530 mg. 2.85 mmol) were dissolved in anhydrous toluene (6 mL, degassed). In a separate, septum-equipped vial were placed tri(dibenzylideneacetone)dipalladium(0) (152 mg, 0.17 mmol), 1,3-bis(2,6-di-i-propylphenyl)imidazolium chloride (283 mg, 0.67 mmol) and sodium t-butoxide (400 mg, 4.2 mmol). This "catalytic" vial was equipped with a magnetic stirbar and flushed with dry nitrogen. The reactant solution was next transferred to the "catalytic" vial and the mixture was stirred at 100° C. for 5 hours. After this period the mixture was combined with 20 mL of hexane/EtOAc (2:1) and was passed through a pad of Celite. The resulting filtrate was concentrated and purified using silica gel chromatography (0-20% EtOAc/Hexane) to yield 853 mg (86%) of 4-(3-Fluoro-4-trifluoromethyl-phenyl)-piperazine-1-carboxylic acid tert-butyl ester as a yellow residue. $^1$H NMR (400 MHz. CDCl$_3$) δ7.44-7.40 (m, 1H), 6.65-6.58 (m, 2H), 3.59-3.56 (m, 4H), 3.27-3.25 (m, 4H), 1.49 (s, 9H).

Step 2

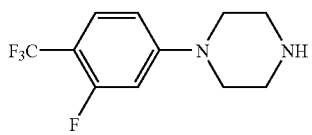

4-(3-Fluoro-4-trifluoromethyl-phenyl)-piperazine: 4-(3-Fluoro-4-trifluoromethyl-phenyl)-piperazine-1-carboxylic acid tert-butyl ester (853 mg, 2.45 mmol) was stirred in a mixture of trifluoroacetic acid/dichloromethane (5 mL, 25% v/v) for 20 min at room temperature. The reaction mixture was combined with 25 mL of CH$_2$Cl$_2$ and was washed with sat'd NaHCO$_3$ (2×10 mL) and brine. The resulting CH$_2$Cl$_2$ layer was dried over anhydrous Na$_2$SO$_4$ and was concentrated to yield crude amine. The product was further purified by silica gel chromatography (gradient eluent 0-10% MeOH in dichloromethane) to provide 4-(3-fluoro-4-trifluoromethyl-phenyl)-piperazine (473 mg, 78%). The product was used directly in step 3.

Step 3

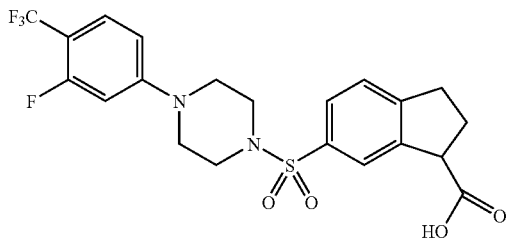

6-[4-(3-Fluoro-4-trifluoromethyl-phenyl)-piperazine-1-sulfonyl]-indan-1-carboxylic acid: The compound 6-[4-(3-fluoro-4-trifluoromethyl-phenyl)-piperazine-1-sulfonyl]-indan-1-carboxylic acid was synthesized according to the procedure outlined in Example 1 using 1-(3-fluoro-4-trifluoromethyl-phenyl)-piperazine and indane-1-carboxylic acid methyl ester. $^1$H NMR (400 MHz, MeOH-D$_4$) δ7.81 (s, 1H), 7.66-7.63 (m, 1H), 7.49-7.38 (m, 2H), 6.78-6.75 (m, 2H), 4.14 (t, 1H), 3.39-3.36 (m, 4H), 3.16-3.07 (m, 5H), 3.03-2.95 (m, 1H), 2.46-2.39 (m, 2H); LCMS: 472.9 (M+1)$^+$.

EXAMPLE 27

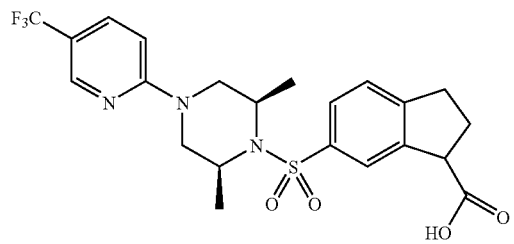

6-[cis-2,6-dimethyl-4-(5-trifluoromethyl-pyridin-2-yl)-piperazine-1-sulfonyl]-indan-1-carboxylic acid: The compound 6-[cis-2,6-dimethyl-4-(5-trifluoromethyl-pyridin-2-yl)-piperazine-1-sulfonyl]-indan-1-carboxylic acid was synthesized according to the procedure outlined in Example 23 using cis-2,6-dimethylpiperazine. $^1$H NMR (400 MHz, MeOH-d$_4$) δ8.31 (s, 1H), 7.89 (s, 1H), 7.70 (d, 1H), 7.58 (dd, 1H), 7.31 (d, 1H), 6.54 (d, 1H), 4.34-4.26 (m, 1H), 4.20-4.05 (m, 2H), 3.99 (t, 2H), 3.13-2.91 (m, 4H), 2.52-2.36 (m, 2H), 1.37 (d, 6H); LCMS: 484.0 (M+1)$^+$.

EXAMPLE 28

6-[cis-2,6-Dimethyl-4-(5-trifluoromethyl-pyridin-2-yl)-piperazine-1-sulfonyl]-1-methyl-indan-1-carboxylic acid

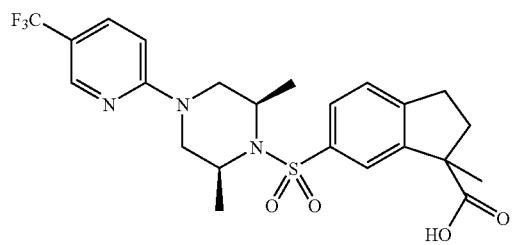

Step 1

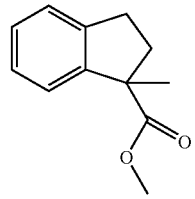

1-Methyl-indan-1-carboxylic acid methyl ester: The compound 1-methyl-indan-1-carboxylic acid methyl ester was prepared according to the procedure in Example 13 using indane-1-carboxylic acid methyl ester (67%). $^1$H NMR (400 MHz, CDCl$_3$) δ7.32-7.16 (m, 4H), 3.66 (s, 3H), 3.11-3.04 (m, 1H), 2.97-2.90 (m, 1H), 2.76-2.70 (d, 1H), 1.99-1.92 (m, 1H), 1.55 (s, 3H).

Step 2

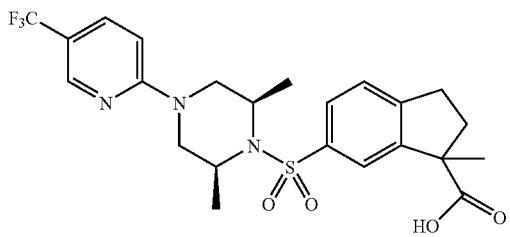

6-[cis-2,6-dimethyl-4-(5-trifluoromethyl-pyridin-2-yl)-piperazine-1-sulfonyl]-1-methyl-indan-1-carboxylic acid: The compound 6-[cis-2,6-dimethyl-4-(5-trifluoromethyl-pyridin-2-yl)-piperazine-1-sulfonyl]-1-methyl-indan-1-carboxylic acid was synthesized according to the procedure outlined in Example 27 using 1-methyl-indan-1-carboxylic acid methyl ester and 2,6-dimethyl piperazine. $^1$H NMR (400 MHz, MeOH-d$_4$) δ 8.26 (s, 1H), 7.96 (dd, 1H), 7.65 (dd, 1H), 7.32 (d, 1H), 4.30-4.22 (m, 1H), 4.18-4.11 (m, 1H), 4.04-3.98 (m, 1H), 3.35 (s, 3H), 3.08-2.92 (m, 4H), 2.76-2.70 (m, 1H), 2.04-1.97 (m, 1H), 1.55 (s, 3H), 1.36-1.33 (m, 6H); LCMS: 498.1 (M+1)$^+$.

EXAMPLE 29

{6-Methoxy-5-[4-(4-trifluoromethyl-phenyl)-piperazine-1-sulfonyl]-indan-1-yl}-acetic acid

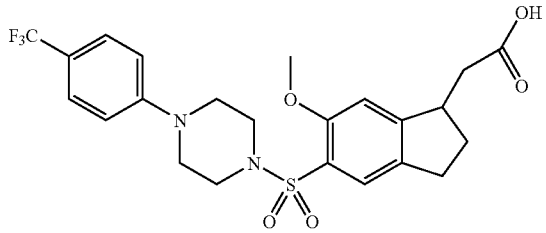

Step 1

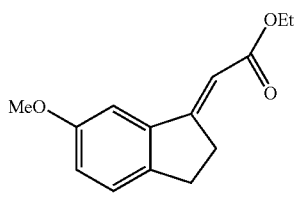

(6-Methoxy-indan-1-ylidene)-acetic acid ethyl ester: 6-Methoxy-indan-1-one (5.02 g, 30.95 mmol) and triethyl phosphonoacetate (15.5 mL, 78.13 mmol) was dissolved in THF (20 mL) and added slowly to a mixture of EtOH (850 μL) and NaH (60% dispersion in oil, 2.5 g). The resulting slurry was stirred at 70° C. overnight. The crude mixture was diluted with diethyl ether and washed with water and brine, dried (Na$_2$SO$_4$), filtered and concentrated. The product was purified by silica gel flash column chromatography (5:1 hexanes in ethyl acetate) to afford (6-Methoxy-indan-1-ylidene)-acetic acid ethyl ester (3.18 g, 47%) as a mixture (~1:1) of E/Z isomers. $^1$H NMR (400 MHz, CDCl$_3$) mixture (~1:1) of E/Z isomers δ 7.37 (d, 1H) 7.27 (d, 1H), 7.09 (d, 1H), 6.99 (dd, 1H), 6.97 (d, 1H), 6.81 (dd, 1H), 6.50 (m, 1H), 6.31-6.30 (m, 1H), 4.27 (quart, 2H), 4.22 (quart, 2H), 3.87 (s, 3H), 3.86 (s, 3H), 3.60 (m, 2H), 3.36-3.33 (m, 4H), 3.05-3.02 (m, 2H), 1.37 (t, 3H), 1.31 (t, 3H).

Step 2

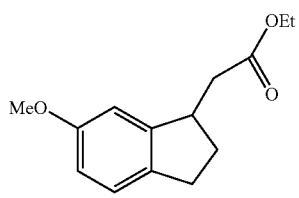

(6-Methoxy-indan-1-yl)-acetic acid ethyl ester: (6-methoxy-indan-1-ylidene)-acetic acid ethyl ester (3.18 g, 14.5 mmol) was dissolved in MeOH (30 ml). A catalytic amount of 10% Pd/C was added and the reaction was stirred under an atmosphere of hydrogen (balloon) for 2 h. The reaction mixture was filtered through Celite to provide pure (6-methoxy-indan-1-yl)-acetic acid ethyl ester (2.98 g, 94%) as a clear oil. LCMS: 235.0 (M+1)$^+$.

Step 3

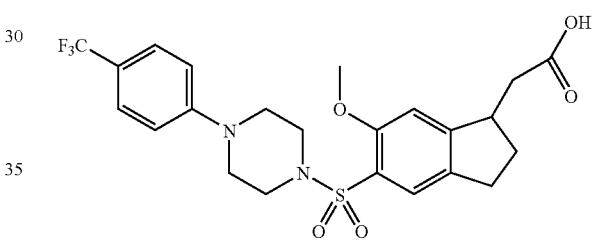

{6-Methoxy-5-[4-(4-trifluoromethyl-phenyl)-piperazine-1-sulfonyl]-indan-1-yl}-acetic acid: The compound {6-methoxy-5-[4-(4-trifluoromethyl-phenyl)-piperazine-1-sulfonyl]-indan-1-yl}-acetic acid was synthesized according to the procedure outlined in example 1 using (6-methoxy-indan-1-yl)-acetic acid ethyl ester. $^1$H NMR (400 MHz, MeOH-d$_4$) δ 7.67 (s, 1H) 7.46 (d, 2H), 7.10 (s, 1H), 7.01 (d, 2H), 3.89 (s, 3H), 3.57 (quint., 1H), 3.30 (m, 8H), 2.96-2.78 (m, 3H), 2.49-2.37 (m, 2H), 1.85-1.76 (m, 1H); LCMS: 498.9 (M+1)$^+$.

EXAMPLE 30

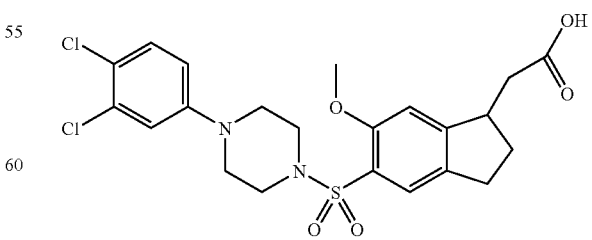

{5-[4-(3,4-Dichloro-phenyl)-piperazine-1-sulfonyl]-6-methoxy-indan-1-yl}-acetic acid: {5-[4-(3,4-dichloro-phenyl)-piperazine-1-sulfonyl]-6-methoxy-indan-1-yl}-acetic acid was synthesized according to the procedure outlined in Example 29 using 3,4-dichlorophenyl piperazine. ¹H NMR (400 MHz, MeOH-d₄) δ7.64 (s, 1H)7.28 (d, 1H), 7.14-7.12 (s, 1H), 7.04 (d, 1H), 6.85 (dd, 1H), 3.90 (s, 3H), 3.60 (quint., 1H), 3.30-3.27 (m, 4H), 3.19-3.17 (m, 4H), 2.95-2.76 (m, 2H), 2.60 (dd, 1H), 2.43-2.33 (m, 2H), 1.85-1.76 (m, 1H); LCMS: 498.8 (M+1)⁺.

EXAMPLE 31

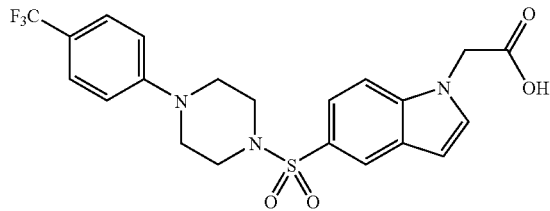

{5-[4-(4-Trifluoromethyl-phenyl)-piperazine-1-sulfonyl]-indol-1-yl}-acetic acid

Step 1

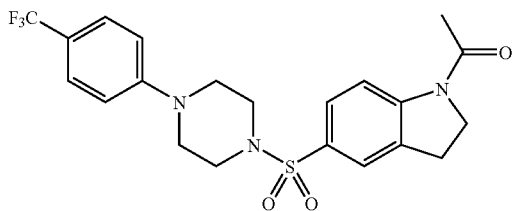

1-{5-[4-(4-Trifluoromethyl-phenyl)-piperazine-1-sulfonyl]-2,3-dihydro-indol-1-yl}-ethanone: The compound 1-{5-[4-(4-trifluoromethyl-phenyl)-piperazine-1-sulfonyl]-2,3-dihydro-indol-1-yl}-ethanone was synthesized according to the procedure outlined in Example 1 using 1-acetyl indoline (89%). ¹H NMR (400 MHz, CDCl₃) δ8.43 (d 1H), 7.62 (d, 1H) 7.57 (s, 1H), 7.47 (d, 2H), 6.88 (d, 2H), 4.16 (t, 2H), 3.35 (m, 4H), 3.28 (t, 2H), 3.15 (m, 4H), 2.27 (s, 3H); LCMS: 454.0 (M+1)⁺.

Step 2

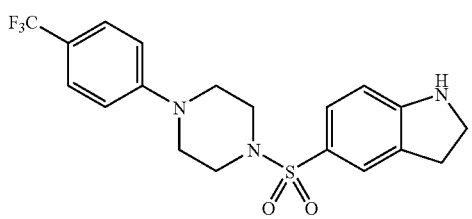

5-[4-(4-Trifluoromethyl-phenyl)-piperazine-1-sulfonyl]-2,3-dihydro-1H-indole: 1-{5-[4-(4-Trifluoromethyl-phenyl)-piperazine-1-sulfonyl]-2,3-dihydro-indol-1-yl}-ethanone was refluxed in 1,4-dioxane (5 mL) and concentrate HCl (2.5 mL) for 2 h. The reaction was then diluted with dichloromethane and washed with 1N HCl, saturated sodium bicarbonate, dried (Na₂SO₄), filtered and concentrated to provide 5-[4-(4-trifluoromethyl-phenyl)-piperazine-1-sulfonyl]-2,3-dihydro-1H-indole (1.03 g, 75%) as an off-white solid. ¹H NMR (400 MHz, CDCl₃) δ7.48-7.20 (m, 4H), 6.88 (d, 2H), 6.60 (d, 1H), 3.70 (t, 2H), 3.36-3.33 (m, 4H), 3.15-3.12 (m, 4H), 3.10 (t, 2H).

Step 3

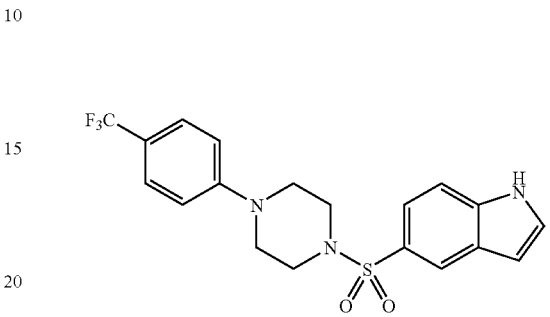

5-[4-(4-Trifluoromethyl-phenyl)-piperazine-1-sulfonyl]-1H-indole: 5-[4-(4-Trifluoromethyl-phenyl)-piperazine-1-sulfonyl]-2,3-dihydro-1H-indole (180 mg, 0.44 mmol) was dissolved in dichloromethane (10 mL). DDQ (100 mg, 0.44 mmol) was added and stirred at room temperature for 4 h. The reaction was concentrated and purified by silica gel flash column chromatography (45% ethyl acetate in hexanes) to provide 5-[4-(4-trifluoromethyl-phenyl)-piperazine-1-sulfonyl]-1H-indole (70%) as a white solid. ¹H NMR (400 MHz, DMSO-D₆) δ11.72 (s, 1H), 8.07 (s, 1H) 7.65 (d, 1H), 7.62-7.61 (m, 1H), 7.52-7.48 (m, 3H), 7.04 (d, 2H), 6.71 (m, 1H), 3.40-3.36 (m, 4H), 3.02-2.99 (m, 4H).

Step 4

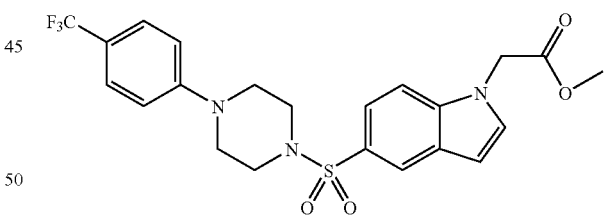

{5-[4-(4-Trifluoromethyl-phenyl)-piperazine-1-sulfonyl]-indol-1-yl}-acetic acid methyl ester: 5-[4-(4-Trifluoromethyl-phenyl)-piperazine-1-sulfonyl]-1H-indole (60 mg, 0.15 mmol), methyl bromo acetate (16 μL, 0.18 mmol) and cesium carbonate (95 mg, 0.29 mmol) were stirred in acetonitrile (10 ml) overnight at 70° C. The reaction mixture was diluted with ethyl acetate, washed with water, brine, dried (Na₂SO₄) and concentrated to provide {5-[4-(4-trifluoromethyl-phenyl)-piperazine-1-sulfonyl]-indol-1-yl}-acetic acid methyl ester (99%) as a yellow oil. ¹H NMR (400 MHz, CDCl₃) δ 8.11 (d, 1H) 7.60 (dd, 1H), 7.43 (d, 2H), 7.36 (d, 1H), 7.24 (d, 1H), 6.83 (d, 2H), 6.90 (d, 1H), 4.91 (s, 2H), 3.76 (s, 3H), 3.32-3.30 (m, 4H), 3.15-3.13 (m, 4H).

Step 5

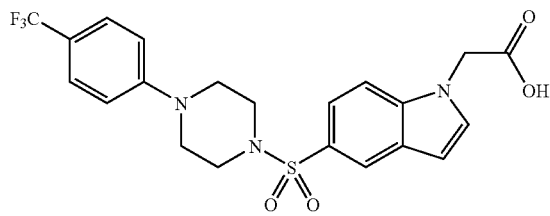

{5-[4-(4-Trifluoromethyl-phenyl)-piperazine-1-sulfonyl]-indol-1-yl}-acetic acid: The compound {5-[4-(4-Trifluoromethyl-phenyl)-piperazine-1-sulfonyl]-indol-1-yl}-acetic acid methyl ester was hydrolyzed according to the procedure outlined in Example 1 (99%). $^1$H NMR (400 MHz, CDCl$_3$) δ 8.08 (d, 1H) 7.70 (dd, 1H), 7.60 (d, 1H), 7.53 (m, 3H), 7.04 (d, 2H), 6.74 (d, 1H), 5.16 (s, 2H), 3.39 (m, 4H), 3.01 (m, 4H).

EXAMPLE 32

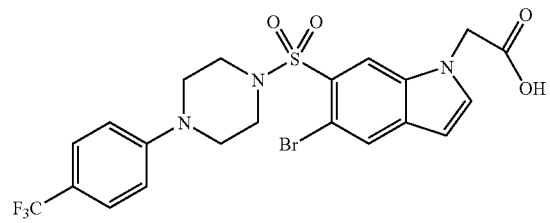

{5-Bromo-6-[4-(4-trifluoromethyl-phenyl)-piperazine-1-sulfonyl]-indol-1-yl}-acetic acid: {5-Bromo-6-[4-(4-trifluoromethyl-phenyl)-piperazine-1-sulfonyl]-indol-1-yl}-acetic acid was synthesized according to the procedure outlined in Example 31 using 1-(5-Bromo-2,3-dihydro-indol-1-yl)-ethanone as the starting material. $^1$H NMR (400 MHz, CDCl$_3$) δ 8.14(s, 1H) 7.95 (s, 1H), 7.46 (d, 2H), 7.28 (d, 1H), 6.88 (d, 2H), 6.56 (d, 1H), 4.94 (s, 2H), 3.44-3.42 (m, 4H), 3.28-3.26 (m, 4H).

EXAMPLE 33

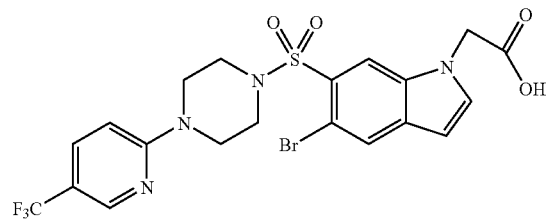

{5-Bromo-6-[4-(5-trifluoromethyl-pyridin-2-yl)-piperazine-1-sulfonyl]-indol-1-yl}-acetic acid: {5-Bromo-6-[4-(5-trifluoromethyl-pyridin-2-yl)-piperazine-1-sulfonyl]-indol-1-yl}-acetic acid was synthesized according to the procedure outlined in Example 31 using 1-(5-Bromo-2,3-dihydro-indol-1-yl)-ethanone and 1-[5-(trifluoromethyl)-pyrid-2-yl] piperazine. $^1$H NMR (400 MHz, CDCl$_3$) δ 8.24 (s, 1H) 8.07 (s, 1H), 7.87 (s, 1H), 7.63 (dd, 1H), 7.23 (d, 1H), 6.61 (d, 1H), 6.46 (d, 1H), 5.30 (s, 2H), 3.66-3.63 (m, 4H), 3.34-3.32 (m, 4H).

EXAMPLE 34

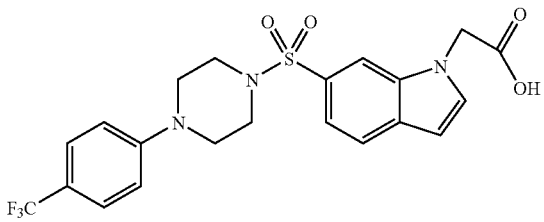

{6-[4-(4-Trifluoromethyl-phenyl)-piperazine-1-sulfonyl]-indol-1-yl}-acetic acid

Step 1

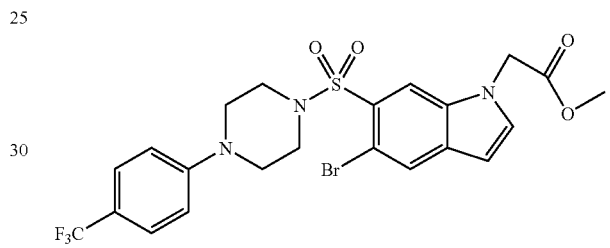

{5-Bromo-6-[4-(4-trifluoromethyl-phenyl)-piperazine-1-sulfonyl]-indol-1-yl}-acetic acid methyl ester: The compound {5-bromo-6-[4-(4-trifluoromethyl-phenyl)-piperazine-1-sulfonyl]-indol-1-yl}-acetic acid methyl ester was synthesized according to the procedure outlined in Example 31 using 1-(5-bromo-2,3-dihydro-indol-1-yl)-ethanone as the starting material. $^1$H NMR (400 MHz, CDCl$_3$) δ 8.13(s, 1H) 7.98 (s, 1H), 7.47 (d, 2H), 7.31 (d, 1H), 6.90 (d, 2H), 6.58 (d, 1H), 4.11 (dd, 2H), 3.79 (s, 3H), 3.45 (m, 4H), 3.32 (m, 4H).

Step 2

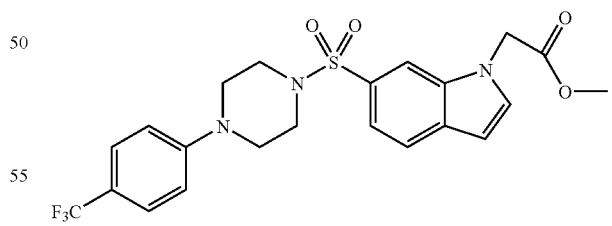

{6-[4-(4-Trifluoromethyl-phenyl)-piperazine-1-sulfonyl]-indol-1-yl}-acetic acid methyl ester: {5-Bromo-6-[4-(4-trifluoromethyl-phenyl)-piperazine-1-sulfonyl]-indol-1-yl}-acetic acid methyl ester (135 mg, 0.24 mmol), triethylamine (40 μL, 0.29 mmol) and 10% Pd/carbon (cat) were stirred under an atmosphere of hydrogen until all the starting material was gone. The reaction was then filtered through celite, concentrated and purified by flash column chromatography (60% hexanes in ethyl acetate) to afford {6-[4-(4-trifluoromethyl-phenyl)-piperazine-1-sulfonyl]-indol-1-yl}-acetic acid methyl ester (96 mg, 83%) as a clear oil. ¹H NMR (400 MHz, CDCl₃) δ 7.76(d, 1H) 7.75 (d, 1H), 7.51 (dd, 1H), 7.44 (dd, 2H), 7.31 (d, 1H), 6.84 (d, 2H), 6.67 (d, 1H), 4.11 (dd, 2H), 3.78 (s, 3H), 3.33 (m, 4H), 3.16 (m, 4H).

Step 3

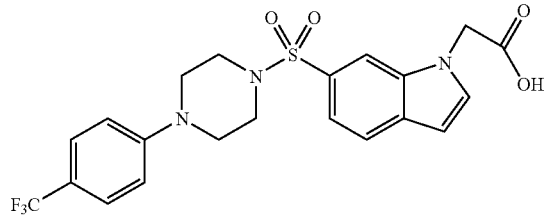

{6-[4-(4-Trifluoromethyl-phenyl)-piperazine-1-sulfonyl]-indol-1-yl}-acetic acid: {6-[4-(4-Trifluoromethyl-phenyl)-piperazine-1-sulfonyl]-indol-1-yl}-acetic acid methyl ester was hydrolyzed according to the procedure in Example 1 (87%). ¹H NMR (400 MHz, CDCl₃) δ 7.93(d, 1H) 7.82 (d, 1H), 7.67 (d, 1H), 7.50 (d, 2H), 7.42 (dd, 1H), 7.03 (d, 2H), 6.60 (d, 1H), 5.20 (s, 2H), 3.37 (m, 4H), 3.02 (m, 4H).

EXAMPLE 35

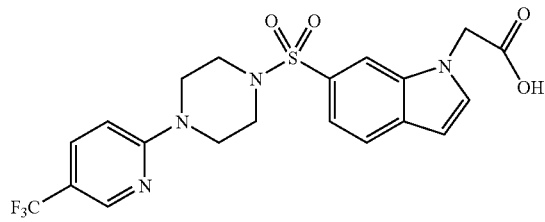

{6-[4-(5-Trifluoromethyl-pyridin-2-yl)-piperazine-1-sulfonyl]-indol-1-yl}-acetic acid: The compound {6-[4-(5-trifluoromethyl-pyridin-2-yl)-piperazine-1-sulfonyl]-indol-1-yl}-acetic acid was synthesized according to the procedure outlined in Example 34 using 1-[5-(trifluoromethyl)-pyrid-2-yl]piperazine. ¹H NMR (400 MHz, CDCl₃) δ 8.31 (s, 1H), 7.73(d, 1H) 7.72 (s, 1H), 7.58 (dd, 1H), 7.48 (dd, 1H), 7.30 (d, 1H), 6.64 (d, 1H), 6.56 (d, 1H), 4.93 (s, 2H), 3.74 (m, 4H), 3.10 (m, 4H).); LCMS: 468.9 (M+1)⁺.

EXAMPLE 36

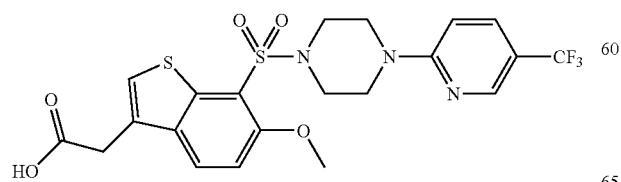

{6-Methoxy-7-[4-(5-trifluoromethyl-pyridin-2-yl)-piperazine-1-sulfonyl]-benzo[b]thiophen-3-yl}-acetic acid Step 1

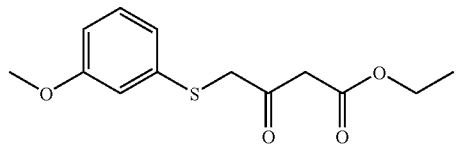

4-(3-Methoxy-phenylsulfanyl)-3-oxo-butyric acid ethyl ester: A solution of ethyl-4-chloroacetoacetate (8.75 g, 71.2 mmol) in 20 mL of acetonitrile was added slowly to a mixture of 3-methoxybenzenethiol (9.69 g, 71.2 mmol) and cesium carbonate (46.4 g, 14.2 mmol) in acetonitrile (200 mL) over 5 minutes. The mixture was stirred at room temperature for 2 hours and filtered through a bed of Celite. Evaporation of the filtrate gave an oil which solidified on standing. The residue was dissolved in EtOAc, and the solution was sequentially washed with H₂O, brine, and dried over Na₂SO₄. Evaporation of solvent afforded 14.0 g of desired ester. ¹H NMR (400 MHz, CDCl₃) δ 7.20 (t, 1H), 6.90 (d, 1H), 6.87 (s, 1H), 6.79 (d, 1H), 4.20 (q, 2H), 3.82 (s, 2H), 3.79 (s, 3H), 3.63 (s, 2H), 1.26 (t, 3H).

Step 2

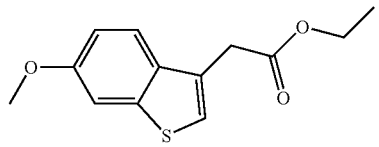

(6-Methoxy-benzo[b]thiophen-3-yl)-acetic acid ethyl ester: Compound from step 1 (7.0 g, 26.0 mmol) was slowly added to methanesulfonic acid (100 mL) at room temperature. The resulting solution was stirred for 20 minutes and added dropwise into ice (250 g). The aqueous mixture was extracted two times with EtOAc. The organic layer was washed with brine, saturated NaHCO₃, and dried over Na₂SO₄. After removal of solvent, the residue was purified by chromatography on silica gel (3:7 EtOAc/hexane) to give 4.33 g of desired compound.

Step 3

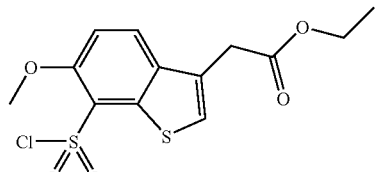

(7-Chlorosulfonyl-6-methoxy-benzo[b]thiophen-3-yl)-acetic acid ethyl ester: To a solution of compound from step 2 (1.0 g, 4.0 mmol) in CH₂Cl₂ (10 mL) was added chlorosulfonic acid (0.56 mL, 8.0 mmol). The resulting mixture was stirred for 4 hours at room temperature. The solvent was evaporated in vacuo and the residue was dissolved in EtOAc.

The solution was washed with Na$_2$CO$_3$, brine and dried over Na$_2$SO$_4$. Evaporation of solvent afforded 50 mg of desired compound. $^1$H NMR (400 MHz, CDCl$_3$) δ 8.08 (d, 1H), 7.38 (s, 1H), 6.90 (d, 1H), 4.21 (q, 2H), 4.02 (s, 2H), 4.01 (s, 3H), 1.24 (t, 3H).

Step 4

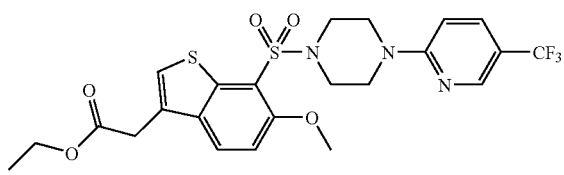

{6-Methoxy-7-[4-(5-trifluoromethyl-pyridin-2-yl)-piperazine-1-sulfonyl]-benzo[b]thiophen-3-yl}-acetic acid ethyl ester: To a solution of compound from step 3 (50 mg, 0.14 mmol) in THF (2 mL) was added 1-[5-(trifluoromethyl)-2-pyridinyl]piperazine (32 mg, 0.14 mmol), followed by triethylamine (39 μL, 0.28 mmol). The reaction solution was stirred for 4 hours at room temperature. The solvent was evaporated and the residues were purified by silica gel chromatography to afford 22 mg of desired compound.

Step 5

{6-Methoxy-7-[4-(5-trifluoromethyl-pyridin-2-yl)-piperazine-1-sulfonyl]-benzo[b]thiophen-3-yl}-acetic acid: Compound from step 4 (22 mg, 0.041 mmol) was dissolved in 2 mL of THF/MeOH (3:1), followed by addition of 1N LiOH (5.0 eqv). The resulting mixture were stirred at 40° C. for 3 hours. The organic solvent was evaporated under N$_2$ and residues were diluted with water (2 mL). The aqueous layers were partitioned with ether (2 mL). After removal of organic layers, the aqueous layers were neutralized by 1N HCl (5.0 eqv) and then extracted with ethyl acetate (5 mL). The organic layers were washed with H$_2$O, brine, and dried over Na$_2$SO$_4$. The solution was concentrated in vacuo to afford {6-Methoxy-7-[4-(5-trifluoromethyl-pyridin-2-yl)-piperazine-1-sulfonyl]-benzo[b]thiophen-3-yl}-acetic acid. $^1$H NMR (400 MHz, CDCl$_3$) δ 8.32 (s, 1H), 8.38 (s, 1H), 7.78 (d, 1H), 7.61 (d, 1H), 7.22 (s, 1H), 6.60 (m, 1H), 4.01 (s, 2H), 3.98 (s, 3H), 3.77 (m, 4H), 3.22 (m, 4H).

EXAMPLE 37

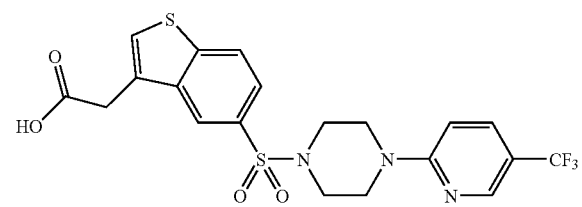

{5-[4-(5-Trifluoromethyl-pyridin-2-yl)piperazine-1-sulfonyl]-benzo[b]thiophen-3-yl}-acetic acid: The compound of {5-[4-(5-Trifluoromethyl-pyridin-2-yl)piperazine-1-sulfonyl]-benzo[b]thiophen-3-yl}-acetic acid was prepared according to the method used to prepare Example 36 using benzo[b]thiophen-3-yl-acetic acid methyl ester. $^1$H NMR (400 MHz, CDCl$_3$) δ 8.33 (s, 1H), 8.32 (s, 1H), 7.87 (d, 1H), 7.78 (d, 1H), 7.65 (s, 1H), 7.62 (d, 1H), 6.59 (d, 1H), 3.93 (s, 2H), 3.78 (m, 4H), 3.14 (m, 4H).

EXAMPLE 38

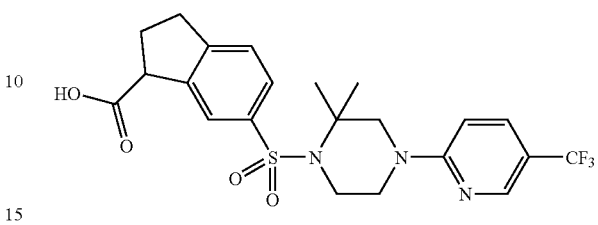

6-[2,2-Dimethyl-4-(5-trifluoromethyl-pyridin-2-yl)-piperazine-1-sulfonyl]-indan-1-carboxylic acid: The compound 6-[2,2-Dimethyl-4-(5-trifluoromethyl-pyridin-2-yl)-piperazine-1-sulfonyl]-indan-1-carboxylic acid was prepared according to the method used to prepare Example 26 using 2,2-dimethyl-4-(5-trifluoromethy-pyridin-2-yl)piperazine. $^1$H NMR (400 MHz. CDCl$_3$) δ 8.36 (s, 1H), 7.91 (s, 1H), 7.71 (d, 1H), 7.61 (d, 1H) 7.36-7.31 (m, 1H), 6.52 (d, 1H), 4.15-4.11 (m, 1H), 3.73-3.53 (m, 6H), 3.18-3.12 (m, 1H), 3.10-2.95 (m, 1H), 2.54-2.42 (m, 2H), 1.39 (s, 6H). ESMS (M+H): 484.1.

EXAMPLE 39

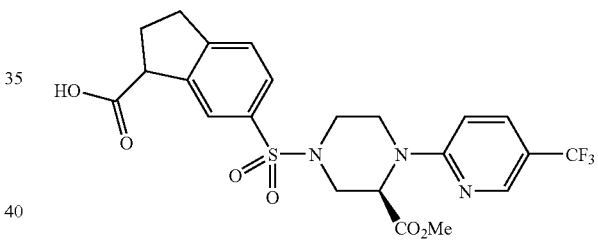

(R)-4-(3-Carboxy-indane-5-sulfonyl)-1-(5-trifluoromethyl-pyridin-2-yl)-piperazine-2-carboxylic acid methyl ester Step 1

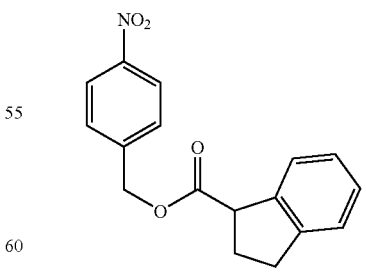

Indan-1-carboxylic acid 4-nitro-benzyl ester: To a solution of 3H-Indene-1-carboxylic acid (2.0 g, 13.3 mmol) in ethanol (35 mL) was added 10% Pd/C (200 mg). The reaction mixture was stirred under an H$_2$ atmosphere for 1 h. The mixture was filtered through Celite and concentrated in vacuo. The residue was combined with p-nitrobenzyl bromide (5.8 g, 26.8 mmoles) and 1,8-diazabicyclo[5.4.0]undec-7-ene (2.4 mL, 16.0 mmol) in 65 mL of benzene, and was stirred at 50° C. for 20 hours. After this period the heterogeneous mixture was gravity filtered and the filtrate was evaporated in vacuo. The residue was combined with CH$_2$Cl$_2$ and was washed with 1N HCl (2×25 mL) and sat'd NaHCO$_3$ (2×25 mL), and the resulting CH$_2$Cl$_2$ solution was dried over anhydrous Na$_2$SO$_4$. The crude solid was purified using flash silica chromatography (0-10% EtOAc/Hexane) to yield 3.61 g (95%) of the intermediate.

Step 2

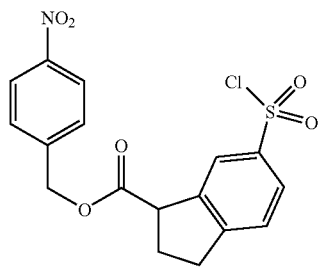

6-Chlorosulfonyl-indan-1-carboxylic acid 4-nitro-benzyl ester: To a solution of indan-1-carboxylic acid 4-nitro-benzyl ester (2.3 g, 8.1 mmol) in anhydrous CHCl$_3$ (13 mL) at −20° C. was added chlorosulfonic acid (2.8 g, 24.0 mmol) over a period of 10 minutes. The mixture was warmed to ambient temperature and stirred for 16 h. The reaction mixture was combined with ice-water and the resulting layer was extracted with CH$_2$Cl$_2$. The CH$_2$Cl$_2$ layer was washed with brine and was dried over anhydrous Na$_2$SO$_4$. The crude product was purified using flash silica chromatography (0-30% EtOAc/Hex) to yield 0.84 g (27%) of 6-chlorosulfonyl-indan-1-carboxylic acid 4-nitro-benzyl ester.

Step 3

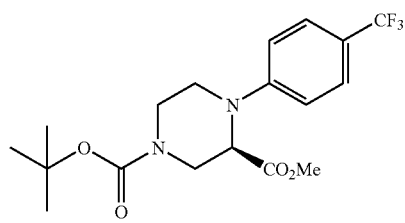

4-(5-Trifluoromethyl-pyridin-2-yl)-piperazine-1,3-dicarboxylic acid 1-tert-butyl ester 3-methyl ester: 3-Methyl-piperazine-1,3-dicarboxylic acid 1-tert-butyl ester (120 mg, 0.49 mmol) and 2-Bromo-5-trifluoromethyl-pyridine (133 mg, 0.59 mmol) were dissolved in 2.0 mL of anhydrous toluene (degassed). In a separate, septum-equipped vial were placed tri(dibenzylideneacetone)dipalladium(0) (22 mg, 0.024 mmol), 1,3-bis(2,6-di-i-propylphenyl)imidazolium chloride (42 mg, 0.1 mmol) and sodium t-butoxide (57 mg, 0.59 mmol). This "catalytic" vial was equipped with a magnetic stir bar and flushed with dry nitrogen. The reactant solution was next transferred to the "catalytic" vial and the mixture was stirred at 100° C. for 5 h. After this period the mixture was combined with 20 mL of hexane/EtOAc (2:1) and was passed through a pad of Celite. The resulting filtrate was evaporated in vacuo and purified using flash silica chromatography (0-20% EtOAc/Hexane) to yield 110 mg (58%) of 4-(5-Trifluoromethyl-pyridin-2-yl)-piperazine-1,3-dicarboxylic acid 1-tert-butyl ester 3-methyl ester.

Step 4

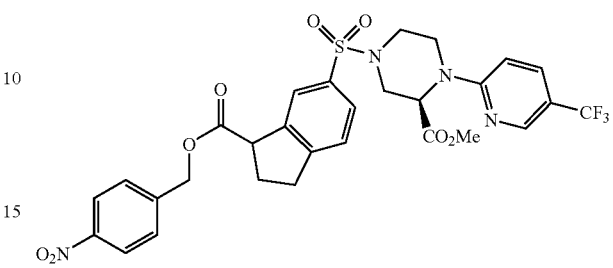

4-[3-(4-Nitro-benzyloxycarbonyl)-indane-5-sulfonyl]-1-(5-trifluoromethyl-pyridin-2-yl)-piperazine-2-carboxylic acid methyl ester: 4-(5-Trifluoromethyl-pyridin-2-yl)-piperazine-1,3-dicarboxylic acid 1-tert-butyl ester 3-methyl ester (110 mg, 0.28 mmol) was combined with 2.0 mL of 25% TFA/CH$_2$Cl$_2$ and was stirred at room temperature for 30 min. After this period the reaction mixture was diluted with CH$_2$Cl$_2$ (25 mL) and was washed with sat'd NaHCO$_3$ (2×10 mL) and brine. The resulting CH$_2$Cl$_2$ layer was dried over anhydrous Na$_2$SO$_4$ and was evaporated in vacuo to yield crude amine. The crude amine was purified using flash silica chromatography (0-10% MeOH/CH$_2$Cl$_2$) to yield 77 mg (94%) of (R)-4-(5-trifluoromethyl-pyridin-2-yl)-piperazine-2-carboxylic acid methyl ester as a yellow residue. This material was combined with 6-Chlorosulfonyl-indan-1-carboxylic acid 4-nitro-benzyl ester from Step 2 (102 mg, 0.27 mmoles) and triethylamine (46 μL, 0.33 mmol) in 2.0 mL of anhydrous THF, and was stirred at 60° C. for 5 hours. After this period the reaction mixture was evaporated in vacuo and the resulting residue was combined with 30 mL of benzene. The resulting heterogeneous mixture was filtered with benzene washings. The filtrate was then evaporated in vacuo and purified using flash silica chromatography (0-30% EtOAc/Hexane) to yield 4-[3-(4-Nitro-benzyloxycarbonyl)-indane-5-sulfonyl]-1-(5-trifluoromethyl-pyridin-2-yl)-piperazine-2-carboxylic acid methyl ester.

Step 5

(R)-4-(3-Carboxy-indane-5-sulfonyl)-1-(5-trifluoromethyl-pyridin-2-yl)-piperazine-2-carboxylic acid methyl ester: 4-[3-(4-Nitro-benzyloxycarbonyl)-indane-5-sulfonyl]-1-(5-trifluoromethyl-pyridin-2-yl)-piperazine-2-carboxylic acid methyl ester (87 mg, 0.14 mmol) obtained from step 4 was combined with 10% Pd/C (75 mg), cyclohexadiene (260 μL, 2.8 mmol) and 2.0 mL of ethanol within an 8 mL Teflon-capped vial. This mixture was stirred at 70° C. for 6 h and then passed through a Celite plug (with MeOH washings). The resulting filtrate was evaporated in vacuo, and the crude residue was purified using flash silica chromatography (0-10% MeOH/CH$_2$Cl$_2$) to yield (R)-4-(3-Carboxy-indane-5-sulfonyl)-1-(5-trifluoromethyl-pyridin-2-yl)-piperazine-2-carboxylic acid methyl ester. $^1$H NMR (400 MHz, CD$_3$OD) δ 8.37 (m, 1H), 7.85 (s, 1H), 7.80 (d, 1H), 7.69 (d, 1H), 7.52 (d, 1H), 6.94 (d, 1H), 5.55 (m, 1H), 4.33-4.29 (m, 1H), 4.20-4.11 (m, 2H), 3.84-3.81 (m, 1H), 3.74 (s, 3H), 3.47-3.41 (m, 1H), 3.20-3.14 (m, 1H), 3.07-2.99 (m, 1H), 2.65-2.61 (m, 1H), 2.51-2.42 (m, 3H). ESMS (M+H): 514.0

EXAMPLE 40

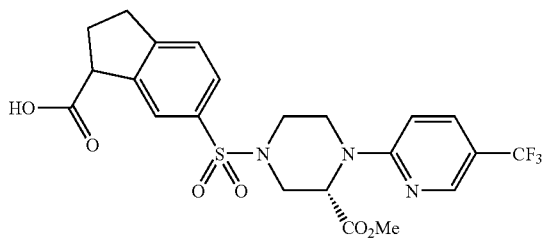

(S)-4-(3-Carboxy-indane-5-sulfonyl)-1-(5-trifluoromethyl-pyridin-2-yl)-piperazine-2-carboxylic acid methyl ester: The compound of (S)-4-(3-carboxy-indane-5-sulfonyl)-1-(5-trifluoromethyl-pyridin-2-yl)-piperazine-2-carboxylic acid methyl ester was prepared according to the method used to prepare example 39. ¹H NMR (400 MHz, CDCl₃) δ 8.35 (m, 1H), 7.85 (s, 1H), 7.69-7.62 (m, 2H), 7.41 (d, 1H), 6.68-6.01 (m, 1H), 5.53 (m, 1H), 4.35 (d, 1H), 4.16-4.13 (m, 1H), 3.90-3.82 (m, 2H), 3.74 (s, 3H), 3.60-3.51 (m, 1H), 3.19-3.11 (m, 1H), 3.03-2.95 (m, 1H), 2.64-2.60 (m, 1H), 2.52-2.46 (m, 3H). ESMS (M+H): 514.0

EXAMPLE 41

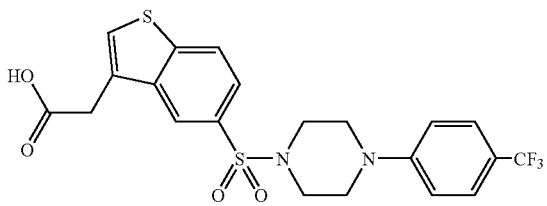

{5-[4-(4-Trifluoromethyl-phenyl)-piperazine-1-sulfonyl]-benzo[b]thiophen-3-yl}-acetic-acid: The compound {5-[4-(4-trifluoromethyl-phenyl)-piperazine-1-sulfonyl]-benzo[b]thiophen-3-yl}-acetic acid was prepared followed the procedure for Example 37 using 1-(4-trifluoromethyl-phenyl)-piperazine. ¹H NMR (400 MHz, CDCl₃), δ 8.34 (s, 1H), 7.90 (d, 1H), 7.76 (d, 1H), 7.65 (s, 1H), 7.45 (d, 2H), 6.85 (d, 2H), 3.94 (s, 2H), 3.34 (m, 4H), 3.20 (m, 4H).

EXAMPLE 42

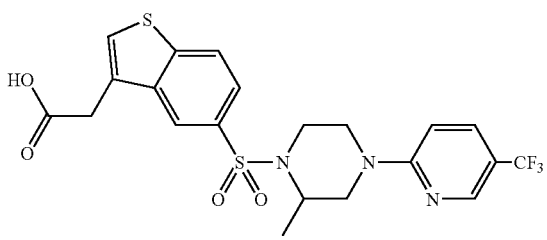

{5-[2-Methyl-4-(5-trifluoromethyl-pyridin-2-yl)-piperazine-1-sulfonyl]-benzo[b]thiophen-3-yl}-acetic acid: The compound {5-[2-methyl-4-(5-trifluoromethyl-pyridin-2-yl)-piperazine-1-sulfonyl]-benzo[b]thiophen-3-yl}-acetic acid was prepared followed the procedure for Example 37 using 3-methyl-1-(5-trifluoromethyl-pyridin-2-yl)-piperazine. ¹H NMR (400 MHz, CDCl₃), δ 8.38 (s, 1H), 8.32 (s, 1H), 7.82 (m, 2H), 7.63 (s, 1H), 7.55 (d, 1H), 6.48 (d, 1H), 4.29 (m, 1H), 4.18 (d, 1H), 4.02 (d, 1H), 3.92 (s, 2H), 3.79 (d, 1H), 3.28 (m, 2H), 3.02 (t, 1H), 1.10 (d, 3H).

EXAMPLE 43

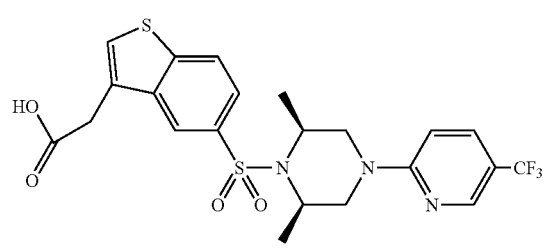

{5-[cis-2,6-Dimethyl-4-(5-trifluoromethyl-pyridin-2-yl)-piperazine-1-sulfonyl]-benzo[b]thiophen-3-yl}-acetic acid: The compound {5-[2,6-dimethyl-4-(5-trifluoromethyl-pyridin-2-yl)-piperazine-1-sulfonyl]-benzo[b]thiophen-3-yl}-acetic acid was prepared followed the procedure for Example 37 using cis-2,6-dimethyl-4-(5-trifluoromethyl-pyridin-2-yl)-piperazine. ¹H NMR (400 MHz. CDCl₃), δ 8.37 (s, 1H), 8.29 (s, 1H), 7.81 (m, 2H), 7.62 (s, 1H), 7.52 (d, 1H), 6.44 (d, 1H), 4.27 (m, 2H), 3.96 (t, 2H), 3.91 (s, 2H), 3.03 (dd, 2H), 1.39 (d, 6H).

EXAMPLE 44

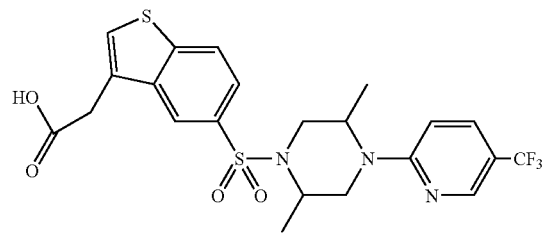

{5-[2,5-Dimethyl-4-(5-trifluoromethyl-pyridin-2-yl)-piperazine-1-sulfonyl]-benzo[b]thiophen-3-yl}-acetic acid: The compound {5-[2,5-dimethyl-4-(5-trifluoromethyl-pyridin-2-yl)-piperazine-1-sulfonyl]-benzo[b]thiophen-3-yl}-acetic acid was prepared followed the procedure for Example 37 using 2,5-Dimethyl-4-(5-trifluoromethyl-pyridin-2-yl)-piperazine. ¹H NMR (400 MHz, CDCl₃), δ 8.39 (s, 1H), 8.37 (s, 1H), 7.87 (d, 1H), 7.79 (d, 1H), 7.64 (s, 1H), 7.61 (d, 1H), 6.57

(d, 1H), 4.63 (m, 1H), 4.31 (m, 1H), 4.05 (d, 1H), 3.94 (s, 2H), 3.61 (d, 1H), 3.37 (m, 2H), 1.21 (d, 3H), 0.96 (d 3H).

EXAMPLE 45

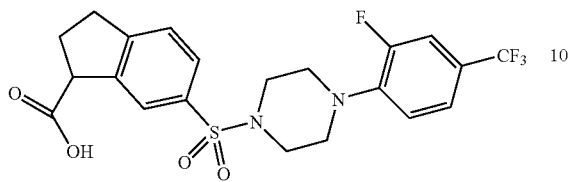

6-[4-(2-Fluoro-4-trifluoromethyl-phenyl)-piperazine-1-sulfonyl]-indan-1-carboxylic acid: The compound 6-[4-(2-fluoro-4-trifluoromethyl-phenyl)-piperazine-1-sulfonyl]-indan-1-carboxylic acid was synthesized according to the procedure described in Example 26. $^1$H NMR (400 MHz, CD$_3$OD) δ 7.83 (s, 1H), 7.65 (dd, 1H), 7.51 (d, 1H), 7.38 (d, 1H), 7.32 (dd, 1H), 7.14-7.10 (m, 1H), 4.15 (t, 1H), 3.30-3.20 (m, 4H), 3.20-3.15 (m, 1H), 3.14-3.10 (m, 4H), 3.09-2.96 (m, 1H), 2.49 (q, 2H); LCMS 472.5 (M+1)$^+$.

EXAMPLE 46

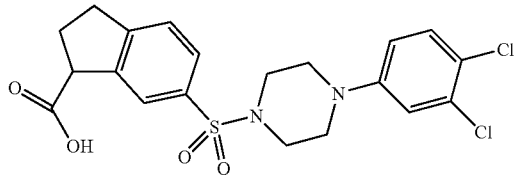

6-[4-(3,4-Dichloro-phenyl)-piperazine-1-sulfonyl]-indan-1-carboxylic acid: The compound 6-[4-(3,4-dichloro-phenyl)-piperazine-1-sulfonyl]-indan-1-carboxylic acid was synthesized according to the procedure described in Example 26. $^1$H NMR (400 MHz, CD$_3$OD) δ 7.84 (s, 1H), 7.70 (d, 1H), 7.54 (d, 1H), 7.34-7.29 (m, 1H), 7.10-7.06 (m, 1H), 6.90-6.84 (m, 1H), 4.38 (t, 1H), 3.30-3.22 (m, 4H), 3.21-3.25 (m, 1H), 3.24-3.10 (m, 4H), 3.20-2.99 (m, 1H), 2.50 (q, 2H); LCMS 455.5 (M+1)$^+$.

EXAMPLE 47

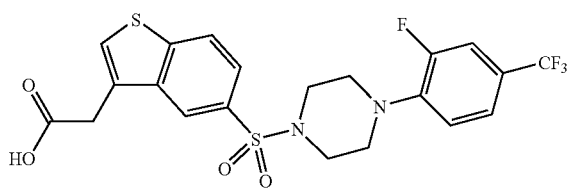

{5-[4-(2-Fluoro-4-trifluoromethyl-phenyl)-piperazine-1-sulfonyl]-benzo[b]thiophen-3-yl}-acetic acid Step 1

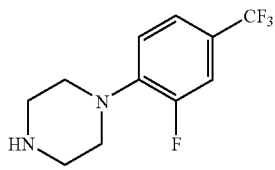

1-(2-Fluoro-4-trifluoromethyl-phenyl)-piperazine: The compound 1-(2-fluoro-4-trifluoromethyl-phenyl)-piperazine is synthesized according to the procedure outlined in Example 26 steps 1 and 2 using t-butyl-1-piperazine-carboxylate and 1-bromo-2-fluoro-4-trifluoromethyl-benzene.

Step 2

{5-[4-(2-Fluoro-4-trifluoromethyl-phenyl)-piperazine-1-sulfonyl]-benzo[b]thiophen-3-yl}-acetic acid: The compound {5-[4-(2-fluoro-4-trifluoromethyl-phenyl)-piperazine-1-sulfonyl]-benzo[b]thiophen-3-yl}-acetic acid was synthesized according to the procedure in Example 37 using 1-(2-Fluoro-4-trifluoromethyl-phenyl)-piperazine obtained in step 1 above. $^1$H NMR (400 MHz, CD$_3$OD) δ 8.44 (s, 1H), 8.04 (d, 1H), 7.82 (s, 1H), 7.78 (dd, 1H), 7.46-7.38 (m, 1H), 6.80-8.72 (m, 2H), 3.98 (s, 2H), 3.42-3.32 (m, 4H), 3.19-3.10 (m, 4H); LCMS 502.5 (M+1)$^+$.

EXAMPLE 48

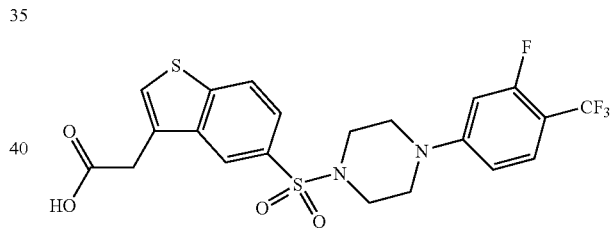

{5-[4-(3-Fluoro-4-trifluoromethyl-phenyl)-piperazine-1-sulfonyl]-benzo[b]thiophen-3-yl}-acetic acid: The compound {5-[4-(3-fluoro-4-trifluoromethyl-phenyl)-piperazine-1-sulfonyl]-benzo[b]thiophen-3-yl}-acetic acid was synthesized according to the procedure described in Example 47. $^1$H NMR (400 MHz, CD$_3$OD) δ 8.40 (s, 1H), 8.10 (d, 1H), 7.81 (s, 1H), 7.78 (dd, 1H), 7.46-7.39 (m, 1H), 6.80-8.72 (m, 2H), 4.00 (s, 2H), 3.40-3.31 (m, 4H), 3.18-3.10 (m, 4H); LCMS 502.5 (M+1)$^+$.

EXAMPLE 49

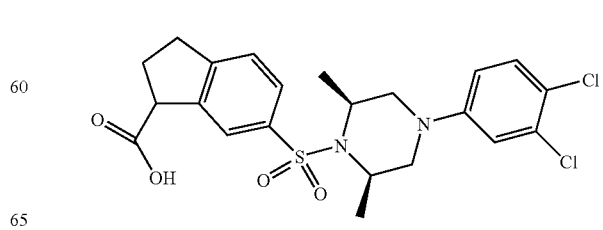

6-[4-(3,4-Dichloro-phenyl)-cis-2,6-dimethyl-piperazine-1-sulfonyl]-indan-1-carboxylic acid: The compound 6-[4-(3,4-dichloro-phenyl)-2,6-cis-dimethyl-piperazine-1-sulfonyl]-indan-1-carboxylic acid was synthesized according to the procedure described in Example 26 Steps 1 and 3 using 2,6-cis-dimethyl-piperazine and 4-bromo-1,2-dichloro-benzene. $^1$H NMR (400 MHz, CD$_3$OD) δ 7.83 (d, 1H), 7.67-7.62 (m,1H), 7.38 (dd, 1H), 7.19 (d, 1H), 6.82 (d, 1H), 6.65 (dd, 1H), 4.30-4.21 (m, 1H), 4.20-4.10 (m, 2H), 3.25-3.20 (m, 2H), 3.19-3.10 (m, 1H), 3.08-2.89 (m, 1H), 2.65-2.56 (m, 2H), 2.45-2.39 (m, 2H), 1.48 (d, 3H), 1.45 (d, 3H); LCMS 483.4 (M+1)$^+$.

EXAMPLE 50

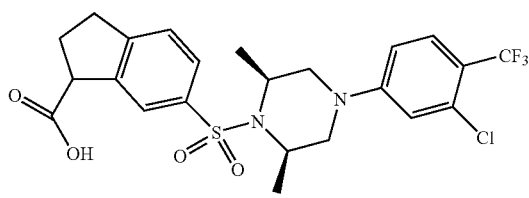

6-[4-(3-Chloro-4-trifluoromethyl-phenyl)-cis-2,6-dimethyl-piperazine-1-sulfonyl]-indan-1-carboxylic acid: The compound 6-[4-(3-Chloro-4-trifluoromethyl-phenyl)-cis-2,6-dimethyl-piperazine-1-sulfonyl]-indan-1-carboxylic acid was synthesized according to the procedure described in Example 26 Steps 1 and 3 using 2,6-cis-dimethyl-piperazine and 4-bromo-2-chloro-1-trifluoromethyl-benzene. $^1$H NMR (400 MHz, CD$_3$OD) δ 7.87 (s, 1H), 7.69 (d, 1H), 7.45 (d, 1H), 7.38 (d, 1H), 6.85 (s, 1H), 6.72 (d, 1H), 4.28-4.21 (m, 1H), 4.18-4.10 (m, 1H), 4.08 (t, 1H), 3.48-3.40 (m, 1H), 3.38-3.18 (m, 3H), 3.10-2.89 (m, 2H), 2.48-2.38 (m, 2H), 1.42 (m, 3H) 1.40 (d, 3H); LCMS 516.9 (M+1)$^+$.

EXAMPLE 51

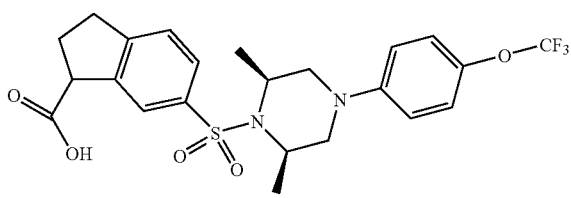

6-[cis-2,6-Dimethyl-4-(4-trifluoromethoxy-phenyl)-piperazine-1-sulfonyl]-indan-1-carboxylic acid: The compound 6-[2,6-cis-dimethyl-4-(4-trifluoromethoxy-phenyl)-piperazine-1-sulfonyl]-indan-1-carboxylic acid was synthesized according to the procedure described in Example 26 Steps 1 and 3 using cis-2,6-dimethyl-piperazine and 1-bromo-4-trifluoromethoxy-benzene. $^1$H NMR (400 MHz, CD$_3$OD) δ 7.84 (s, 1H), 7.70 (d, 1H), 7.40 (d, 1H), 7.10 (d, 2H), 6.89 (d, 2H), 4.30-4.20 (m, 1H), 4.19-4.09 (m, 2H), 3.30-3.20 (m, 2H), 3.19-3.10 (m, 1H), 3.08-2.98 (m, 1H), 2.65-2.56 (m, 2H), 2.45-2.39 (m, 2H), 1.50 (d, 3H), 1.45 (d, 3H); LCMS 498.5 (M+1)$^+$.

EXAMPLE 52

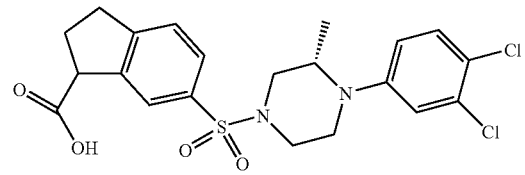

6-[4-(3,4-Dichloro-phenyl)-3-(S)-methyl-piperazine-1-sulfonyl]-indan-1-carboxylic acid: The compound 6-[4-(3,4-dichloro-phenyl)-3-(S)-methyl-piperazine-1-sulfonyl]-indan-1-carboxylic acid was synthesized according to the procedure described in Example 26 using 3-(S)-methyl-piperazine-1-carboxylic acid tert-butyl ester and 4-bromo-1,2-dichloro-benzene. $^1$H NMR (400 MHz, CD$_3$OD) δ 7.88 (s, 1H), 7.65 (d, 1H), 7.45 (d, 1H), 7.32 (d, 1H), 7.15-6.94 (m, 1H), 6.78-6.72 (m, 1H), 4.20-4.10 (m, 1H), 4.10-4.00 (m, 2H), 3.70-3.60 (m, 1H), 3.45-3.40 (m, 1H), 3.30-3.21 (m, 2H), 3.20-3.11 (m, 1H), 3.10-2.90 (m, 1H), 2.75-2.60 (m, 1H) 2.48-2.40 (m, 2H), 1.20 (d, 3H); LCMS 469.4 (M+1)$^+$.

EXAMPLE 53

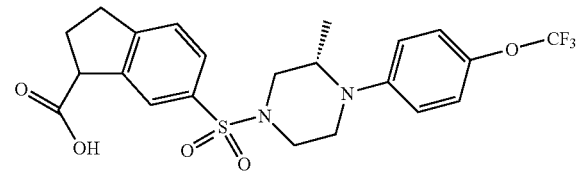

6-[3-(S)-Methyl-4-(4-trifluoromethoxy-phenyl)-piperazine-1-sulfonyl]-indan-1-carboxylic acid: The compound 6-[3-(S)-methyl-4-(4-trifluoromethoxy-phenyl)-piperazine-1-sulfonyl]-indan-1-carboxylic acid was synthesized according to the procedure described in Example 26 using 3-(S)-methyl-piperazine-1-carboxylic acid tert-butyl ester and 1-bromo-4-trifluoromethoxy-benzene. $^1$H NMR (400 MHz, CD$_3$OD) δ 7.81 (s, 1H), 7.66 (d, 1H), 7.50 (d, 1H), 7.62 (d, 2H), 6.98-6.93 (m, 2H), 4.18 (t, 1H), 4.00-3.90 (m, 1H), 3.60-3.55 (m, 1H), 3.35-3.25 (m, 3H), 3.20-3.10 (m, 1H), 3.10-3.00 (m, 1H), 2.85-2.75 (m, 1H), 2.70-2.60 (m, 1H) 2.40 (q, 2H), 1.10 (d, 3H); LCMS 484.5 (M+1)$^+$.

EXAMPLE 54

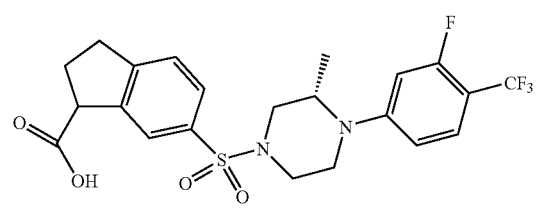

6-[4-(3-Fluoro-4-trifluoromethyl-phenyl)-3-(S)-Methyl-piperazine-1-sulfonyl]-indan-1-carboxylic acid: The compound 6-[4-(3-Fluoro-4-trifluoromethyl-phenyl)-3-(S)-Methyl-piperazine-1-sulfonyl]-indan-1-carboxylic acid was synthesized according to the procedure described in Example 26 using 3-(S)-methyl-piperazine-1-carboxylic acid tert-butyl ester. $^1$H NMR (400 MHz, CD$_3$OD) δ 7.80 (s, 1H), 7.70 (d, 1H), 7.50 (d, 1H), 7.41-7.31 (m, 2H), 7.20-7.10 (m, 1H), 4.20-4.10 (m, 1H), 3.90-3.78 (m, 1H), 3.50-3.40 (m, 1H), 3.39-3.20 (m, 3H), 3.19-3.10 (m, 1H), 3.09-2.98 (m, 2H), 2.80-2.70 (m, 1H), 2.42-2.25 (m, 2H), 1.10 (d, 3H); LCMS 486.5 (M+1)$^+$.

EXAMPLE 55

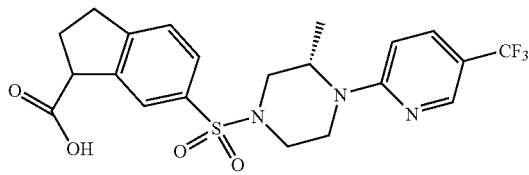

6-[3-(S)-Methyl-4-(5-trifluoromethyl-phenyl-pyridin-2-yl))-piperazine-1-sulfonyl]-indan-1-carboxylic acid: The compound 6-[3-(S)-methyl-4-(5-trifluoromethyl-phenyl-pyridin-2-yl))-piperazine-1-sulfonyl]-indan-1-carboxylic acid was synthesized according to the procedure described in Example 26 using 3-(S)-methyl-piperazine-1-carboxylic acid tert-butyl ester and 2-bromo-5-trifluoromethyl-pyridine. $^1$H NMR (400 MHz, CD$_3$OD) δ 8.38 (s, 1H), 7.83 (s 1H), 7.78-7.72 (m, 1H), 7.65 (d, 1H), 7.50-7.40 (m, 1H), 6.85-6.80 (m, 1H), 4.80-4.70 (m, 1H), 4.30 (d, 1H), 4.20-4.10 (m, 2H), 3.81 (d, 1H), 3.60 (d, 1H), 2.35-2.24 (m, 1H), 3.20-3.11 (m, 1H), 3.10-2.98 (m, 1H), 2.60-2.45 (m, 1H) 2.42-2.25 (m, 2H), 1.40-1.20 (m, 3H); LCMS 469.5 (M+1)$^+$.

EXAMPLE 56

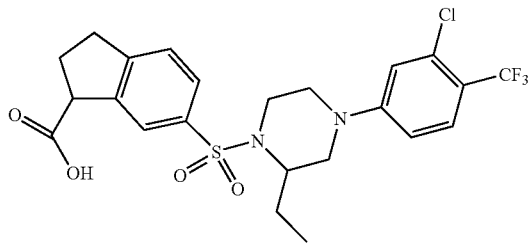

6-[4-(3-Chloro 4-trifluoromethyl-phenyl)-2-ethyl-piperazine-1-sulfonyl]-indan-1carboxylic acid: The compound 6-[4-(3-chloro-4-trifluoromethyl-phenyl)-2-ethyl-piperazine-1-sulfonyl]-indan-1carboxylic acid was synthesized according to the procedure described in Example 26 Steps 1 and 3 using 2-ethyl-piperazine and 4-bromo-2-chloro-1-trifluoromethyl-benzene. $^1$H NMR (400 MHz, CD$_3$OD) δ 7.90 (d, 1H), 7.72 (t, 1H), 7.45 (dd, 1H), 7.38 (dd, 1H), 6.87 (dd, 1H), 6.70 (dd, 1H), 4.12-4.02 (m, 1H), 4.01-3.93 (m, 1H), 3.98-3.76 (m, 1H), 3.58-3.42 (m, 2H), 3.41-3.29 (m, 1H), 3.11-3.02 (m, 1H), 3.00-2.82 (m, 2H), 2.82-2.62 (m, 1H), 2.46-2.36 (m, 2H), 1.76-1.56 (m, 2H), 1.00-0.92 (m 3H); LCMS 516.9 (M+1)$^+$.

EXAMPLE 57

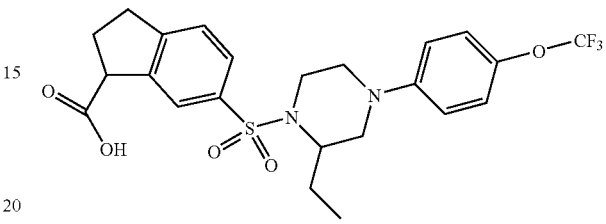

6-[2-Ethyl-4-(4-trifluoromethoxy-phenyl)-piperazine-1-sulfonyl]-indan-1-carboxylic acid: The compound 6-[2-ethyl-4-(4-trifluoromethoxy-phenyl)-piperazine-1-sulfonyl]-indan-1-carboxylic acid was synthesized according to the procedure described in Example 26 Steps 1 and 3 using 2-ethyl-piperazine and 1-bromo-4-trifluoromethoxy-benzene. $^1$H NMR (400 MHz, CD$_3$OD) δ 7.90 (s, 1H), 7.79-7.73 (m, 1H), 7.47-7.38 (m, 1H), 7.08 (d, 2H), 6.88-6.81 (m, 2H), 4.12 (q, 1H), 3.99-3.90 (m, 1H), 3.88-3.76 (m, 1H), 3.44-3.24 (m, 3H), 3.16-3.08 (m, 1H), 3.02-2.92 (m, 1H), 2.69-2.50 (m, 2H), 2.48-2.36 (m, 2H), 1.82-1.66 (m, 2H), 0.95 (t, 3H); LCMS 498.5 (M+1)$^+$.

EXAMPLE 58

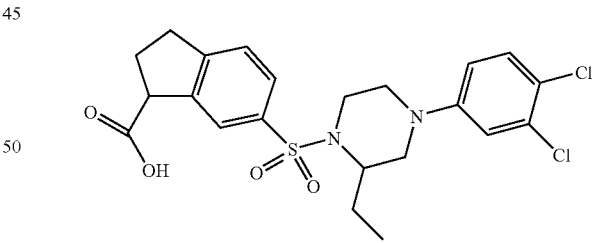

6-[4-(3,4-Dichloro-phenyl)-2-ethyl-piperazine-1-sulfonyl]-indan-1-carboxylic acid: The compound 6-[4-(3,4-Dichloro-phenyl)-2-ethyl-piperazine-1-sulfonyl]-indan-1-carboxylic acid was synthesized according to the procedure described in Example 26 Steps 1 and 3 using 2-ethyl-piperazine and 4-bromo-1,2-dichloro-benzene. $^1$H NMR (400 MHz, CD$_3$OD) δ 7.84 (s, 1H), 7.68-7.64 (m, 1H), 7.39-7.32 (m, 1H), 7.19 (dd, 1H), 6.82 (dd, 1H), 6.68-6.62 (m, 1H), 4.10 (q, 1H), 3.98-3.83 (m, 1H), 3.81-3.71 (m, 1H), 3.30-3.20 (m, 3H), 3.12-3.02 (m, 1H), 3.00-2.90 (m, 1H), 2.70-2.60 (m, 2H), 2.40-2.30 (m, 2H), 1.55-1.51 (m, 2H), 0.98 (t, 3H); LCMS 483.4 (M+1)+.

EXAMPLE 59

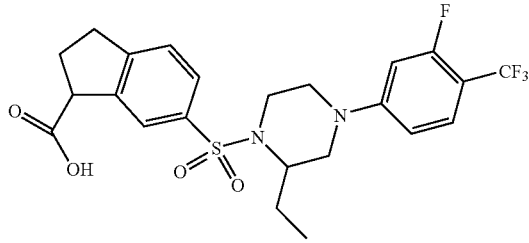

6-[2-Ethyl-4-(3-fluoro-4-trifluoromethyl-phenyl)-piperazine-1-sulfonyl]-indan-1-carboxylic acid: The compound 6-[2-Ethyl-4-(3-fluoro-4-trifluoromethyl-phenyl)-piperazine-1-sulfonyl]-indan-1-carboxylic acid was synthesized according to the procedure described in Example 26 Steps 1 and 3 using 2-ethyl -piperazine. $^1$H NMR (400 MHz, CD$_3$OD) δ 8.10 (s, 1H), 7.98-7.83 (m, 1H), 7.79 (d, 1H), 7.51-7.48 (m, 1H), 6.71-6.60 (m, 2H), 4.09-3.91 (m, 2H), 3.86-3.76 (m, 1H), 3.60-3.44 (m, 2H), 3.30-3.20 (m, 1H), 3.14-3.01 (m, 1H), 2.98-2.88 (m, 2H), 2.80-2.62 (m, 1H), 2.52-2.46 (m, 2H), 1.74-1.58 (m, 2H), 0.98-0.90 (m, 3H); LCMS 500.5 (M+1)+.

EXAMPLE 60

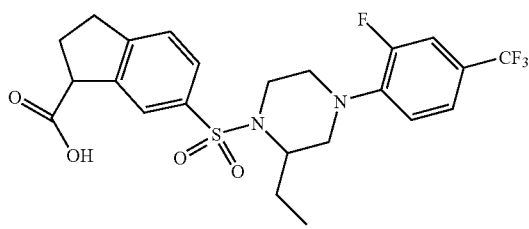

6-[2-Ethyl-4-(2-fluoro-4-trifluoromethyl-phenyl)-piperazine-1-sulfonyl]-indan-1-carboxylic acid: The compound 6-[2-Ethyl-4-(2-fluoro-4-trifluoromethyl-phenyl)-piperazine-1-sulfonyl]-indan-1-carboxylic acid was synthesized according to the procedure described in Example 26 Steps 1 and 3 using 2-ethyl -piperazine and 1-bromo-2-fluoro-4-trifluoromethyl-benzene. $^1$H NMR (400 MHz, CD$_3$OD) δ 7.91 (s, 1H), 7.78-7.70 (m, 1H), 7.50-7.40 (m, 1H), 7.36-7.28 (m, 2H), 7.10-6.99 (m, 1H), 4.12 (t, 1H), 4.00-3.80 (m, 2H), 3.50-3.22 (m, 3H), 3.20-3.15 (m, 1H), 3.14-3.05 (m, 1H), 2.75-2.50 (m, 2H), 2.45 (q, 2H), 1.72-1.50 (m, 2H), 1.01-0.95 (m, 3H); LCMS 500.5 (M+1)+.

EXAMPLE 61

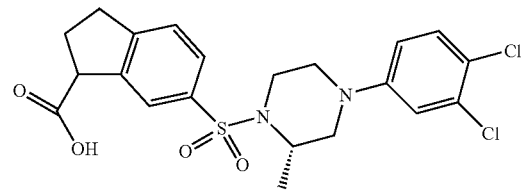

6-[4-(3,4-Dichloro-phenyl)-(S)-methyl-piperazine-1-sulfonyl]-indan-1-carboxylic acid: The compound 6-[4-(3,4-Dichloro-phenyl)-(S)-methyl-piperazine-1-sulfonyl]-indan-1-carboxylic acid was synthesized according to the procedure described in Example 26 Steps 1 and 3 using 2-(S)-methyl-piperazine and 4-bromo-1,2-dichloro-benzene. $^1$H NMR (400 MHz, CD$_3$OD) δ 7.88 (s, 1H), 7.74-7.68 (m, 1H), 7.41 (t, 1H), 7.28-7.24 (m, 1H), 6.94 (dd 1H), 6.78-6.72 (m, 1H), 4.22-4.14 (m, 1H), 4.13-4.07 (m, 1H), 3.78-3.70 (m, 1H), 3.50-3.40 (m, 1H), 3.16-3.04 (m, 2H), 3.02-2.92 (m, 1H), 2.90-2.84 (m, 1H), 2.76-2.64 (m, 2H), 2.46-2.32 (m, 2H), 1.02 (d, 3H); LCMS 469.4 (M+1)+.

EXAMPLE 62

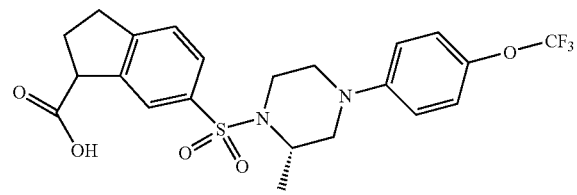

6-[2-(S)-Methyl-4-(4-trifluoromethoxy-phenyl)-piperazine-1-sulfonyl]-indan-1-carboxylic acid: The compound 6-[2-(S)-Methyl-4-(4-trifluoromethoxy-phenyl)-piperazine-1-sulfonyl]-indan-1-carboxylic acid was synthesized according to the procedure described in Example 26 Steps 1 and 3 using 2-(S)-methyl -piperazine and 1-bromo-4-trifluoromethoxy-benzene. $^1$H NMR (400 MHz, CD$_3$OD) δ 7.89 (s, 1H), 7.73-7.69 (m, 1H), 7.45-7.40 (m, 1H), 7.11-7.06 (m, 2H), 6.92-6.87 (m, 2H), 4.22-4.16 (m, 1H), 4.13-4.07 (m, 1H), 3.78-3.70 (m, 1H), 3.51-3.41 (m, 1H), 3.16-3.06 (m, 2H), 3.02-2.92 (m, 1H), 2.86-2.79 (m, 1H), 2.73-2.61 (m, 2H), 2.45-2.38 (m, 2H), 1.20 (d, 3H); LCMS 484.5 (M+1)+.

EXAMPLE 63

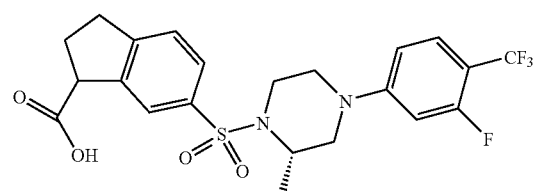

6-[4-(3-Fluoro-4-trifluoromethyl-phenyl)-2-(S)-methyl-piperazine-1-sulfonyl]-indan-1-carboxylic acid: The compound 6-[4-(3-Fluoro-4-trifluoromethyl-phenyl)-2-(S)-methyl-piperazine-1-sulfonyl]-indan-1-carboxylic acid was synthesized according to the procedure described in Example 26 Steps 1 and 3 using 2-(S)-methyl-piperazine. $^1$H NMR (400 MHz, CD$_3$OD) δ 7.87 (d, 1H), 7.71-7.62 (m, 1H), 7.41-7.32 (m, 2H), 6.68-6.58 (m, 2H), 4.23-4.16 (m, 1H), 4.14-4.02 (m, 1H), 3.80-3.69 (m, 1H), 3.66-3.47 (m, 1H), 3.43-3.34 (m, 2H), 3.12-3.01 (m, 2H), 2.99-2.80 (m, 2H), 2.45-2.36 (m, 2H), 1.20-1.00 (m, 3H); LCMS 486.5 (M+1)$^+$.

EXAMPLE 64

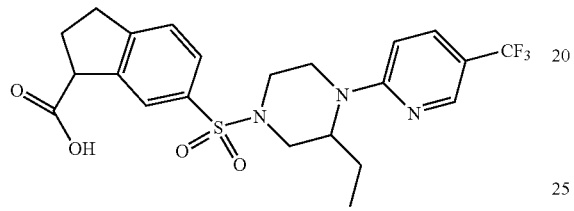

6-[3-Ethyl-4-(5-trifluoromethyl-pyrdin-2-yl)-piperazine-1-sulfonyl]-indan-1-carboxylic acid: The compound 6-[3-Ethyl-4-(5-trifluoromethyl-pyrdin-2-yl)-piperazine-1-sulfonyl]-indan-1-carboxylic acid was synthesized according to the procedure described in Example 26 using 3-ethyl-piperazine-1-carboxylic acid tert-butyl ester and 2-bromo-5-trifluoromethyl-pyridine. $^1$H NMR (400 MHz, CD$_3$OD) δ 8.30 (s, 1H), 7.80 (s, 1H), 7.69-7.60 (m, 2H), 7.50-7.40 (m, 1H) 6.90-6.80 (m, 1H), 4.60-4.50 (m, 1H), 4.43-4.35 (m, 1H), 4.15-4.05 (m, 1H), 3.80 (d, 2H), 3.35-3.20 (m, 2H), 3.19-3.10 (m, 1H), 3.10-3.00 (m, 1H), 2.50-2.40 (m, 3H), 1.99-1.60 (m, 2H), 1.01-0.93 (m, 3H); LCMS 483.5 (M+1)$^+$.

EXAMPLE 65

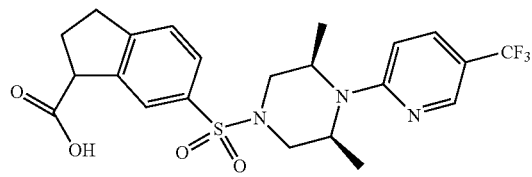

6-[cis-3,5-Dimethyl-4-(5-trifluoromethyl-pyrdin-2-yl)-piperazine-1-sulfonyl]-indan-1-carboxylic acid: The compound 6-[cis-3,5-dimethyl-4-(5-trifluoromethyl-pyrdin-2-yl)-piperazine-1-sulfonyl]-indan-1-carboxylic acid was synthesized according to the procedure described in Example 26 using 3,5-cis-dimethyl-piperazine-1-carboxylic acid tert-butyl ester and 2-bromo-5-trifluoromethyl-pyridine. $^1$H NMR (400 MHz, CD$_3$OD) δ 8.05 (s, 1H), 7.51 (s, 1H), 7.40-7.30 (m, 2H), 7.18 (d, 1H) 6.46 (d, 1H), 4.35-4.25 (m, 1H), 3.25 (t, 1H), 3.41-3.32 (m, 1H), 3.08-3.02 (m, 2H), 2.98-2.88 (m, 1H), 2.86-2.78 (m, 1H), 2.74-2.64 (m, 1H), 2.24-2.16 (m, 1H), 2.15-2.08 (m, 2H), 1.03 (d, 3H), 1.02 (d, 3H); LCMS 483.5 (M+1)$^+$.

EXAMPLE 66

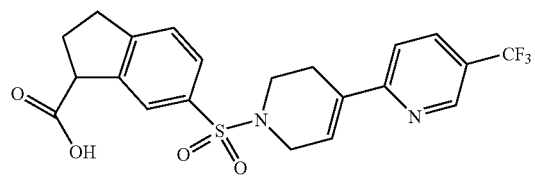

6-(5-Trifluoromethyl-3,6-dihydro-2H-[2,4]bipyridinyl-1-sulfonyl)-indan-1-carboxylic acid Step 1

A solution of 2-iodo-5-trifluoromethylpyridine (2.2 g, 8.0 mmol) and pyridyl-4-boronic acid (1.0 g, 8.8 mmol) in MeOH (8 mL) and toluene (30 mL) was purged with nitrogen for 5 min followed by addition of Pd(PPh$_3$)$_4$ (0.2 g) and aqueous 2M Na$_2$CO$_3$ (4 mL). The mixture was then heated to reflux for 7 h. After cooling the reaction mixture to room temperature, solids were removed by filtration and the filtrate was concentrated in vacuo. The residue was dissolved in EtOAc (20 mL) and washed with brine. The organic solution was concentrated in vacuo and purified by column chromatography to give the desired compound (0.4 g) as a light yellow powder.

Step 2

To a solution of the compound from Step 1 (0.23 g 1.1 mmol) in DMF (10 mL) was added benzyl bromide (0.2 g, 1.2 mmol). The mixture was then heated at 95° C. for 8 h. After cooling the reaction mixture to room temperature, ether (500 mL) was added slowly and the mixture was stirred overnight. A light yellow crystalline product was removed by filtration and dried to give the desired compound (0.2 g).

Step 3

To a solution of the product from Step 2 (0.2 g) in MeOH (10 mL) at −52° C. was added NaBH$_4$ (0.1 g). The reaction mixture was stirred for 30 min. The reaction mixture was concentrated in vacuo. The residue was dissolved in ether (10 mL) and washed with water (10 mL). After drying over anhydrous sodium sulfate, the solvent was removed to give the desired compound (150 mg) as a yellow solid.

Step 4

To a solution of the product from Step 3 (150 mg) in CH$_2$Cl$_2$ (10 mL) at −52° C. was added ethyl chloroformate (0.3 g) dropwise. The mixture was stirred at 0° C. for 40 min. The reaction mixture was concentrated in vacuo. The residue was dissolved in MeOH (10 mL) and heated to reflux for 1 h. The reaction mixture was cooled to room temperature and concentrated in vacuo. The residue was dissolved in CH$_2$Cl$_2$ (20 mL) and triethylamine (0.5 mL), and methyl 2-(5-chlorosulfonyl-2-methylphenyl)acetate (0.3 g) were added. After stirring at room temperature overnight, the mixture was washed with brine (3×20 mL), dried over Na$_2$SO$_4$ and concentrated in vacuo. The residue was purified by column chromatography to afford the desired compound (100 mg) as a white solid.

Step 5

To a solution of the product from Step 4 (100 mg) in THF at 0° C. was added a 2M NaOH solution (2 mL) dropwise. The reaction mixture was warmed to room temperature and stirred until all the starting material was consumed. The reaction mixture was concentrated in vacuo. The residue was acidified to pH 3 with 2M HCl and extracted with EtOAc. The organic solution was dried over $Na_2SO_4$, the solvent was concentrated in vacuo to give the title compound (60 mg). $^1$H NMR (400 MHz, $CD_3OD$) δ 8.77 (s, 1H), 8.04-8.00 (m, 1H), 7.88 (s, 1H), 7.73-7.64 (m, 2H), 7.47 (d, 1H) 6.78 (s, 1H), 4.13 (t, 1H), 3.85-3.81 (m, 1H), 3.36-3.27 (m, 2H), 3.14-3.05 (m, 2H), 3.04-2.93 (m, 1H), 2.75-2.67 (m, 2H), 2.42 (q, 2H); LCMS 452.5 (M+1)$^+$.

EXAMPLE 67

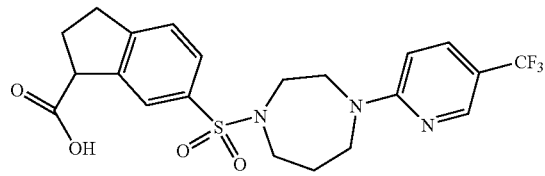

6-[4-(5-Trifluoromethyl-pyridin-2-yl)-[1,4]diazepane-1-sulfonyl]-indan-1-carboxylic acid: The compound 6-[4-(5-trifluoromethyl-pyridin-2-yl)-[1,4]diazepane-1-sulfonyl]-indan-1-carboxylic acid was synthesized according to the procedure described in Example 23 using [1,4]diazepane and 2-bromo-5-trifluoromethyl-pyridine. $^1$H NMR (400 MHz, $CD_3OD$) δ 8.26 (s, 1H), 7.81 (s, 1H), 7.66-7.56 (m, 2H), 7.25 (d, 1H), 6.65 (d, 1H), 4.06 (t, 1H), 3.92-3.86 (m, 1H), 3.84-3.76 (m, 1H), 3.75-3.70 (m, 1H), 3.54-3.44 (m, 2H), 3.38-3.24 (m, 3H), 3.10-3.02 (m, 1H), 2.98-2.88 (m, 1H), 2.48-2.36 (m, 2H), 1.96-1.88 (m, 2H); LCMS 469.5 (M+1)$^+$.

EXAMPLE 68

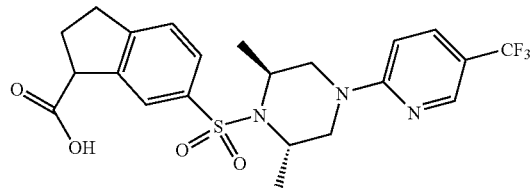

6-[trans-2,6-(S,S)-Dimethyl-4-(5-trifluoromethyl-pyrdin-2-yl)-piperazine-1-sulfonyl]-indan-1-carboxylic acid: The compound 6-[trans-2,6-(S,S)-dimethyl-4-(5-trifluoromethyl-pyrdin-2-yl)-piperazine-1-sulfonyl]-indan-1-carboxylic acid was synthesized according to the procedure described in Example 26 Steps 1 & 3 using 2,6-(S,S)-dimethyl-piperazine and 2-bromo-5-trifluoromethyl-pyridine. $^1$H NMR (mixture of diastereomers ~1:1, 400 MHz, $CD_3OD$) δ 8.25 (s, 1H), 8.24 (s, 1H) 7.95 (s, 1H), 7.90 (s, 1H), 7.70-7.60 (m, 4H), 7.35 (d, 1H) 7.25 (d, 1H), 6.70 (d, 1H) 6.50 (d, 1H), 4.30-4.19 (m, 4H), 4.15 (t, 1H) 4.01 (t, 1H), 3.80-3.60 (m, 4H), 3.62- 3.52 (m, 2H), 3.43-3.25 (m, 2H), 3.15-2.80 (m, 4H), 2.25-2.15 (m, 4H), 1.38 (d, 6H), 1.30 (d, 6H); LCMS 483.8 (M+1)$^+$.

EXAMPLE 69

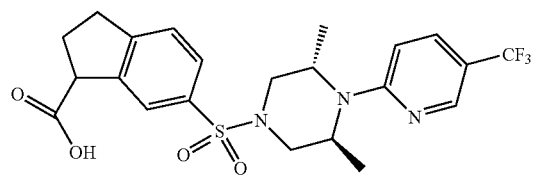

6-[trans-3,5-(S,S)Dimethyl-4-(5-trifluoromethyl-pyrdin-2-yl)-piperazine-1-sulfonyl]-indan-1-carboxylic acid: The compound 6-[trans-3,5-(S,S)-dimethyl-4-(5-trifluoromethyl-pyrdin-2-yl)-piperazine-1-sulfonyl]-indan-1-carboxylic acid was synthesized according to the procedure described in Example 26 using 3,5-(S,S)-dimethyl-piperazine-1-carboxylic acid tert-butyl ester and 2-bromo-5-trifluoromethyl-pyridine. $^1$H NMR (400 MHz, $CD_3OD$) δ 8.38-8.30 (m, 1H), 7.90 (s, 1H), 7.80-7.65 (m, 2H), 7.45 (d, 1H) 6.65 (d, 1H), 4.65-4.55 (m, 1H), 4.43-4.32 (m, 2H), 4.20-4.10 (m, 1H) 3.70-3.58 (m, 3H), 3.20-3.10 (m, 1H), 3.09-3.00 (m, 1H), 2.58-2.38 (m, 2H), 1.05 (d, 3H), 1.02 (d, 3H); LCMS 483.5 (M+1)$^+$.

EXAMPLE 70

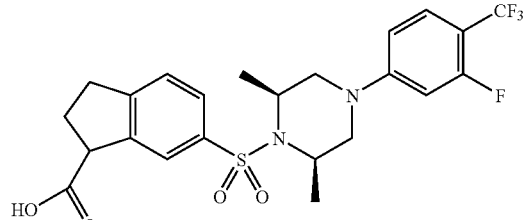

6-[cis-2,6-Dimethyl-4-(3-fluoro-4-trifluoromethyl-phenyl)-piperazine-1-sulfonyl]-indan-1-carboxylic acid: The compound 6-[cis-2,6-dimethyl-4-(3-fluoro-4-trifluoromethyl-phenyl)-piperazine-1-sulfonyl]-indan-1-carboxylic acid was synthesized according to the procedure outlined in Example 63 using 3,5-cis-dimethyl-piperazine. $^1$H NMR (400 MHz, $CD_3OD$) δ 7.87 (s, 1H), 7.70 (dd, 1H), 7.38-7.34 (m, 2H), 6.62 (s, 1H), 6.59 (d, 1H), 4.26-4.22 (m, 1H), 4.16-

4.10 (m, 1H), 4.08 (t, 1H), 3.47 (d, 2H), 3.10-3.02 (m, 1H), 2.97-2.88 (m, 3H), 2.40 (q, 2H), 1.42 (d, 3H), 1.40 (d, 2H).

1H), 3.32-3.20 (m, 1H), 3.16-2.82 (m, 4H), 2.54-2.38 (m, 2H), 1.62-1.48 (m, 2H), 0.90 (q, 3H); LCMS 484.0(M+1)⁺.

EXAMPLE 71

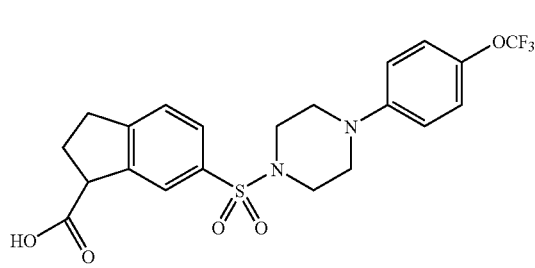

6-[4-(4-Trifluoromethoxy-phenyl)-piperazine-1-sulfonyl]-indan-1-carboxylic acid: The compound 6-[4-(4-trifluoromethoxy-phenyl)-piperazine-1-sulfonyl]-indan-1-carboxylic acid was synthesized according to the procedure outlined in Example 26 using 1-(4-trifluoromethoxy-phenyl)-piperazine. ¹H NMR (400 MHz, CDCl₃) δ 7.85 (s, 1H), 7.66 (dd, 1H), 7.41 (d, 1H), 7.12 (d, 2H), 6.95 (d, 2H), 4.15 (t, 1H), 3.40-3.08 (m, 9H), 3.04-2.96 (m, 1H), 2.56-2.42 (m, 2H); LCMS 471.5 (M+1)⁺.

EXAMPLE 72

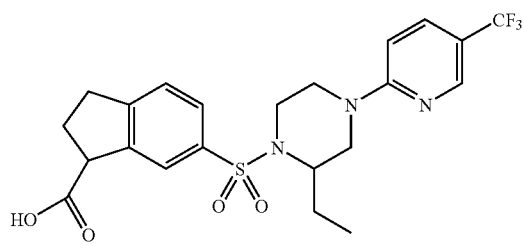

6-[2-Ethyl-4-(5-trifluoromethyl-pyridin-2-yl)-piperazine-1-sulfonyl]-indan-1-carboxylic acid: The compound 6-[2-ethyl-4-(5-trifluoromethyl-pyridin-2-yl)-piperazine-1-sulfonyl]-indan-1-carboxylic acid was synthesized according to the procedure outlined in Example 26 Step 1 (using 2-ethyl-piperazine and 2-chloro-5-trifluoromethyl-pyridine) and Step 3 (using 3-ethyl-1-(5-trifluoromethyl-pyridin-2-yl)-piperazine). ¹H NMR (400 MHz, CDCl₃) δ 8.32 (s, 1H), 7.92 (s, 1H), 7.72 (t, 1H), 7.58 (t, 1H), 7.36-7.31 (m, 1H), 6.54-6.48 (m, 1H), 4.20-4.05 (m, 3H), 3.99-3.93 (m, 1H), 3.85-3.73 (m,

EXAMPLE 73

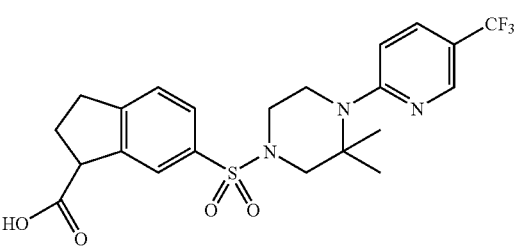

6-[3,3-Dimethyl-4-(5-trifluoromethyl-pyridin-2-yl)-piperazine-1-sulfonyl]-indan-1-carboxylic acid: The compound 6-[3,3-dimethyl-4-(5-trifluoromethyl-pyridin-2-yl)-piperazine-1-sulfonyl]-indan-1-carboxylic acid was synthesized according to the procedure outlined in Example 26 using 2,2-dimethyl-1-(5-trifluoromethyl-pyridin-2-yl)-piperazine. ¹H NMR (400 MHz, CDCl₃) δ 8.47 (s, 1H), 7.85 (s, 1H), 7.66-7.62 (m, 2H), 7.40 (d, 1H), 6.86 (d, 1H), 4.15 (t, 1H), 3.61 (br s, 2H), 3.25-3.12 (m, 3H), 3.05-2.96 (m, 1H), 2.92 (s, 2H), 2.57-2.41 (m, 2H), 1.44 (s, 6H); LCMS 483.9 (M+1)⁺.

EXAMPLE 74

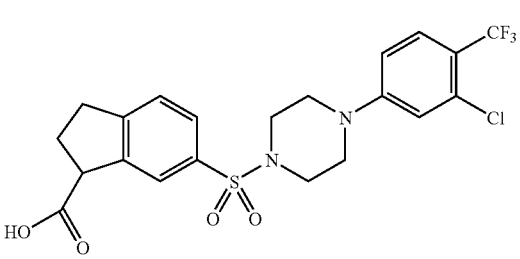

6-[4-(3-Chloro-4-trifluoromethyl-phenyl)-piperazine-1-sulfonyl]-indan-1-carboxylic acid: The compound 6-[4-(3-chloro-4-trifluoromethyl-phenyl)-piperazine-1-sulfonyl]-indan-1-carboxylic acid was synthesized according to the procedure outlined in Example 26 using 1-(3-Chloro-4-trifluoromethyl-phenyl)-piperazine. ¹H NMR (400 MHz, CDCl₃) δ 7.83 (s, 1H), 7.65 (d, 1H), 7.47 (d, 1H), 7.41 (d, 1H), 6.86 (d, 1H), 6.70 (dd, 1H), 4.17-4.11 (m, 1H), 3.36-3.33 (m, 4H), 3.19-3.10 (m, 5H), 3.04-2.96 (m, 1H), 2.54-2.41 (m, 2H); LCMS 489.5 (M+1)⁺.

EXAMPLE 75

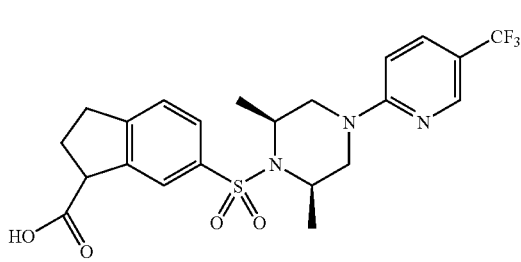

Single enantiomer of 6-[cis-2,6-Dimethyl-4-(5-trifluoromethyl-pyridin-2-yl)-piperazine-1-sulfonyl]-indan-1-carboxylic acid: This single enantiomer of 6-[cis-2,6-dimethyl-4-(5-trifluoromethyl-pyridin-2-yl)-piperazine-1-sulfonyl]-indan-1-carboxylic acid was obtained by chiral HPLC (chiralcel OD-H 0.46×15 cm Hex/IPA 96:4 (v/v) with 0.1% TFA, flow rate 1 mL/min) separation from the racemate. LCMS 482.1 (M−1)⁻.

EXAMPLE 76

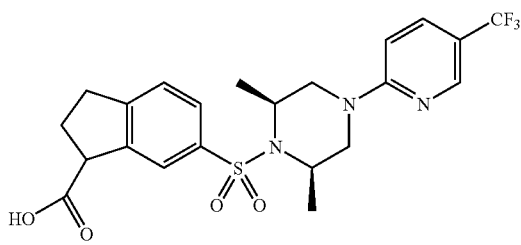

Single enantiomer of 6-[cis-2,6-Dimethyl-4-(5-trifluoromethyl-pyridin-2-yl)-piperazine-1-sulfonyl]-indan-1-carboxylic acid: This single enantiomer of 6-[cis-2,6-dimethyl-4-(5-trifluoromethyl-pyridin-2-yl)-piperazine-1-sulfonyl]-indan-1-carboxylic acid was obtained by chiral HPLC (chiralcel OD-H 0.46×15 cm Hex/IPA 96:4 (v/v) with 0.1% TFA, flow rate 1 ml/min) separation from the racemate. LCMS 482.0 (M−1)⁻.

EXAMPLE 77

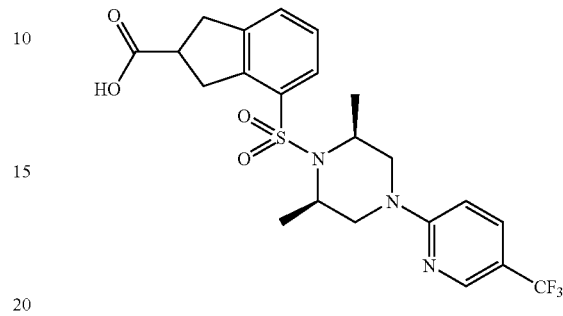

4-[cis-2,6-Dimethyl-4-(5-trifluoromethyl-pyridin-2-yl)-piperazine-1-sulfonyl]-indan-2-carboxylic acid Step 1 cis-3,5-Dimethyl-1-(5-trifluoromethyl-pyridin-2-yl)-piperazine: The compound cis-3,5-dimethyl-1-(5-trifluoromethyl-pyridin-2-yl)-piperazine was synthesized according to the procedure described in Example 26 using cis-2,6 dimethyl piperazine.

Step 2

4-[cis-2,6-Dimethyl-4-(5-trifluoromethyl-pyridin-2-yl)-piperazine-1-sulfonyl]-indan-2-carboxylic acid: The compound 4-[cis-2,6-dimethyl-4-(5-trifluoromethyl-pyridin-2-yl)-piperazine-1-sulfonyl]-indan-2-carboxylic acid was synthesized according to the procedure outlined in Example 79 using methyl-4-chlorosulfonyl-2-carboxylate and cis-3,5-dimethyl-1-(5-trifluoromethyl-pyridin-2-yl)-piperazine obtained from Step 1 above. ¹H NMR (400 MHz, CDCl₃) δ 8.35 (s, 1H), 7.74 (d, 1H), 7.61 (dd, 1H), 7.41 (d, 1H), 7.30 (t, 1H), 6.58 (d, 1H), 4.40-4.30 (m, 4H), 3.66-3.53 (m, 2H), 3.45-3.35 (m, 1H), 3.31-3.28 (m, 2H), 3.13 (dd, 1H), 3.05 (dd, 1H), 1.41 (d, 3H), 1.40 (dd, 3H); LCMS 483.8 (M+1)⁺.

EXAMPLE 78

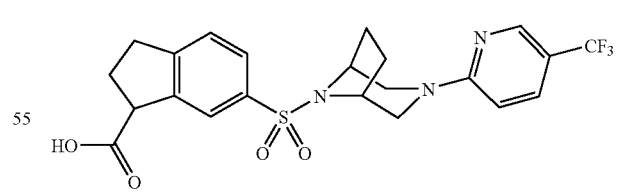

4-[2,6-Dimethyl-4-(4-trifluoromethoxy-phenyl)-piperazine-1-sulfonyl]-indan-2-carboxylic acid: The compound 4-[2,6-Dimethyl-4-(4-trifluoromethoxy-phenyl)-piperazine-1-sulfonyl]-indan-2-carboxylic acid was synthesized according to the procedure outlined in Example 26 using 3,8-diazabicyclo[3.2.1]octane-8-carboxylic acid tert-butyl ester and 2-chloro-5-trifluoromethyl-pyridine. ¹H NMR (400 MHz, CD₃OD) δ 8.33 (s, 1H), 7.94 (s, 1H), 7.79 (dd, 1H), 7.72 (dd, 1H), 7.46 (d, 1H), 6.79 (d, 1H), 4.40-4.30 (m, 3H), 3.17-3.09 (m, 3H), 3.05-2.97 (m, 2H), 2.43 (q, 2H), 1.60-1.36 (m, 4H); LCMS 482.5 (M+1)+.

EXAMPLE 79

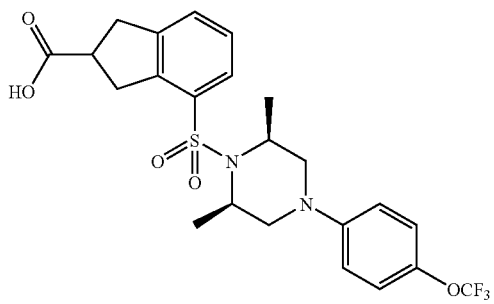

4-[cis-2,6-Dimethyl-4-(4-trifluoromethoxy-phenyl)-piperazine-1-sulfonyl]-indan-2-carboxylic acid Step 1

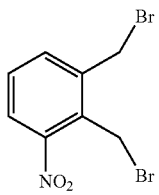

1,2-Bis(bromomethyl)-3-nitrobenzene: A 1 liter flask was charged with 1,2-dimethyl-3-nitrobenzene (20 g, 0.13 mol), N-bromosuccinimide (50 g, 0.28 mol), azobis(isobutyronitrile) (5 g, 3.0 mmol), and 200 mL of dichloromethane. This was irradiated with a 120 watt floodlamp to affect gentle reflux under nitrogen for 18 hours. The mixture was then cooled and precipitated succinimide was removed by filtration. The filtrate was concentrated and the residue was purified by chromatography on silica (5%-50% CH$_2$Cl$_2$ in hexanes) to give 2.6 g white solid (64%).

Step 2

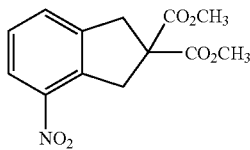

Dimethyl-4-nitroindane-2,2-dicarboxylate: To a solution stirred under nitrogen at room temperature, to 5.0 mL methanol in 15.0 mL ether was added 60% sodium hydride (0.84 g, 0.021 mol) in small portions. After the addition was complete, the nearly clear and colorless solution was stirred for 5 minutes. To it was then added 1.3 g dimethyl malonate, giving a slightly cloudy colorless solution. To this was rapidly added a suspension of 3.1 g 1,2-bis(bromomethyl)-3-nitrobenzene, which immediate gave a precipitate suspended in a dark green solution. This was removed by filtation and the filtrate was concentrated. The residue was purified on silica (20%-100% CH$_2$Cl$_2$ in hexanes) to give 1.93 g off-white solid (67%).

Step 3

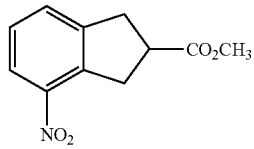

Methyl-4-nitroindane-2-carboxylate: A mixture of dimethyl-4-nitroindane-2,2-dicarboxylate (4.84 g, 0.0167 mol), lithium chloride (0.84 g, 0.0198 mol), 1.1 mL water, and 18 mL dimethylsulfoxide was heated to 160° C. under nitrogen for two hours. It was then allowed to cool and the dimethylsulfoxide was removed under high vacuum. The residue was purified on silica (10%-100% CH$_2$Cl$_2$ in hexanes) to give 2.5 g white solid (65%).

Step 4

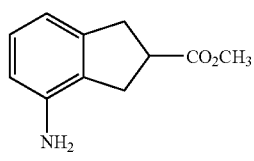

Methyl-4-aminoindane-2-carboxylate: A mixture of methyl-4-nitroindane-2-carboxylate (2.4 g, 0.11 mol) and 10% palladium on carbon (1.1 g, 0.01 mol) in ethyl acetate (15 mL) was shaken under 55 PSI hydrogen for 1 hour. It was then filtered and the filtrate was concentrated to give 2.07 g white solid (100%).

Step 5

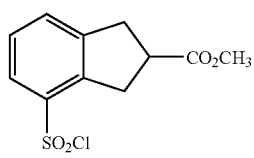

Methyl 4-chlorosulfonyl-indan-2-carboxylate: A mixture of methyl-4-aminoindane-2-carboxylate (2.5 g, 0.013 mol), 12.5 mL acetonitrile, and 12.5 mL H$_2$O was cooled to −5° C. in an ice-salt bath. To this was added 2.6 mL concentrated HCl (0.014 mol). To this was added dropwise over 20 minutes a solution of 1.0 g sodium nitrite (0.021 mol) in 5 mL water. After the addition was complete the solution was stirred for 20 minutes. It was then transferred to a jacketed addition funnel cooled with ice water. The solution was added dropwise to a solution stirred under nitrogen at 55° C. of 4.2 g potassium thioxanthate (0.026 mol) in 20 mL H$_2$O. As the addition took place, a dark layer rose to the top of the diazonium ion solution which was not added. After the addition was complete the mixture was stirred at 55° C. for 30 minutes, then was allowed to cool and was extracted with 40 mL ethyl acetate. The organic layer was dried (MgSO$_4$) and concentrated. The residue was loaded on 80 mL silica gel which was slurry-packed in hexanes. This was eluted with 100 mL hexanes, then 1%-50% CH$_2$Cl$_2$ in hexanes in 50 mL fractions to give 1.3 g amber oil (33%).

A mixture of 3.6 g of the above compound in 30 mL CCl₄ and 10 mL H₂O was vigorously stirred and cooled to 3 C. Chlorine gas was bubbled through at such a rate that the temperature stayed below 10° C. After conversion was complete, the phases were separated and the aqueous layer was extracted with CH₂Cl₂. The combined organic layers were dried (MgSO₄) and concentrated to give 4.0 g yellow oil (100%).

Step 6

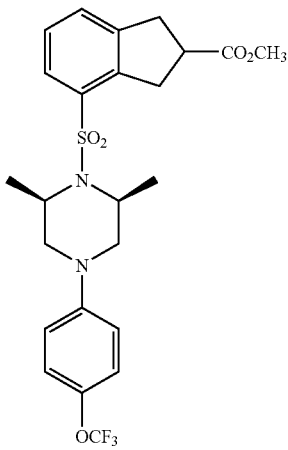

4-[cis-2,6-Dimethyl-4-(4-trifluoromethoxy-phenyl)-piperazine-1-sulfonyl]-indan-2-methyl ester: A mixture of methyl 4-chlorosulfonyl-indan-2-carboxylate (2.13 g, 0.0078 mol) obtained from Step 6, cis-3,5-dimethyl-1-(4-trifluoromethoxy-phenyl)-piperidine (3.0 g, 0.0109 mol) obtained from Example 51, 20 mL acetonitrile, and 3.0 g K₂CO₃ (0.0217 mol) was heated to 60° C. under nitrogen with stirring for 20 hours. It was then filtered and the filtrate was concentrated. The residue was purified by chromatography on silica (5%-50% EtOAc in hexanes) to give 2.64 g viscous yellow oil (66%).

Step 7

4-[cis-2,6-Dimethyl-4-(4-trifluoromethoxy-phenyl)-piperazine-1-sulfonyl]-indan-2-carboxylic acid: To a solution of 4-[cis-2,6-dimethyl-4-(4-trifluoromethoxy-phenyl)-piperazine-1-sulfonyl]-indan-2-methyl ester (2.64 g, 0.0052 mol) in the minimum amount of THF (ca 15 mL) was added a solution of 0.14 g LiOH (0.0057 mol) in the minimum amount of water (ca 2.5 mL). This was capped and stirred at room temperature for 12 hours. Examination by HPLC showed the reaction was 85% complete so an additional 0.020 g LiOH (0.125 eq total) was added and stirring was continued for 3 hours. It was then concentrated to remove THF and partitioned between EtOAc and water. The aqueous layer was treated with 0.54 mL conc. HCl. It was then extracted with ethyl acetate. The organic layer was dried (MgSO₄) and concentrated to give 2.38 g yellow amorphous solid (93%).

EXAMPLE 80

A single enantiomer of Example 79 was obtained by chiral HPLC (chiralpak ASH 0.46×15 cm Hex/IPA 94:6 (v/v) with 0.1% TFA, flow rate 1 ml/min) separation from the racemate. LCMS 497.1 (M−1)⁻.

EXAMPLE 81

A single enantiomer of Example 79 was obtained by chiral HPLC (chiralpak ASH 0.46×15 cm Hex/IPA 94:6 (v/v) with 0.1% TFA, flow rate 1 ml/min) separation from the racemate. LCMS 497.1 (M−1)⁻.

EXAMPLE 82

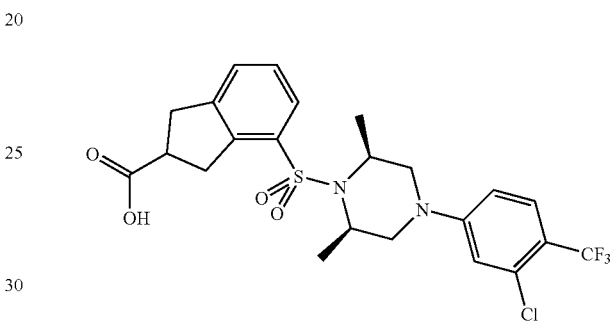

4-[4-(3-Chloro-4-trifluoromethyl-phenyl)-cis-2,6-dimethyl-piperazine-1-sulfonyl]-indan-2-carboxylic acid: The compound 4-[4-(3-chloro-4-trifluoromethyl-phenyl)-cis-2,6-dimethyl-piperazine-1-sulfonyl]-indan-2-carboxylic acid was synthesized by coupling methyl-4-chlorosulfonyl-2-carboxylate obtained from Example 79 Step 5 and 1-(3-chloro-4-trifluoromethyl-phenyl)-cis-3,5-dimethyl-piperazine used in Example 50. ¹H NMR (400 MHz, CD₃OD) δ 7.70 (d, 1H), 7.50-7.42 (m, 2H), 7.32 (t, 1H), 6.94 (d, 1H) 6.82 (m, 1H), 4.25-4.18 (m, 1H), 4.11-4.01 (m, 1H) 3.62-3.52 (m, 4H), 3.41-3.32 (m, 1H), 3.29-3.24 (m, 2H), 3.03 (dd, 1H), 2.94 (m, 1H) 1.45 (d, 3H), 1.43 (d, 3H); LCMS 517.0 (M+1)⁺.

EXAMPLE 83

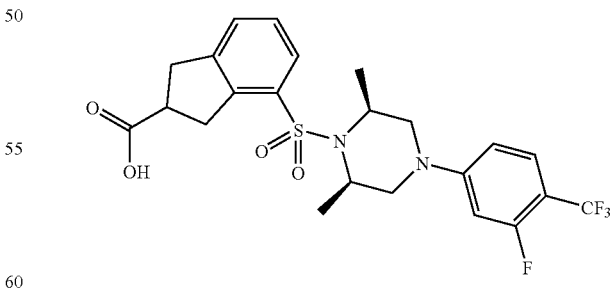

4-[4-(3-Fluoro-4-trifluoromethyl-phenyl)-cis-2,6-dimethyl-piperazine-1-sulfonyl]-indan-2-carboxylic acid: The compound 4-[4-(3-fluoro-4-trifluoromethyl-phenyl)-cis-2,6-dimethyl-piperazine-1-sulfonyl]-indan-2-carboxylic acid was synthesized in a similar fashion as described in Example 82. ¹H NMR (400 MHz, CD₃OD) δ 7.20 (d, 1H), 7.40 (d, 1H), 7.44-7.32 (m, 2H), 6.74 (s, 1H) 6.72-6.67 (m, 1H), 4.26-4.20 (m, 1H), 4.10-4.02 (m, 1H) 3.66-3.58 (m, 2H), 3.54 (d, 2H), 3.42-3.34 (m, 2H), 3.30-3.25 (m, 1H), 3.01 (dd, 1H), 2.94 (m, 1H) 1.46 (d, 3H), 1.40 (d, 3H); LCMS 500.5 (M+1)+.

EXAMPLE 84

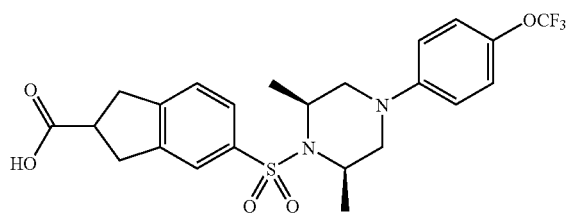

5-[cis-2,6-Dimethyl-4-(4-trifluoromethoxy-phenyl)-piperazine-1-sulfonyl]-indan-2-carboxylic acid: The compound 5-[2,6-cis-dimethyl-4-(4-trifluoromethoxy-phenyl)-piperazine-1-sulfonyl]-indan-2-carboxylic acid was synthesized according to the procedure outlined in Example 1 using indane-2-carboxylic acid methyl ester and cis-3,5-dimethyl-1-(4-trifluoromethoxy-phenyl)-piperazine (made by procedure outlined in Example 26 step 1 using 2,6-cis-dimethyl piperazine and 1-bromo-4-trifluoromethoxy-benzene). $^1$H NMR (400 MHz, CD$_3$OD) δ 7.72 (s, 1H), 7.66 (d, 1H), 7.37 (d, 1H), 7.09 (d, 2H), 6.87 (d, 2H), 4.22-4.12 (m, 2H), 3.41-3.25 (m, 7H), 2.64-2.58 (m, 2H), 1.46 (d, 6H); LCMS 499.5 (M+1)+.

EXAMPLE 85

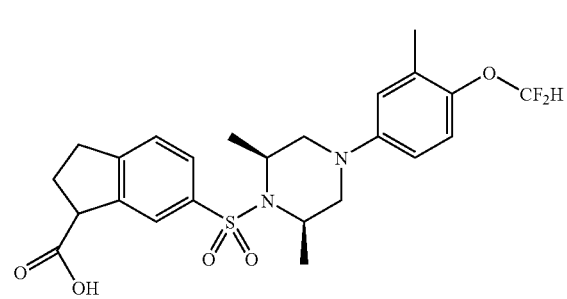

6-[4-(4-Difluoromethoxy-3-methyl-phenyl)-cis-2,6-dimethyl-piperazine-1-sulfonyl]-indan-1-carboxylic acid Step 1

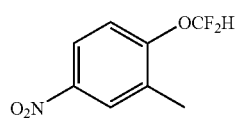

1-Difluoromethoxy-2-methyl-4-nitrobenzene: To a solution of 2-methyl-4-nitrophenol (14 g, 91.50 mmol) in dimethylformamide (120 mL) and water (25 mL) was added Cs$_2$CO$_3$ (41.8 g, 128.22 mmol), and sodium 2-chloro-2,2-difluoroacetate (32 g, 209.84 mmol). The resulting solution was stirred for 20 minutes at room temperature, then for an additional 3 hours at 100° C. The reaction solution was cooled to room temperature before the addition of 100 ml of H$_2$O. The resulting solution was extracted with EtOAc (4×100 ml) and the combined organic layers were washed with H$_2$O (2×150 mL), dried over Na$_2$SO$_4$, concentrated in vacuo. The residue was purified by silica gel column chromatography to provide 16 g (86%) of 1-(difluoromethoxy)-2-methyl-4-nitrobenzene.

Step 2

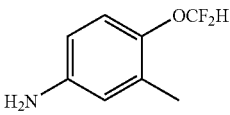

4-Amino-1-difluoromethoxy-2-methyl-benzene: To a solution of 1-(difluoromethoxy)-2-methyl-4-nitrobenzene (10 g, 48.28 mmol) in ethanol (150 mL) and water (150 mL) was added iron powder (12 g, 214.29 mmol). Acetic acid (cat. amount) was added dropwise with stirring and the reaction mixture was heated at reflux for 20 minutes. The mixture was cooled to room temperature and solids were removed by filtration. Volatiles were removed in vacuo and the aqueous solution was extracted with EtOAc (3×150 mL). The combined organic layers were dried over Na$_2$SO$_4$ and concentrated in vacuo to provide 8 g (95%) of 4-amino-1-difluoromethoxy-2-methyl-benzene.

Step 3

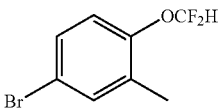

4-Bromo-1-difluoromethoxy-2-methyl-benzene: To a stirred solution of 4-amino-1-difluoromethoxy-2-methyl-benzene (5 g, 28.90 mmol) in HBr (20 mL) and water (20 mL) at 0° C. was added a solution of sodium nitrite (2.07 g, 30.00 mmol) in H$_2$O (10 ml) dropwise over a period of 20 minutes. After the addition was complete, the reaction mixture was stirred for 30 minutes at 0° C. Copper (1) bromide (4 g, 27.87 mmol) was then added and the mixture was heated at 60° C. for 30 minutes. The resulting solution was extracted with EtOAc (3×50 mL) and the combined organic layers washed with H$_2$O (1×20 mL), dried over Na$_2$SO$_4$ and concentrated to provide 2.5 g (37%) of 4-bromo-1-(difluoromethoxy)-2-methylbenzene.

Step 4

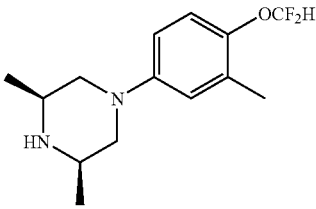

1-(4-Difluoromethoxy-3-methyl-phenyl)-cis-3,5-dimethyl-piperazine: To 4-bromo-1-(difluoromethoxy)-2-methylbenzene (2.36 g, 10.00 mmol) in toluene (50 mL) was added cis-2,6-dimethylpiperazine (5 g, 58.14 mmol), Pd(OAc)$_2$ (120 mg, 0.53 mmol), BINAP (380 mg, 0.61 mmol), and t-BuOK (2.2 g, 19.64 mmol). The resulting solution was stirred for 4 hours at 80° C. The solution was cooled to room temperature and washed with H$_2$O (2×50 mL), dried over Na$_2$SO$_4$, concentrated, and purified by silica gel column chromatography (10:1 CH$_2$Cl$_2$/MeOH) to give 1.1 g (41%) of 1-(4-(difluoromethoxy)-3-methylphenyl)-3,5-dimethylpiperazine.

Step 5

6-[4-(4-Difluoromethoxy-3-methyl-phenyl)-2,6-dimethyl-piperazine-1-sulfonyl]-indan-1-carboxylic acid: The compound 6-[4-(4-difluoromethoxy-3-methyl-phenyl)-2,6-dimethyl-piperazine-1-sulfonyl]-indan-1-carboxylic acid was prepared according to the procedure outlined in Example 1 using indane-1-carboxylic acid methyl ester. $^1$H NMR (CD$_3$OD) δ 7.82 (s, 1H), 7.72 (dd, 1H), 7.39 (dd, 1H), 6.93 (d, 1H), 6.72 (s, 1H), 6.65 (d, 1H), 6.60 (t, 1H), 4.15 (m, 2H), 3.69 (s, 2H), 3.22 (d, 2H), 3.09 (m, 1H), 2.97 (m, 1H) 2.58 (dd, 1H), 2.48 (dd, 1H), 2.42 (m, 2H), 2.19 (s, 3H), 1.45 (d, 6H).

EXAMPLE 86

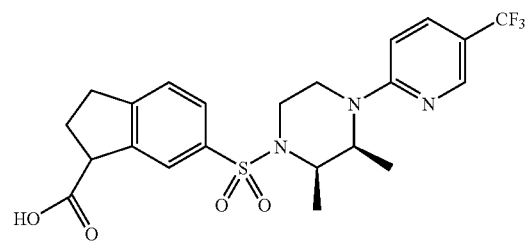

6-[2,3-Dimethyl-4-(5-trifluoromethyl-pyridin-2-yl)-piperazine-1-sulfonyl]-indan-1-carboxylic acid: The compound 6-[2,3-Dimethyl-4-(5-trifluoromethyl-pyridin-2-yl)-piperazine-1-sulfonyl]-indan-1-carboxylic acid was prepared according to the method described in the preparation of Example 23. $^1$H NMR (400 MHz, CDCl$_3$), δ (ppm): 8.33 (s, 1H), 7.85 (d, 1H), 7.62 (d, 1H), 7.56 (t, 1H), 7.29 (d, 1H), 6.43 (dd, 1H), 4.37 (m, 1H), 4.11 (m, 3H), 3.20 (m, 2H), 3.08 (m, 3H), 2.45 (m, 2H), 1.41 (dd, 3H, 1.18 (dd, 3H).

EXAMPLE 87

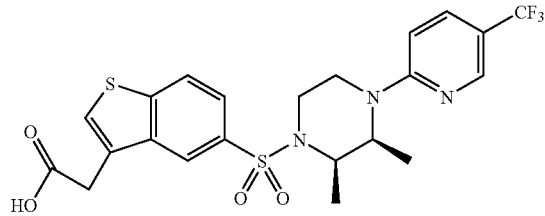

{5-[2,3-Dimethyl-4-(5-trifluoromethyl-pyridin-2-yl)-piperazine-1-sulfonyl]-benzo[b]thiophen-3-yl}-acetic acid: The compound {5-[2,3-Dimethyl-4-(5-trifluoromethyl-pyridin-2-yl)-piperazine-1-sulfonyl]-benzo[b]thiophen-3-yl}-acetic acid was prepared according to the method described in the preparation of Example 37. $^1$H NMR (400 MHz, CDCl$_3$), δ (ppm):): 8.29 (s, 1H), 8.28 (s, 1H), 7.76 (m, 2H), 7.59 (s, 1H), 7.48 (d, 1H), 6.34 (d, 1H), 4.39 (m, 1H), 3.98 (m, 2H), 3.88 (s, 2H), 3.37 (m, 1H), 3.25 (m, 1H), 3.15 (m, 1H), 1.44 (d, 3H), 1.18 (d, 3H).

EXAMPLE 88

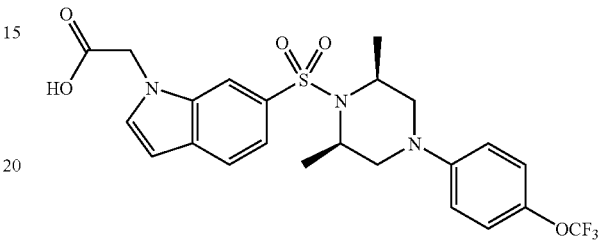

{6-[cis-2,6-Dimethyl-4-(4-trifluoromethoxy-phenyl)-piperazine-1-sulfonyl]-indol-1-yl}-acetic acid: The compound {6-[cis-2,6-Dimethyl-4-(4-trifluoromethoxy-phenyl)-piperazine-1-sulfonyl]-indol-1-yl}-acetic acid was synthesized according to the procedure outlined in Example 34 using cis-3,5-dimethyl-1-(4-trifluoromethoxy-phenyl)-piperazine from Example 51. $^1$H NMR (400 MHz, CD$_3$OD) δ7.89 (s, 1H), 7.71 (d, 1H), 7.52 (dd, 1H), 7.44 (d, 1H), 7.05 (d, 2H), 6.84 (d, 2H), 6.58 (d, 1H), 5.02 (s, 2H), 4.23-4.19 (m, 2H), 3.27 (d, 2H), 2.55 (dd, 2H), 1.46 (d, 6H); LCMS 512.6 (M+1)$^+$.

EXAMPLE 89

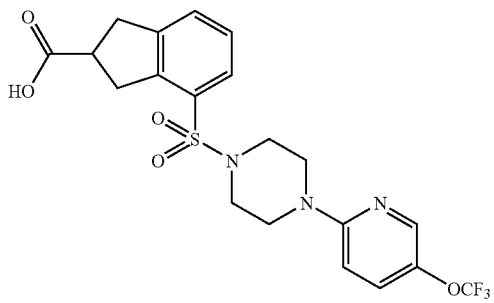

4-[4-(5-Trifluoromethoxy-pyridin-2-yl)-piperazine-1-sulfonyl]-indan-2-carboxylic acid. The compound 4-[4-(5-Trifluoromethoxy-pyridin-2-yl)-piperazine-1-sulfonyl]-indan-2-carboxylic acid was prepared according to the procedure outlined in Example 79 using 1-(5-trifluoromethoxy-pyridin-2-yl)-piperazine. $^1$H NMR (CD$_3$OD) δ 8.02 (d, 1H), 7.60 (d, 1H), 7.51 (d, 1H), 7.46 (m, 1H), 7.38 (t, 1H), 6.82 (d, 1H), 3.62 (m, 3H), 3.55 (d, 2H): 3.16 (m, 8H).

EXAMPLE 90

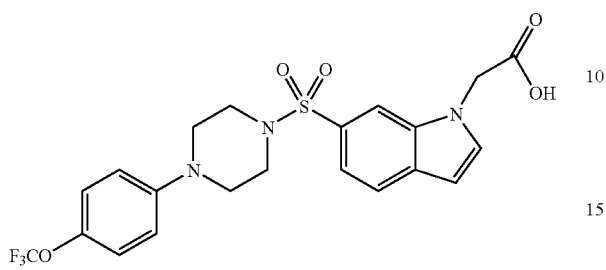

{6-[4-(4-Trifluoromethoxy-phenyl)-piperazine-1-sulfonyl]-indol-1-yl}-acetic acid. {6-[4-(4-Trifluoromethoxy-phenyl)-piperazine-1-sulfonyl]-indol-1-yl}-acetic acid methyl ester was prepared from 1-(4-trifluoromethoxy-phenyl)-piperazine following the procedures outlined in Example 34. A mixture of {6-[4-(4-trifluoromethoxy-phenyl)-piperazine-1-sulfonyl]-indol-1-yl}-acetic acid methyl ester (45 mg, 0.09 mmol), 1M LiOH (2 mL), tetrahydrofuran (6 mL), and methanol (2 mL) was stirred at rt for 3 h. The reaction was poured into 1M HCl (50 mL) and extracted with ethyl acetate (40 mL×2). The combined organic extracts were dried, filtered, and concentrated to give {6-[4-(4-trifluoromethoxy-phenyl)-piperazine-1-sulfonyl]-indol-1-yl}-acetic acid: $^1$H NMR (400 MHz, DMSO-d6): δ 7.89 (s, 1H), 7.77 (d, 1H), 7.63 (d, 1H), 7.38 (d, 1H), 7.14 (d, 2H), 6.93 (d, 2H), 6.61 (d, 1H), 5.19 (s, 2H), 3.23-3.15 (m, 4H), 3.03-2.95 (m, 4H); MS (ESI): 483.7 (M+H).

EXAMPLE 91

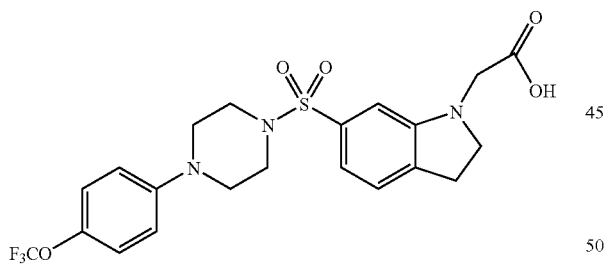

{6-[4-(4-Trifluoromethoxy-phenyl)-piperazine-1-sulfonyl]-2,3-dihydro-indol-1-yl}-acetic acid. Triethylsilane (0.13 mL, 0.77 mmol) was added to a solution of {6-[4-(4-trifluoromethoxy-phenyl)-piperazine-1-sulfonyl]-indol-1-yl}-acetic acid methyl ester (82 mg, 0.16 mmol) and trifluoroacetic acid (4 mL) at rt. After 1 H, more triethylsilane (0.2 mL, 1.2 mmol) was added. After an additional 4 H, the reaction was poured into 1.2 M NaOH (50 mL) and extracted with CH$_2$Cl$_2$ (3×30 mL). The combined organic extracts were dried, filtered, concentrated and purified by silica gel chromatography (4:1→3:2; hexanes:ethyl acetate) to give {6-[4-(4-trifluoromethoxy-phenyl)-piperazine-1-sulfonyl]-2,3-dihydro-indol-1-yl}-acetic acid methyl ester: MS (ESI): 500.1 (M+H). {6-[4-(4-Trifluoromethoxy-phenyl)-piperazine-1-sulfonyl]-2,3-dihydro-indol-1-yl}-acetic acid methyl ester was hydrolyzed following the procedure outlined in Example 1 Step 2 to give {6-[4-(4-trifluoromethoxy-phenyl)-piperazine-1-sulfonyl]-2,3-dihydro-indol-1-yl}-acetic acid: $^1$H NMR (400 MHz, DMSO-d6): δ 7.24 (d, 1H), 7.19 (d, 2H), 6.98 (d, 2H), 6.93 (d, 1H), 6.68 (s, 1H), 4.05 (s, 2H), 3.57 (t, 2H), 3.24-3.17 (m, 4H), 3.03 (t, 2H), 3.00-2.94 (m, 4H); MS (ESI): 486.1 (M+H).

EXAMPLE 92

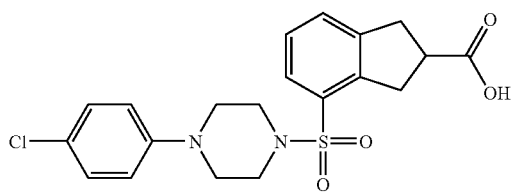

4-[4-(4-Chloro-phenyl)-piperazine-1-sulfonyl]-indan-2-carboxylic acid. The compound 4-[4-(4-chloro-phenyl)-piperazine-1-sulfonyl]-indan-2-carboxylic acid was prepared from 1-(4-chloro-phenyl)-piperazine and 4-chlorosulfonyl-indan-2-carboxylic acid methyl ester following the procedure outlined in Example 79. $^1$H NMR (400 MHz, DMSO-d6): δ 7.58 (d, 1H), 7.56 (d, 1H), 7.43 (t, 1H), 7.23 (d, 2H), 6.92 (d, 2H), 3.50-3.41 (m, 2H), 3.40-3.29 (m, 1H), 3.28-3.13 (m, 6H), 3.12-3.04 (m, 4H); MS (ESI): 420.9 (M+H).

EXAMPLE 93

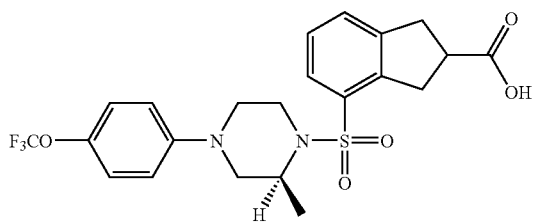

4-[2-(S)-Methyl-4-(4-trifluoromethoxy-phenyl)-piperazine-1-sulfonyl]-indan-2-carboxylic acid. The compound 4-[2-(S)-Methyl-4-(4-trifluoromethoxy-phenyl)-piperazine-1-sulfonyl]-indan-2-carboxylic acid was prepared from 3-(S)-methyl-1-(4-trifluoromethoxy-phenyl)-piperazine and 4-chlorosulfonyl-indan-2-carboxylic acid methyl ester following the procedure outlined in Example 79. $^1$H NMR (400 MHz, DMSO-d6): δ 7.65 (d, 1H), 7.53 (d, 1H), 7.38 (t, 1H), 7.18 (d, 2H), 6.98-6.92 (m, 2H), 4.15-4.00 (m, 1H), 3.60-3.12 (m, 9H), 2.83-2.75 (m, 1H), 2.64-2.50 (m, 1H), 1.18 (d, 3H); MS (ESI): 485.3 (M+H).

EXAMPLE 94

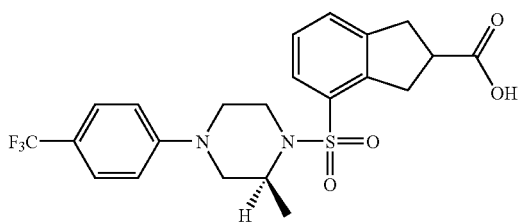

4-[2-(S)-Methyl-4-(5-trifluoromethyl-pyridin-2-yl)-piperazine-1-sulfonyl]-indan-2-carboxylic acid. The compound 4-[2-(S)-Methyl-4-(5-trifluoromethyl-pyridin-2-yl)-piperazine-1-sulfonyl]-indan-2-carboxylic acid was prepared from 3-(S)-methyl-1-(5-trifluoromethyl-pyridin-2-yl)-piperazine and 4-chlorosulfonyl-indan-2-carboxylic acid methyl ester following the procedure outlined in Example 79. $^1$H NMR (400 MHz, DMSO-d6): δ 8.3& (s, 1H), 7.82-7.76 (m, 1H), 7.65 (d, 1H), 7.52 (d, 1H), 7.37 (t, 1H), 6.93-6.88 (m, 1H), 4.35-4.18 (m, 2H), 4.18-4.02 (m, 1H), 3.60-3.46 (m, 1H), 3.45-3.10 (m, 7H), 2.97-2.80 (m, 1H), 1.06-1.01 (m, 3H); MS (ESI): 470.0 (M+H).

EXAMPLE 95

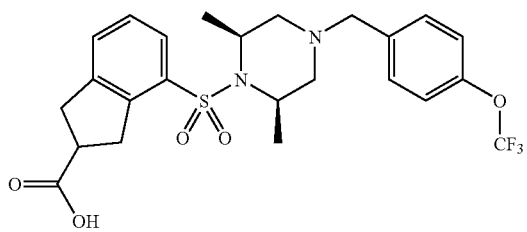

4-[cis-2,6-Dimethyl-4-(4-trifluoromethoxy-benzyl)-piperazine-1-sulfonyl]-indan-2-carboxylic acid Step 1

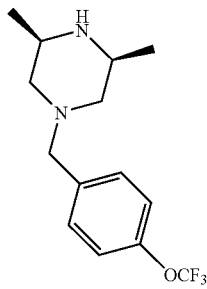

cis-3,5-Dimethyl-1-(4-trifluoromethoxy-benzyl)-piperazine: To a solution of 4-(trifluoromethoxy)-benzaldehyde (776 uL, 4.38 mmol) in methylene chloride (30 mL) was added cis-2,6-dimethyl piperazine (1.0 g, 8.77 mmol). After 1 hour sodium triacetoxy borohydride (2.45 g, 8.77 mmol) was added to the mixture. The solution was stirred at room temperature for an additional 4 hours. The reaction was concentrated in vacuo, diluted with ethyl acetate and extracted with 1N HCl (2×50 mL). The aqueous layer was then neutralized with NaOH and extracted with ethyl acetate (3×50 mL). The organic layer was dried (Na$_2$SO$_4$) and concentrated to provide cis-3,5-dimethyl-1-(4-trifluoromethoxy-benzyl)-piperazine (1.01 g, 80%). $^1$H NMR (400 MHz, CD$_3$OD) δ 7.42 (d, 2H), 7.23 (d, 2H), 3.54 (s, 2H), 2.98-2.88 (m, 2H), 2.82-2.74 (m, 2H), 1.69 (t, 2H), 1.05 (d, 6H); LCMS 289.5 (M+1)$^+$.

Step 2

4-[cis-2,6-Dimethyl-4-(4-trifluoromethoxy-benzyl)-piperazine-1-sulfonyl]-indan-2-carboxylic acid: The compound 4-[cis-2,6-dimethyl-4-(4-trifluoromethoxyl-benzyl)-piperazine-1-sulfonyl]-indan-2-carboxylic acid was synthesized according to the procedure in Example 79 using cis-3,5-dimethyl-1-(4-trifluoromethoxy-benzyl)-piperazine. $^1$H NMR (400 MHz, CD$_3$OD) δ 7.74-7.64 (m, 4H), 7.47 (d, 1H), 7.39-7.28 (m, 2H), 4.42 (s, 2H), 4.21-2.18 (m, 2H), 3.50-3.34 (m, 5H), 3.33-3.19 (m, 4H), 1-56 (d, 6H); LCMS 497.5 (M+1)$^+$.

EXAMPLE 96

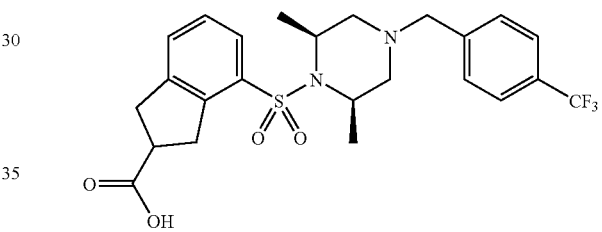

4-[cis-2,6-Dimethyl-4-(4-trifluoromethyl-benzyl)-piperazine-1-sulfonyl]-indan-2-carboxylic acid: The compound 4-[cis-2,6-dimethyl-4-(4-trifluoromethyl-benzyl)-piperazine-1-sulfonyl]-indan-2-carboxylic acid was synthesized according to the procedure in Example 95, using 4-(trifluoromethyl)-benzaldehyde. $^1$H NMR (400 MHz, CD$_3$OD) δ 7.78-7.62 (m, 5H), 7.47 (d, 1H), 7.32 (t, 1H), 4.41 (s, 2H), 4.21-2.15 (m, 2H), 3.52-3.36 (m, 5H), 3.34-3.22 (m, 4H), 1.52 (d, 6H); LCMS 497.5 (M+1)$^+$.

EXAMPLE 97

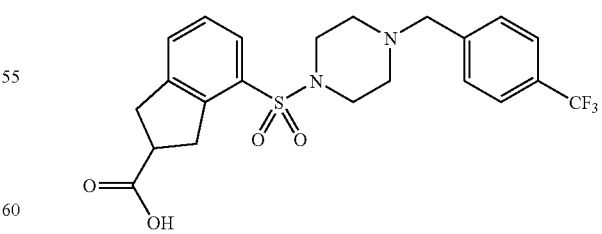

4-[4-(4-Trifluoromethyl-benzyl)-piperazine-1-sulfonyl]-indan-2-carboxylic acid: The compound 4-[4-(4-trifluoromethyl-benzyl)-piperazine-1-sulfonyl]-indan-2-carboxylic acid was synthesized according to the procedure in Example 95, using piperazine and 4-(trifluoromethyl)-benzaldehyde.

¹H NMR (400 MHz, CD₃OD) δ 7.82-7.73 (m, 4H), 7.62 (d, 1H), 7.54 (d, 1H), 7.38 (t, 1H), 4.47 (s, 2H), 3.54-3.48 (m, 5H), 3.46-3.35 (m, 2H), 3.32-3.22 (m, 6H); LCMS 469.5 (M+1)⁺.

EXAMPLE 98

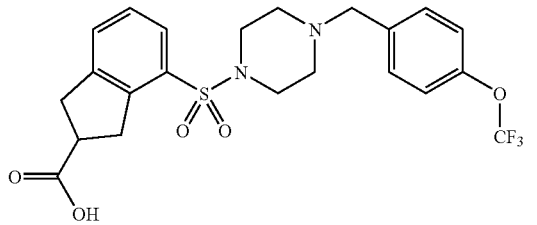

4-[4-(4-Trifluoromethoxy-benzyl)piperazine-1-sulfonyl]-indan-2-carboxylic acid: The compound 4-[4-(4-trifluoromethoxy-benzyl)-piperazine-1-sulfonyl]-indan-2-carboxylic acid was synthesized according to the procedure in Example 95, using piperazine. ¹H NMR (400 MHz, CD₃OD) δ 7.70-7.60 (m, 3H), 7.54 (d, 1H), 7.42-7.33 (m, 3H), 4.41 (s, 2H), 3.54-3.48 (m, 5H), 3.46-3.35 (m, 2H), 3.32-3.22 (m, 6H); LCMS 484.9 (M+1)⁺.

EXAMPLE 99

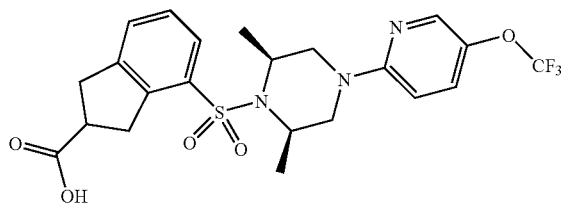

4-[cis-2,6-Dimethyl-4-(5-trifluoromethyl-pyridin-2-yl)-piperazine-1-sulfonyl]-indan-2-carboxylic acid Step 1

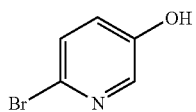

2-Bromo-pyridin-5-ol: To a solution of 6-bromopyridin-3-ylboronic acid (9.5 g, 43.48 mmol) in THF (180 mL) was added oxydol (8.8 g, 98.35 mmol) dropwise with stirring at 0° C. After 10 minutes, acetic acid (5.6 g, 93.33 mmol) was added dropwise with stirring at 0° C. The resulting solution was stirred overnight at room temperature. The product was precipitated after addition of NaHSO₃ and NaHCO₃. The resulting solution was extracted with EtOAc (3×80 mL) and the organic layers were combined and dried over MgSO₄. The solvent was concentrated to give 7 g (88%) of 2-bromo-pyridin-5-ol.

Step 2

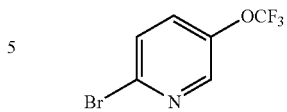

2-Bromo-5-trifluoromethoxy-pyridine: Into a 50 mL sealed tube was placed 6-bromopyridin-3-ol (2.5 g, 14.37 mmol), perchloromethane (6.6 g, 42.86 mmol) and antimony pentafloride (101 g, 465.44 mmol). The resulting solution was heated at 150° C. for 8 hours. After cooling to room temperature, the reaction mixture was poured into ice water and neutralized with saturated KOH. The resulting solution was extracted with EtOAc (100 ml×2) and the organic layers combined and dried over MgSO₄. The solvent was concentrated to afford 0.1 g (2.9%) of 2-bromo-5-(trifluoromethoxy) pyridine.

Step 3

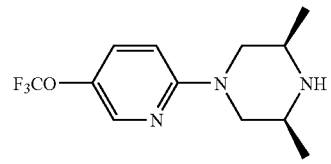

cis-3,5-Dimethyl-1-(5-trifluoromethoxy-pyridin-2-yl)-piperazine: The compound cis-3,5-Dimethyl-1-(5-trifluoromethoxy-pyridin-2-yl)-piperazine was synthesized according to the procedure described in Example 26 using 2-bromo-5-(trifluoromethoxy)pyridine and cis-2,6-dimethylpypiperazine.

Step 4

4-[cis-2,6-Dimethyl-4-(5-trifluoromethyl-pyridin-2-yl)-piperazine-1-sulfonyl]-indan-2-carboxylic acid: The compound 4-[cis-2,6-dimethyl-4-(5-trifluoromethyl-pyridin-2-yl)-piperazine-1-sulfonyl]-indan-2-carboxylic acid was synthesized according to the procedure in Example 79. ¹H NMR (400 MHz, CD₃OD) δ 7.98 (s, 1H), 7.71 (d, 1H), 7.47-7.42 (m, 2H), 7.33 (t, 1H), 6.77 (d, 1H), 4.24-4.18 (m, 1H), 4.12-4.00 (m, 3H), 3.56-3.52 (m, 2H), 3.41-3.25 (m, 3H), 3.03 (dd, 1H), 2.95 (dd, 1H), 1.39 (d, 6H); LCMS 500.5 (M+1)⁺.

EXAMPLE 100

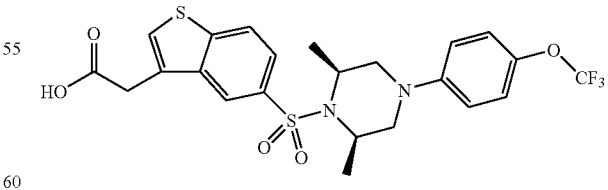

{5-[cis-2,6-Dimethyl-4-(4-trifluoromethoxy-phenyl)-piperazine-3-sulfonyl]-benzo[b]thiophen-3-yl}-acetic acid: The compound {5-[cis-2,6-dimethyl-4-(4-trifluoromethoxy-phenyl)-piperazine-1-sulfonyl]-benzo[b]thiophen-3-yl}-acetic acid was synthesized according to the procedure in Example 47, using cis-2,6-dimethylpiperazine and 1-bromo-4-trifluoromethoxy benzene. ¹H NMR (400 MHz, CD₃OD) δ 8.46 (s, 1H), 7.94 (d, 1H), 7.84 (d, 1H), 7.73 (s, 1H), 7.04 (d, 2H); 6.81 (d, 2H), 4.24-4.20 (m, 2H), 3.91 (s, 2H), 3.27-3.25 (m, 2H), 2.56 (dd, 2H), 1.47 (d, 6H); LCMS 528.9 (M+1)⁺.

7.38 (t, 1H), 7.10 (d, 2H), 6.96 (d, 2H), 3.59-3.54 (m, 2H), 3.42-3.27 (m, 3H), 3.25-3.18 (m, 8H); LCMS 470.9 (M+1)⁺.

EXAMPLE 103

EXAMPLE 101

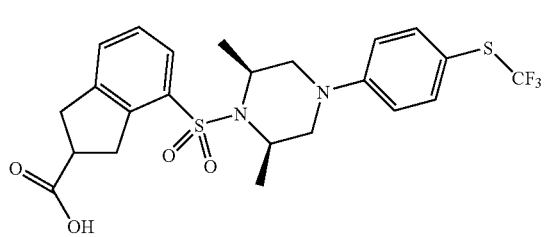

4-[cis-2,6-Dimethyl-4-(4-trifluoromethylsulfanyl-phenyl)-piperazine-1-sulfonyl]-indan-2-carboxylic acid: The compound 4-[cis-2,6-dimethyl-4-(4-trifluoromethylsulfanyl-phenyl)-piperazine-1-sulfonyl]-indan-2-carboxylic acid was synthesized according to the procedure in Example 26, using cis-2,6-dimethylpiperazine and 1-bromo-4-(trifluoromethylsulfanyl)-benzene. ¹H NMR (400 MHz, CD₃OD) δ 7.71 (d, 1H), 7.50-7.44 (m, 3H), 7.33 (t, 1H), 6.91 (d, 2H), 4.22-4.19 (m, 1H), 4.06-4.02 (m, 1H), 3.62-3.50 (m, 4H), 3.41-3.22 (m, 3H), 2.91 (dd, 1H), 2.82 (dd, 1H), 1.45 (d, 6H); LCMS 514.9 (M+1)⁺.

6-[4-(2,4-Dichloro-phenyl)-cis-2,6-dimethyl-piperazine-1-sulfonyl]-indan-1-carboxylic acid: The compound 6-[4-(2,4-dichloro-phenyl)-cis-2,6-dimethyl-piperazine-1-sulfonyl]-indan-1-carboxylic acid was prepared followed the procedure for Example 26. ¹H NMR (400 MHz, CDCl₃), δ 7.90 (s, 1H), 7.72 (d, 1H), 7.36 (d, 1H), 7.35 (s, 1H), 7.10 (d, 1H), 6.80 (d, 1H), 4.25 (m, 1H), 4.11 (m, 2H), 3.17 (m, 1H), 2.99 (m, 3H), 2.64 (dd, 1H), 2.47 (m, 3H), 1.55 (d, 6H).

EXAMPLE 104

EXAMPLE 102

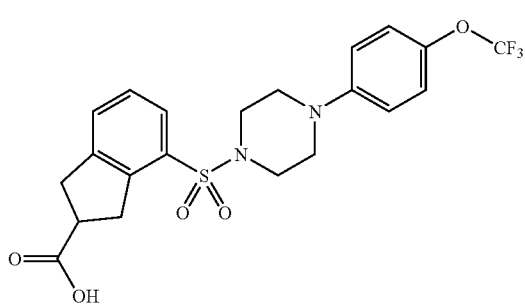

4-[4-(-Trifluoromethoxy-phenyl)-piperazine-1-sulfonyl]-indan-2-carboxylic acid: The compound 4-[4-(-trifluoromethoxy-phenyl)-piperazine-1-sulfonyl]-indan-2-carboxylic acid was synthesized according to the procedure in Example 26 using 1-bromo-4-(trifluoromethoxy)-benzene. ¹H NMR (400 MHz, CD₃OD) δ 7.61 (d, 1H), 7.52 (d, 1H), 6-[cis-2,6-Dimethyl-4-(4-trifluoromethyl-phenyl)-piperazine-1-sulfonyl]-indan-1-carboxylic acid: The compound 6-[cis-2,6-dimethyl-4-(4-trifluoromethyl-phenyl)-piperazine-1-sulfonyl]-indan-1-carboxylic acid was prepared followed the procedure for Example 26. ¹H NMR (400 MHz, CDCl₃), δ 7.89 (s, 1H), 7.77 (d, 1H), 7.42 (d, 2H), 7.32 (d, 1H), 6.78 (d, 2H), 4.26 (m, 1H), 4.11 (m, 2H), 3.36 (m, 2H), 3.09 (m, 1H), 2.94 (m, 1H), 2.83 (m, 1H), 2.77 (m, 1H), 2.44 (m, 2H), 1.44 (d, 6H).

EXAMPLE 105

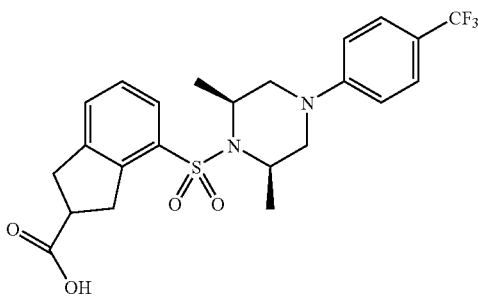

4-[cis-2,6-Dimethyl-4-(4-trifluoromethyl-phenyl)-piperazine-1-sulfonyl]-indan-2-carboxylic acid: The compound 4-[cis-2,6-Dimethyl-4-(4-trifluoromethyl-phenyl)-piperazine-1-sulfonyl]-indan-2-carboxylic acid was prepared followed the procedure for Example 79. $^1$H NMR (400 MHz, CDCl$_3$) δ 7.73 (s, 1H), 7.45 (d, 2H), 7.40 (d, 1H), 7.30 (d, 1H), 6.84 (d, 2H), 4.23 (m, 1H), 4.06 (m, 1H), 3.58 (m, 2H), 3.39 (m, 3H), 3.28 (m, 2H), 2.92 (dd, 1H), 2.83 (dd, 1H), 1.48 (dd, 6H).

EXAMPLE 106

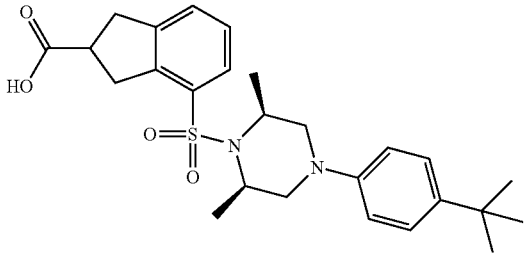

4-[4-(4-tert-Butyl-phenyl)-cis-2,6-dimethyl-piperazine-1-sulfonyl]-indan-2-carboxylic acid Step 1

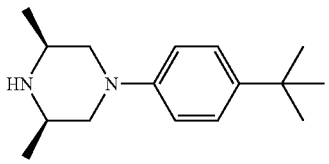

1-(4-tert-Butyl-phenyl)-cis-3,5-dimethyl-piperazine: To a solution of cis-2,6-dimethylpiperazine (1 g, 8.7 mmol) in toluene (35 mL) was added 4-(tert-butyl)bromobenzene (1.86 g, 8.7 mmol), followed by BINAP (0.81 g, 1.3 mmol) and t-BuONa (1.5 g, 15.6 mmol) in one portion each. The resulting mixture was degassed twice. To the mixture was added Pd$_2$(dba)$_3$ (0.79 g, 0.87 mmol) in one portion and the mixture was heated to 100° C. overnight. The reaction mixture was cooled to room temperature and extracted with ethyl acetate (3×100 mL), washed with water (1×100 mL), and brine (1×50 mL), dried over Na$_2$SO$_4$ and concentarted in vacuo. The residue was purified by silica gel column chromatography (0-20% MeOH in dichloromethane) to afford 0.8 g 1-(4-tert-Butyl-phenyl)-cis-3,5-dimethyl-piperazine. $^1$H NMR (400 MHz, CDCl$_3$) δ 7.29-7.26 (m, 2H), 6.88-6.86 (m, 2H), 3.49-3.46 (m, 2H), 3.08-3.00 (m, 2H), 2.33-2.27 (m, 2H), 2.15 (1H, br), 1.29 (s, 9H), 1.13 (d, 6H).

Step 2

4-[4-(4-tert-Butyl-phenyl)-cis-2,6-dimethyl-piperazine-1-sulfonyl]-indan-2-carboxylic acid: The compound 4-[4-(4-tert-butyl-phenyl)-cis-2,6-dimethyl-piperazine-1-sulfonyl]-indan-2-carboxylic acid was synthesized according to the procedure outlined in Example 79 using indane-2-carboxylic acid methyl ester and 1-(4-tert-Butyl-phenyl)-cis-3,5-dimethyl-piperazine obtained from Step 1 above. $^1$H NMR (400 MHz, CD$_3$OD) δ 7.71 (d, 1H), 7.47 (d, 1H), 7.34 (t, 1H), 7.24 (d, 2H), 6.81 (d, 2H), 4.16-4.14 (m, 1H), 4.02-4.00 (m, 1H), 3.54 (d, 2H), 3.34-3.26 (m, 5H), 2.67 (dd, 1H), 2.59 (dd, 1H), 1.51 (d, 3H), 1.50 (d, 3H), 1.26 (s, 9H).

EXAMPLE 107

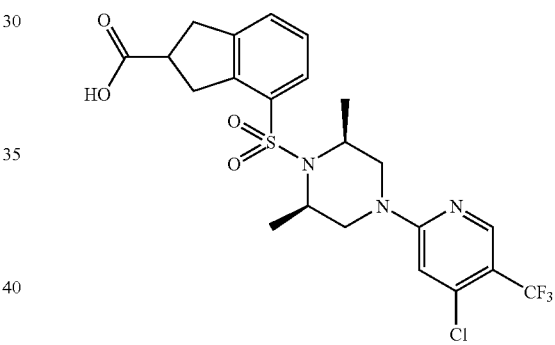

4-[4-(4-Chloro-5-trifluoromethyl-pyridin-2-yl)-cis-2,6-dimethyl-piperazine-1-sulfonyl]-indan-2-carboxylic acid Step 1

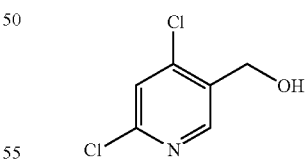

(4,6-Dichloro-pyridin-3-yl)-methanol: To lithium aluminum hydride (2.4 g, 64 mmol) and aluminum chloride (17 g, 128 mmol) in Et$_2$O (200 mL) at 0° C. was added a solution of methyl 4,6-dichloronicotinate (13.1 g, 64 mmol) in Et$_2$O (100 mL) dropwise with stirring. The resulting solution was heated at reflux for one hour. The reaction mixture was quenched with 100 mL of H$_2$O/ice. The resulting solution was extracted with EtOAc (2×500 mL). The organic layers were combined, dried over Na$_2$SO$_4$ and concentrated in vacuo to afford 4.5 g (43%) of (4,6-dichloropyridin-3-yl)methanol.

Step 2

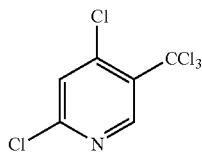

2,4-Dichloro-5-trichloromethyl-pyridine: To a solution of (4,6-dichloropyridin-3-yl)methanol (7 g, 39 mmol) in CCl$_4$ (200 mL), was added sulfuryl dichloride (120 mL) dropwise with stirring. The resulting solution was heated at reflux overnight. The mixture was concentrated and the pH was adjusted to pH 8 by the addition of NaHCO$_3$ (2N). The resulting solution was extracted with EtOAc (2×100 mL) and the organic layers were combined and dried over Na$_2$SO$_4$. The residue was purified by silica gel column chromatography to afford 1.2 g (12%) of 2,4-dichloro-5-(trichloromethyl)pyridine.

Step 3

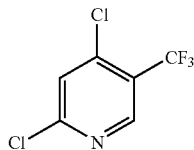

2,4-Dichloro-5-trifluoromethyl-pyridine: A 100 mL sealed tube purged with nitrogen containing 2,4-dichloro-5-(trichloromethyl)-pyridine (0.9 g, 3.00 mmol) and SbF$_5$ (7 g, 30.00 mmol) was heated at 150° C. for 1 h. The reaction mixture was cooled and quenched by the adding 50 g of H2O/ice after cooling. The pH was adjusted to pH=8 by the addition of NaHCO$_3$. The resulting solution was extracted with EtOAc (2×100 mL). The combined organic layers were dried with MgSO$_4$ and concentrated in vacuo to give 0.5 g (62%) of 2,4-dichloro-5-(trifluoromethyl)-pyridine.

Step 4

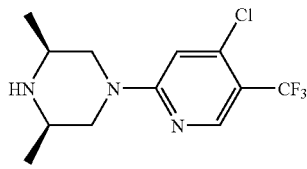

1-(4-Chloro-5-trifluoromethyl-pyridin-2-yl)-cis-3,5-dimethyl-piperazine: 2,4-dichloro-5-(trifluoromethyl)pyridine (800 mg, 3.70 mmol), 2,6-dimethylpiperazine (800 mg, 7.14 mmol), and K$_2$CO$_3$ (1.0 g, 7.25 mmol) were added to dimethylformamide (15 mL). The resulting solution was heated for 2 h at 140° C. The reaction mixture was then quenched by the adding 50 mL of ice-water and extracted with EtOAc (50 mL). The organic layers were combined and dried over MgSO$_4$. The solvent was concentrated and the residue was purified using silica gel column chromatography to 0.2 g (18%) of 1-(4-chloro-5-(trifluoromethyl)pyridine-2-yl)-cis-3,5-dimethylpiperazine.

Step 5

4-[4-(4-Chloro-5-trifluoromethyl-pyridin-2-yl)-cis-2,6-dimethyl-piperazine-1-sulfonyl]-indan-2-carboxylic acid: The compound 4-[4-(4-Chloro-5-trifluoromethyl-pyridin-2-yl)-cis-2,6-dimethyl-piperazine-1-sulfonyl]-indan-2-carboxylic acid was prepared according to the procedure outlined in Example 79 using indane-2-carboxylic acid methyl ester. $^1$H NMR (CD$_3$OD) δ 8.26 (s, 1H), 7.67 (d, 1H), 7.42 (d, 1H), 7.29 (t, 1H), 6.86 (s, 1H) 4.22 (m, 1H), 4.08 (d, 2H), 3.52 (d, 2H), 3.34 (m, 2H), 3.24 (m, 2H), 3.17 (dd, 2H), 1.36 (d, 6H).

EXAMPLE 108

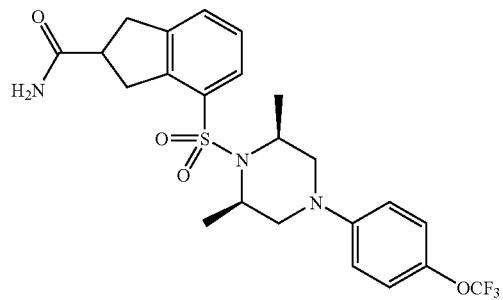

4-[cis-2,6-Dimethyl-4-(4-trifluoromethoxy-phenyl)-piperazine-1-sulfonyl]-indan-2-carboxylic acid amide. Thionyl chloride (42 μL, 0.577 mmol) was added to 4-[cis-2,6-dimethyl-4-(4-trifluoromethoxy-phenyl)-piperazine-1-sulfonyl]-indan-2-carboxylic acid (250 mg, 0.502 mmol) in THF (4 mL) at 50 C for 1 h and then concentrated. The crude mixture was then dissolved in THF (4 mL) and ammonium hydroxide (300 μL) was added. The cloudy brown solution was stirred for an additional 3 h at room temperature. The solution was then concentrated and purified by silica gel column chromatography (0-20% MeOH in dichloromethane) to afford 4-[cis-2,6-dimethyl-4-(4-trifluoromethoxy-phenyl)-piperazine-1-sulfonyl]-indan-2-carboxylic acid amide (190 mg, 76%). $^1$H NMR (400 MHz, CD$_3$OD) δ ppm. 7.71 (d, 1H), 7.47 (d, 1H), 7.34 (t, 1H), 7.10 (d, 2H), 6.94-6.91 (m, 2H), 4.20-4.14 (m, 1H), 4.05-3.90 (m, 1H), 3.54 (d, 2H), 3.41-3.21 (m, 5H), 2.77 (dd, 1H), 2.68 (dd, 1H), 1.51 (d, 3H), 1.49 (d, 3H). LCMS: 498.7 (M+1)$^+$.

EXAMPLE 109

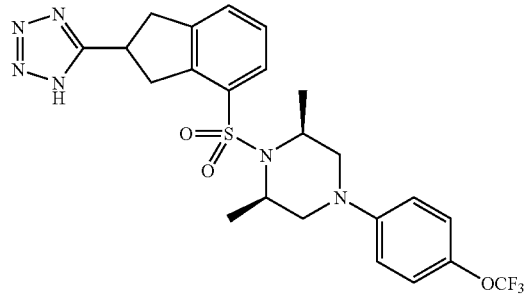

cis-2,6-Dimethyl-1-[2-(1H-tetrazol-5-yl)-indane-4-sulfonyl]-4-(4-trifluoromethoxy-phenyl)-piperazine Step 1

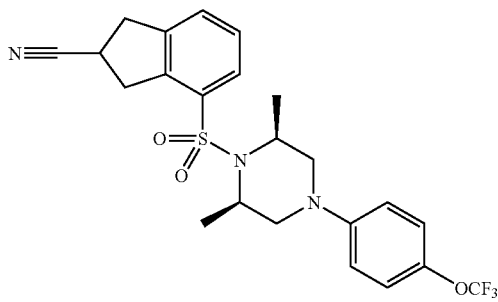

4-[cis-2,6-Dimethyl-4-(4-trifluoromethoxy-phenyl)-piperazine-1-sulfonyl]-indan-2-carbonitrile. Triethylamine (200 μL, 1.4349 mmol) and phosphorus oxychloride (74 μL, 0.7939 mmol) were added to a solution of 4-[cis-2,6-dimethyl-4-(4-trifluoromethoxy-phenyl)-piperazine-1-sulfonyl]-indan-2-carboxylic acid amide (254 mg, 0.5105 mmol) in dichloroethane (3 mL). The reaction was stirred for 4 h at room temperature then directly purified by silica gel column chromatography (0-50% EtOAc in hexanes) to afford 4-[cis-2,6-dimethyl-4-(4-trifluoromethoxy-phenyl)-piperazine-1-sulfonyl]-indan-2-carbonitrile (23 mg, 9%). $^1$H NMR (400 MHz, CD$_3$OD) δ ppm 7.77 (d, 1H), 7.54 (d, 1H), 7.42 (t, 1H), 7.10 (d, 2H), 6.93 (d, 2H), 4.20-4.00 (m, 2H), 3.65-3.60 (m, 1H), 3.60-3.40 (m, 2H), 3.40-3.20 (m, 4H), 2.80-2.60 (m, 2H), 1.50 (d, 6H). LCMS: 480.0 (M+1)$^+$.

Step 2

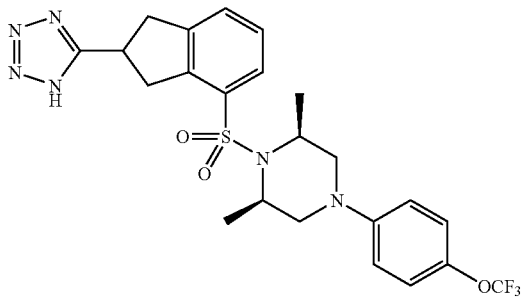

cis-2,6-Dimethyl-1-[2-(1H-tetrazol-5-yl)-indane-4-sulfonyl]4-(4-trifluoromethoxy-phenyl)-piperazine: To a solution of 4-[cis-2,6-dimethyl-4-(4-trifluoromethoxy-phenyl)-piperazine-1-sulfonyl]-indan-2-carbonitrile (23 mg, 0.0440 mmol) in toluene (1 ml) was added dibutyltin oxide (13 mg, 0.0281 mmol) and azidotrimethylsilane (5 μL, 0.0377 mmol). The reaction mixture was stirred at 105° C. for 20 h upon which an additional amount of dibutyltin oxide (13 mg, 0.0281 mmol) and azidotrimethylsilane (25 μL, 0.1884 mmol) was added and stirred at 105° C. for 4 h. The reaction mixture was cooled to room temperature and then directly purified by silica gel column chromatography (0-10% MeOH in dichloromethane) to afford cis-2,6-dimethyl-1-[2-(1H-tetrazol-5-yl)-indane-4-sulfonyl]-4-(4-trifluoromethoxy-phenyl)-piperazine (14 mg, 61%). $^1$H NMR (400 MHz, CD$_3$OD) δ ppm 7.75 (d, 1H), 7.54 (d, 1H), 7.39 (t, 1H), 7.09 (d, 2H), 6.90 (d, 2H), 4.18-4.02 (m, 3H), 3.89 (dd, 1H), 3.59-3.51 (m, 2H), 3.36-3.31 (m, 3H), 2.66-2.60 (m, 2H), 1.48 (d, 6H). LCMS: 523.11 (M+1)$^+$.

EXAMPLE 110

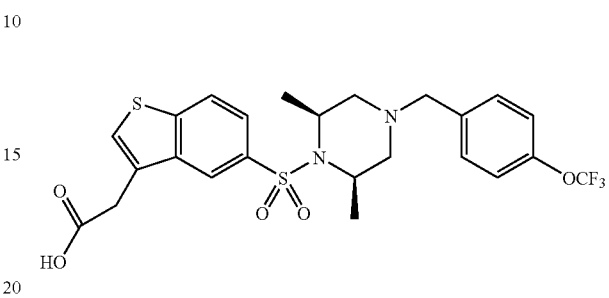

{5-[cis-2,6-dimethyl-4-(4-trifluoromethoxy-benzyl)-piperazine-1-sulfonyl]-benzo[b]thiophen-3-yl}-acetic acid: The compound {5-[cis-2,6-dimethyl-4-(4-trifluoromethoxy-benzyl)-piperazine-1-sulfonyl]-benzo[b]thiophen-3-yl}-acetic acid was synthesized according to the procedure in Example 37 using (5-chlorosulfonyl-benzo[b]thiophen-3-yl)-acetic acid methyl ester and cis-3,5-dimethyl-1-(4-trifluoromethoxy-benzyl)-piperazine from Example 95, Step 1. $^1$H NMR (400 MHz, CD$_3$OD) δ 8.48 (s, 1H), 7.96 (d, 1H), 7.88-7.80 (m, 2H), 7.57 (d, 2H), 7.28 (d, 2H), 4.60-4.50 (m, 2H), 4.36 (s, 2H), 3.97 (s, 2H), 3.38-3.28 (m, 2H), 2.74-2.64 (m, 2H), 1.55 (d, 6H); LCMS 542.9 (M+1)$^+$.

EXAMPLE 111

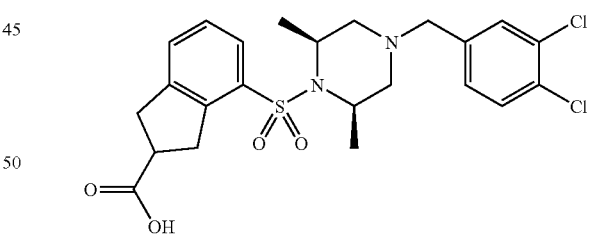

4-[-3(3,4-Dichloro-benzyl)-cis-2,6-dimethyl-piperazine-1-sulfonyl]-indain-2-carboxylic acid: The compound 4-[-3 (3,4-dichloro-benzyl)-cis-2,6-dimethyl-piperazine-1-sulfonyl]-indain-2-carboxylic acid was synthesized according to the procedure in Example 95 using 3,4-dichloro-benzaldehyde. $^1$H NMR (400 MHz, CD$_3$OD) δ 7.67 (d, 1H), 7.57 (s, 1H), 7.56-7.46 (m, 2H), 7.36-7.28 (m, 2H), 4.38-4.22 (m, 1H), 4.18-4.01 (m, 1H), 3.90-3.70 (m, 1H), 3.52-3.20 (m, 6H), 2.98-2.80 (m, 2H), 2.50-2.30 (m, 2H), 1.51 (d, 6H); LCMS 499.8 (M+1)$^+$.

EXAMPLE 112

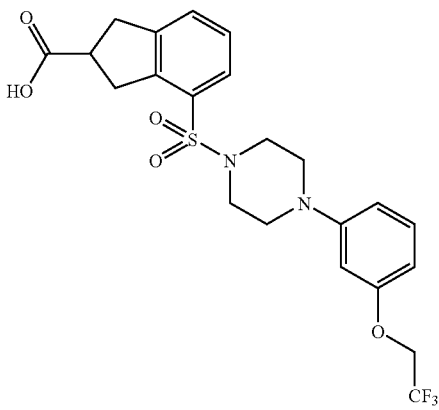

4-[4-(3-Trifluomethoxy-phenyl)-piperazine-1-sulfonyl]-indan-2-carboxylic acid

Step 1

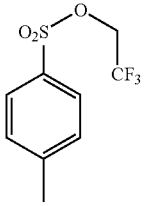

Toluene-4-sulfonic acid trifluoromethyl ester: To a solution of 2,2,2-trifluoroethanol (5 g, 50.00 mmol) in methylene chloride (20 mL) was added 4-methylbenzene-1-sulfonyl chloride (9.4 g, 49.21 mmol). Triethylamine (15 g, 148.51 mmol) was added and the resulting solution was stirred overnight. Water (50 mL) was added and the resulting solution was extracted with methylene chloride (2×20 mL). The combined organic layers were dried ($Na_2SO_4$) and concentrated in vacuo to afford 10 g (78.7%) of 2,2,2-trifluoroethyl 4-methylbenzenesulfonate.

Step 2

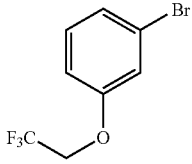

1-Bromo-3-(2,2,2-trifluoroethoxy)benzene: To a solution of 2,2,2-trifluoroethyl 4-methylbenzenesulfonate (3 g, 11.81 mmol) in dimethylformamide (20 mL) was added 3-bromophenol (1 g, 5.78 mmol) and NaOH (500 mg, 12.50 mmol). The resulting solution was stirred at 100° C. for 3 h. The reaction mixture was quenched by the adding $H_2O$ (100 mL) and extracted with methylene chloride (3×50 mL). The combined organic layers were dried ($Na_2SO_4$) and concentrated, and the residue purified by silica gel column chromatography (1:20 EtOAc/petroleum ether) to provide 1.1 g (31%) of 1-bromo-3-(2,2,2-trifluoroethoxy)benzene.

Step 3

4-{4-[3-(2,2,2-trifluoro-ethoxy)-phenyl]-piperazine-1-sulfonyl}-indan-2-carboxylic acid. The compound 4-{4-[3-(2,2,2-trifluoro-ethoxy)-phenyl]-piperazine-1-sulfonyl}-indan-2-carboxylic acid was prepared according to the procedure outlined in Example 26 using indane-2-carboxylic acid methyl ester. $^1$H NMR ($CD_3OD$) δ 7.61 (d, 1H), 7.52 (d, 1H), 7.14 (t, 1H), 6.60 (dd, 1H), 6.54 (t, 1H), 6.47 (dd, 1H), 4.45 (q, 2H), 3.56 (m, 2H), 3.35 (m, 2H), 3.21 (m, 8H).

EXAMPLE 113

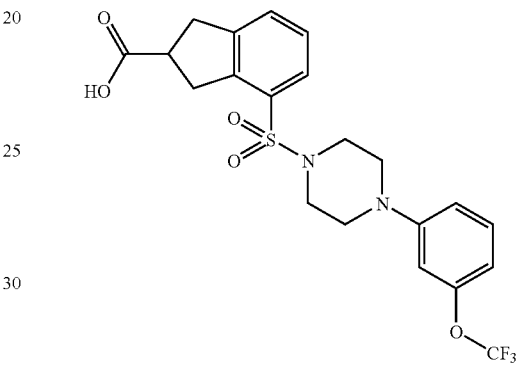

Step 1

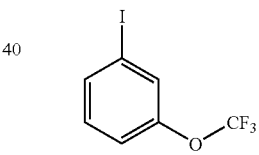

1-Iodo-3-(trifluoromethoxy)benzene: To 3-(trifluoromethoxy)benzenamine (17.7 g, 100.00 mmol) was added a solution of $NaNO_2$ (7.4 g, 115.62 mmol) in $H_2O$ (80 ml). $H_2SO_4$ (25 g, 250.00 mmol) was added dropwise with stirring at −5° C. The resulting solution was kept at −5° C. for 15 minutes. To this solution was added a solution of KI (20 g, 120.48 mmol) in $H_2O$ (60 ml) dropwise. The resulting solution was stirred overnight at room temperature and extracted with EtOAc (2×100 mL). The combined organic layers were washed with $Na_2SO_3/H_2O$ (2×50 mL), dried over $Na_2SO_4$ and concentrated in vacuo. The residue was purified by silica gel column chromatography to afford 4.0 g (14%) of 1-iodo-3-(trifluoromethoxy)benzene.

Step 2

4-[4-(3-Trifluomethoxy-phenyl)-piperazine-1-sulfonyl]-indan-2-carboxylic acid. The compound 4-[4-(3-Trifluomethoxy-phenyl)-piperazine-1-sulfonyl]-indan-2-carboxylic acid was prepared according to the procedure outlined in Example 26 using indane-2-carboxylic acid methyl ester. $^1$H NMR ($CD_3OD$) δ 7.61 (dd, 1H), 7.52 (dd, 1H), 7.39 (t, 1H), 7.26 (t, 1H), 6.90 (dd, 1H), 6.78 (s, 1H), 6.69 (dd, 1H), 3.56 (m, 2H), 3.36 (m, 2H), 3.24 (m, 8H).

EXAMPLE 114

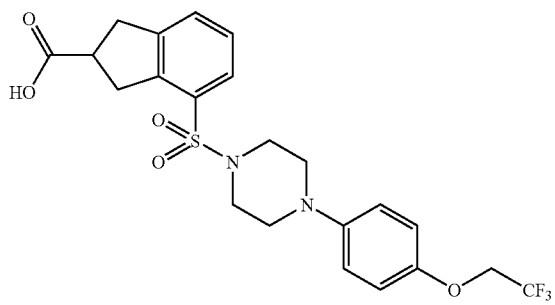

4-{4-[4-(2,2,2-Trifluoro-ethoxy)-phenyl]-piperazine-1-sulfonyl}-indan-2-carboxylic acid: The compound 4-{4-[4-(2,2,2-Trifluoro-ethoxy)-phenyl]-piperazine-1-sulfonyl}-indan-2-carboxylic acid was prepared according to the procedure outlined in Example 112 using indane-2-carboxylic acid methyl ester and 1-[4-(2,2,2-trifluoro-ethoxy)-phenyl]-piperazine. $^1$H NMR (CD$_3$OD) δ 7.61 (dd, 1H), 7.53 (dd, 1H), 7.39 (m, 4H) 4.41 (q, 2H), 3.56 (m, 2H), 3.37 (m, 2H), 3.20 (m, 4H), 3.10 (m, 4H).

EXAMPLE 115

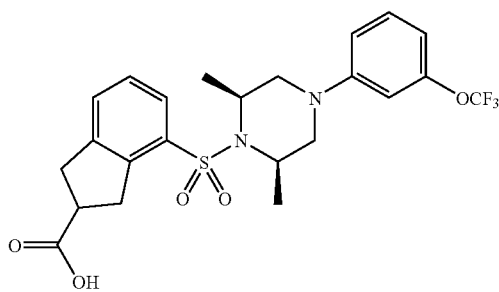

4-[cis-2,6-Dimethyl-4-(3-trifluoromethoxyphenyl)-piperazine-1-sulfonyl]-indan-2-carboxylic acid. The title compound was prepared according to the procedure outlined in Example 113 using indane-2-carboxylic acid methyl ester and cis-3,5-dimethyl-1-(3-trifluoromethoxy-phenyl)-piperazine. $^1$H NMR (CD$_3$OD) δ 7.71 (d, 1H), 7.46 (d, 1H), 7.34 (t, 1H), 7.25 (t, 1H), 6.85 (dd, 1H), 6.87 (s, 1H), 6.67 (d, 1H), 4.18 (m, 1H), 4.03 (m, 1H), 3.53 (d, 1H), 3.41 (m, 2H), 3.35 (m, 2H), 2.81 (dd, 1H), 2.73 (dd, 2H), 1.48 (dd, 6H).

EXAMPLE 116

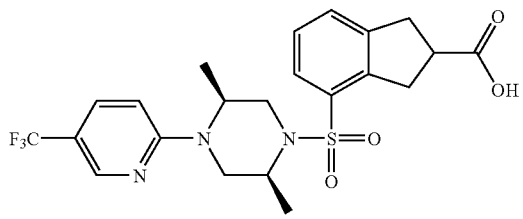

4-[2S,5S-Dimethyl-4-(5-trifluoromethyl-pyridin-2-yl)-piperazine-1-sulfonyl]-indan-2-carboxylic acid Step 1

2S,5S-Dimethyl-1-(5-trifluoromethyl-pyridin-2-yl)-piperazine: 2-chloro-5-trifluoromethyl-pyridine (330 mg, 1.8 mmol), 2S,5S-dimethyl-piperazine dihydrobromide (1.0 g, 3.6 mmol), potassium carbonate (2.0 g, 14 mmol), and DMF (8 mL) were heated at 100° C. under nitrogen for 9.5 h. The mixture was allowed to cool to room temperature, filtered through Celite with dichloromethane, and concentrated in vacuo. The residue was purified by silica gel chromatography (1:0→4:1; dichloromethane:methanol) to give 2S,5S-dimethyl-1-(5-trifluoromethyl-pyridin-2-yl)-piperazine: MS (ESI): 259.8 (M+H).

Step 2

4-[2S,5S-Dimethyl-4-(5-trifluoromethyl-pyridin-2-yl)-piperazine-1-sulfonyl]-indan-2(R,S)-carboxylic acid methyl ester: A solution of 4-chlorosulfonyl-indan-2(R,S)-carboxylic acid methyl ester (250 mg, 0.91 mmol) and THF (2 mL) was added to a solution of 2S,5S-dimethyl-1-(5-trifluoromethyl-pyridin-2-yl)-piperazine (150 mg, 0.58 mmol), triethylamine (0.30 mL, 2.2 mmol) and THF (8 mL) at to room temperature under nitrogen. After 2 h, silica gel was added, and the mixture was concentrated in vacuo. Purification by silica gel chromatography (99:1→9:1; CH$_2$Cl$_2$:methanol) gave 4-[2S,5S-dimethyl-4-(5-trifluoromethyl-pyridin-2-yl)-piperazine-1-sulfonyl]-indan-2(R,S)-carboxylic acid methyl ester: MS (ESI): 498.5 (M+H).

Step 3

4-[2S,5S-Dimethyl-4-(5-trifluoromethyl-pyridin-2-yl)-piperazine-1-sulfonyl]-indan-2(R,S)-carboxylic acid: A mixture of 4-[2S,5S-Dimethyl-4-(5-trifluoromethyl-pyridin-2-yl)-piperazine-1-sulfonyl]-indan-2-carboxylic acid methyl ester (97 mg, 0.19 mmol), 1N LiOH (2 mL), tetrahydrofuran (8 mL), and methanol (2 mL) was stirred at to room temperature for 2 h. The reaction was poured into 1N HCl (40 mL) and extracted with ethyl acetate (40 mL×2). The combined organic extracts were dried, filtered, and concentrated in vacuo to give 4-[2S,5S-dimethyl-4-(5-trifluoromethyl-pyridin-2-yl)-piperazine-1-sulfonyl]-indan-2(R,S)-carboxylic acid: $^1$H NMR (400 MHz, DMSO-d6): δ 8.16 (s, 1H), 8.12 (s, 1H), 7.54-7.43 (m, 4H), 7.12 (d, 1H), 7.11 (d, 1H), 7.01 (app td, 2H), 6.32 (d, 1H), 6.28 (d, 1H), 4.38-4.24 (m, 2H), 4.02-3.66 (m, 6H), 3.50-3.32 (m, 2H), 3.26-3.10 (m, 5H), 3.06-

2.94 (m, 3H), 2.92-2.82 (m, 3H), 2.82-2.72 (m, 1H), 1.22-1.15 (m, 6H), 0.98 (d, 3H), 0.96 (d, 3H); MS (ESI): 484.4 (M+H).

EXAMPLE 117

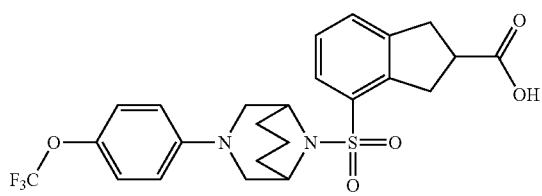

4-[3-(4-Trifluoromethoxy-phenyl)-3,9-diaza-bicyclo[3.3.1]nonane-9-sulfonyl]-indan-2-carboxylic acid Step 1 cis-1-benzyl-piperidine-2,6-dicarboxylic acid hydrochloride: A mixture of cis-1-benzyl-piperidine-2,6-dicarboxylic acid dimethyl ester (2.33 g, 8 mmol) and 6N HCl (28 mL) was heated at 115° C. for 14 h. The resulting solution was cooled to 0° C. and stirred for 2 h. The white precipitate was filtered and dried to give cis-1-benzyl-piperidine-2,6-dicarboxylic acid hydrochloride: MS (ESI): 264.5 (M+H).

Step 2

9-benzyl-3-(4-trifluoromethoxy-phenyl)-3,9-diaza-bicyclo[3.3.1]nonane-2,4-dione: 1,1-Carbonyl diimidazole (CDI; 1.2 g, 7.4 mmol) was added to a mixture of cis-1-benzyl-piperidine-2,6-dicarboxylic acid hydrochloride (1.0 g, 3.34 mmol) and dioxane (10 mL) at rt under $N_2$. The mixture was heated at 100° C. After 15 min, a solution of 4-trifluoromethoxyaniline (600 mg, 3.39 mmol) and dioxane (2 mL) was added. After an additional 2 h, CDI (500 mg, 3.08 mmol) was added (Caution: $CO_2$ evolution). After an additional 1 h, the reaction was allowed to cool to rt, concentrated, diluted with ethyl acetate (120 mL) and washed with 0.5N HCl (100 mL×2). The organic extract was dried, filtered, concentrated, and purified by silica gel chromatography (1:0→4:1; hexanes:ethyl acetate) to give 9-benzyl-3-(4-trifluoromethoxy-phenyl)-3,9-diaza-bicyclo[3.3.1]nonane-2,4-dione: MS (ESI): 405.4 (M+H).

Step 3

3-(4-trifluoromethoxy-phenyl)-3,9-diaza-bicyclo[3.3.1]nonane-2,4-dione: A mixture of 9-benzyl-3-(4-trifluoromethoxy-phenyl)-3,9-diaza-bicyclo[3.3.1]nonane-2,4-dione (120 mg, 0.3 mmol), 10% Pd/C (20 mg, 0.02 mmol Pd), ethyl acetate (8 mL), and ethanol (2 mL) were stirred vigorously under an atmosphere of $H_2$. After 2 h, more ethanol (2 mL) was added. After an additional 16 h, the reaction was filtered through Celite and concentrated to give 3-(4-trifluoromethoxy-phenyl)-3,9-diaza-bicyclo[3.3.1]nonane-2,4-dione: MS (ESI): 315.4 (M+H).

Step 4

3-(4-trifluoromethoxy-phenyl)-3,9-diaza-bicyclo[3.3.1]nonane: A solution of 3-(4-trifluoromethoxy-phenyl)-3,9-diaza-bicyclo[3.3.1]nonane-2,4-dione (80 mg, 0.25 mmol) and THF (4 mL) was heated at 70° C. under $N_2$. A solution of $BH_3 \cdot SMe_2$ (2M in THF, 0.4 mL, 0.8 mmol) was added dropwise. After 40 min, 6N HCl (1.0 mL) was added drop-vise (Caution: $H_2$ evolution). After an additional 30 min, the reaction was poured into 1N NaOH (8 mL) and extracted with dichloromethane (30 mL×2). The combined organic extracts were dried, filtered and concentrated to give 3-(4-trifluoromethoxy-phenyl)-3,9-diaza-bicyclo[3.3.1]nonane: MS (ESI): 287.5 (M+H).

Step 5

4-[3-(4-trifluoromethoxy-phenyl)-3,9-diaza-bicyclo[3.3.1]nonane-9-sulfonyl]-indan-2-carboxylic acid methyl ester: A mixture of 3-(4-trifluoromethoxy-phenyl)-3,9-diaza-bicyclo[3.3.1]nonane (60 mg, 0.21 mmol), 4-chlorosulfonyl-indan-2(R,S)-carboxylic acid methyl ester (120 mg, 0.44 mmol), potassium carbonate (200 mg, 1.4 mmol), and acetonitrile (3 mL) were heated at 50° C. for 2 h. The mixture was filtered through Celite, concentrated, and purified by silica gel chromatography (9:1→4:1; hexanes:ethyl acetate) to give 4-[3-(4-trifluoromethoxy-phenyl)-3,9-diaza-bicyclo[3.3.1]nonane-9-sulfonyl]-indan-2-carboxylic acid methyl ester: MS (ESI): 525.5 (M+H).

Step 6

4-[3-(4-trifluoromethoxy-phenyl)-3,9-diaza-bicyclo[3.3.1]nonane-9-sulfonyl]-indan-2-carboxylic acid: A mixture of 4-[3-(4-trifluoromethoxy-phenyl)-3,9-diaza-bicyclo[3.3.1]nonane-9-sulfonyl]-indan-2-carboxylic acid methyl ester (13 mg, 0.025 mmol), 1N LiOH (2 mL), tetrahydrofuran (8 mL), and methanol (2 mL) was stirred at rt for 3 h. The reaction was poured into 1N HCl (40 mL) and extracted with ethyl acetate (40 mL×2). The combined organic extracts were dried, filtered, and concentrated to give 4-[3-(4-trifluoromethoxy-phenyl)-3,9-diaza-bicyclo[3.3.1]nonane-9-sulfonyl]-indan-2-carboxylic acid: $^1$H NMR (400 MHz, DMSO-d6): δ 7.69 (d, 1H), 7.52 (d, 1H), 7.38 (t, 1H), 7.19 (d, 2H), 6.92 (d, 2H), 4.04-3.97 (m, 2H), 3.74-3.67 (m, 2H), 3.44-3.30 (m, 3H), 3.26-3.10 (m, 2H), 2.96-2.86 (m, 2H), 2.26-2.15 (m, 1H), 1.86-1.72 (m, 4H), 1.51-1.43 (m, 1H); MS (ESI): 511.4 (M+H).

Additional compounds, like those disclosed below, can be made using the methods described above. It is expected that these compounds when made will have activity similar to those that have been made in the examples above. Such compounds have the structure A-B-C-D, wherein:

A is selected from the group consisting of

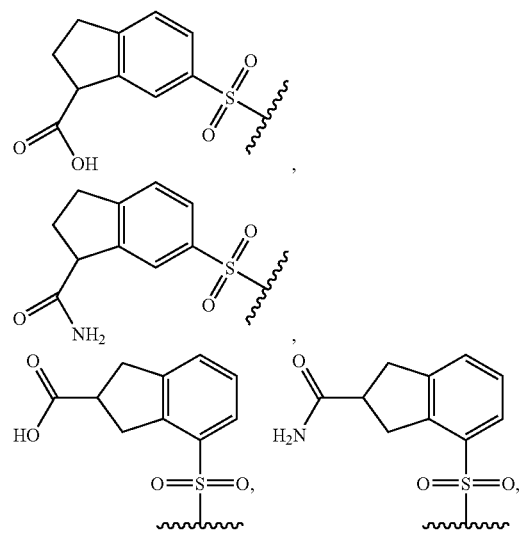

-continued
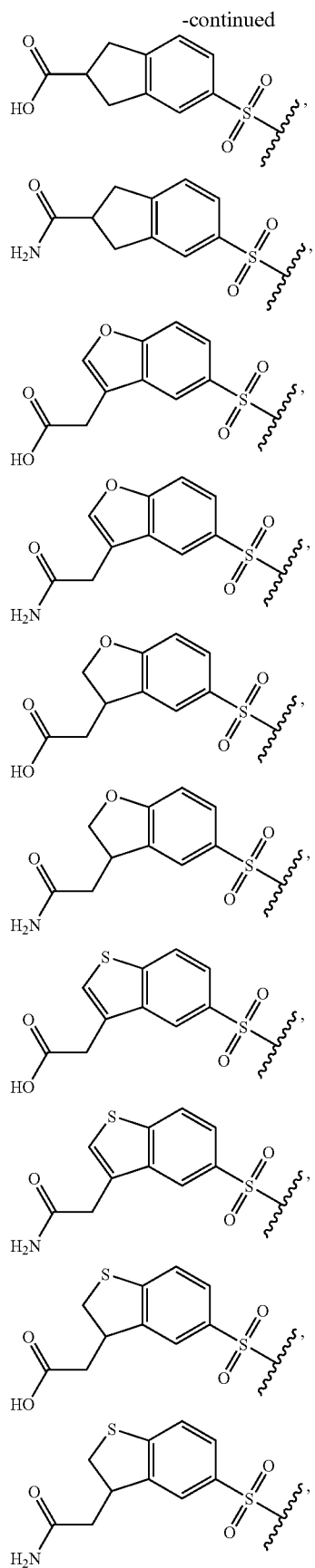
-continued
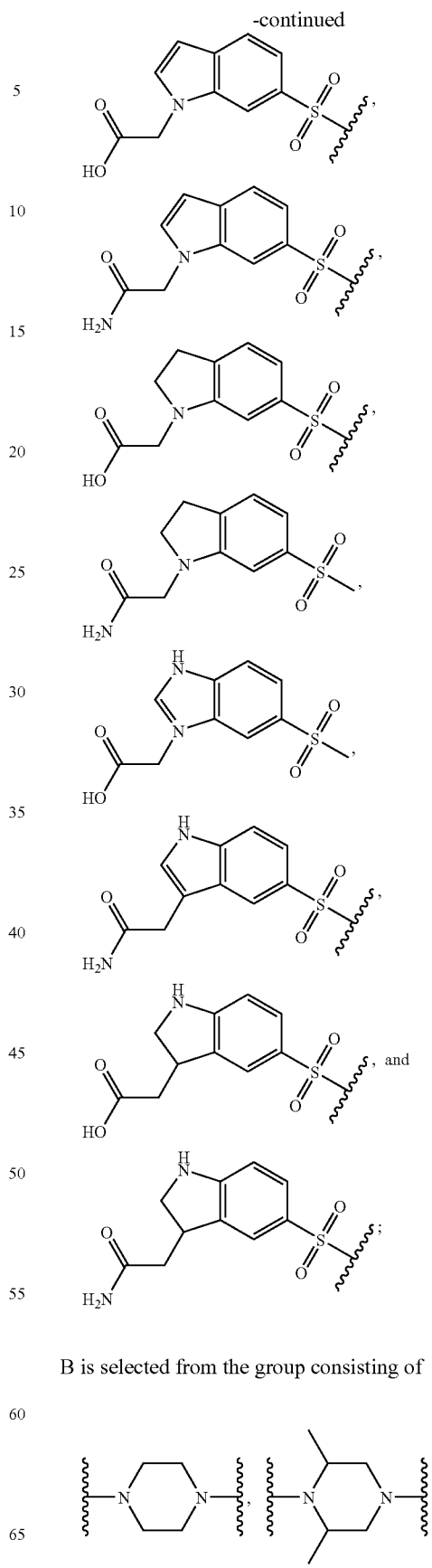
B is selected from the group consisting of -continued
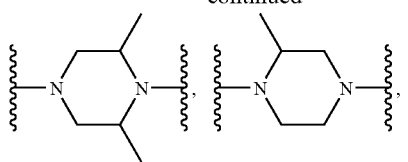
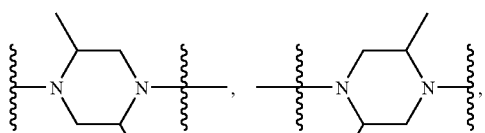
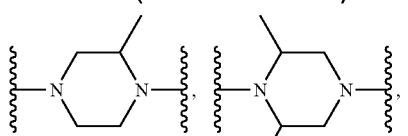
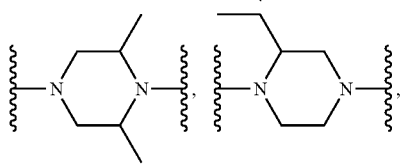
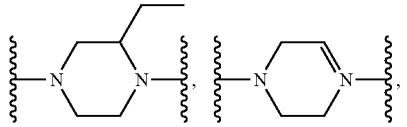
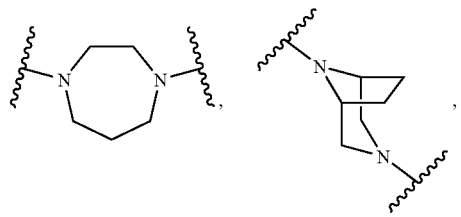
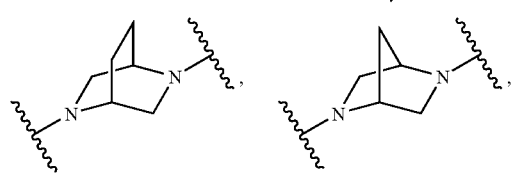
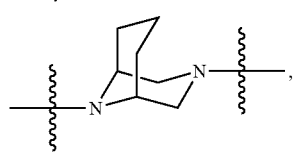
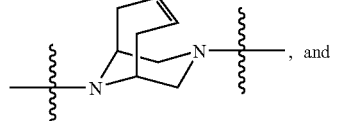
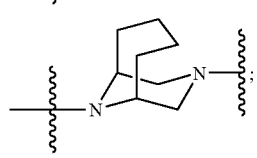
C is selected from the group consisting of
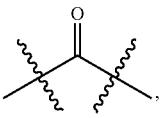
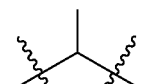
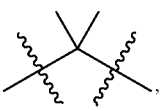
, and
; and
D is selected from the group consisting of
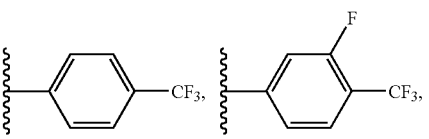
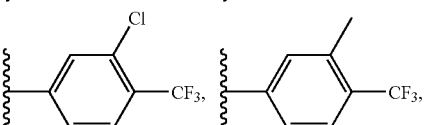
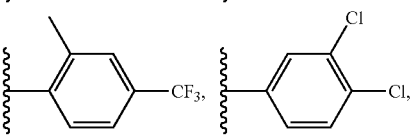
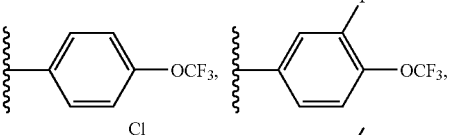
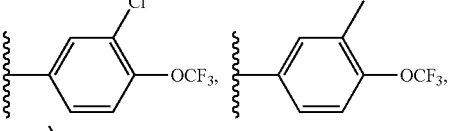
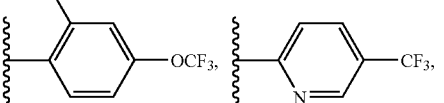

-continued
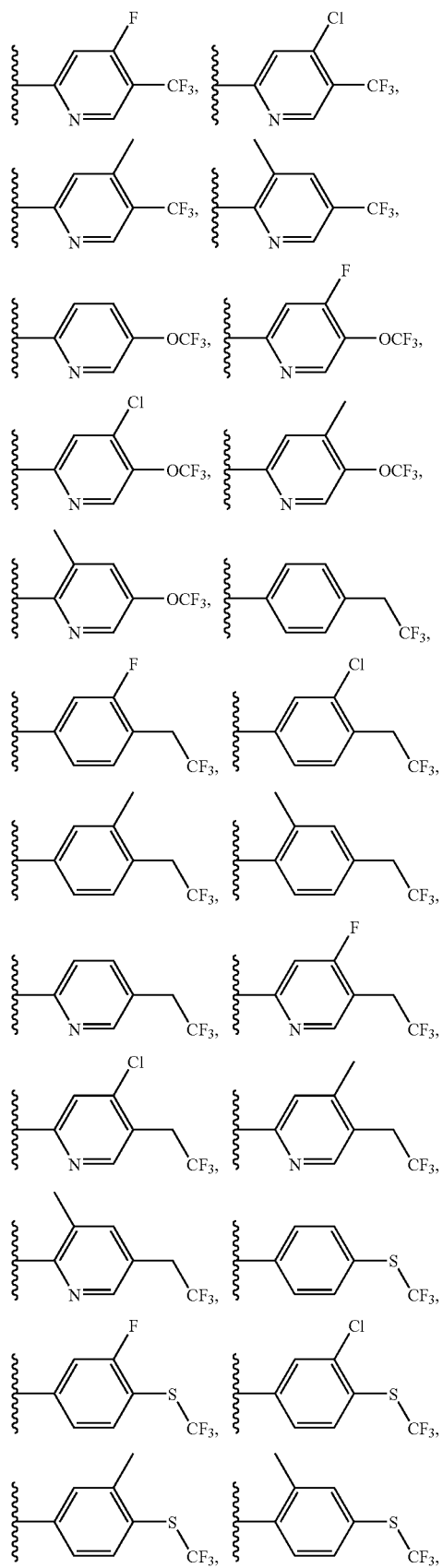
-continued
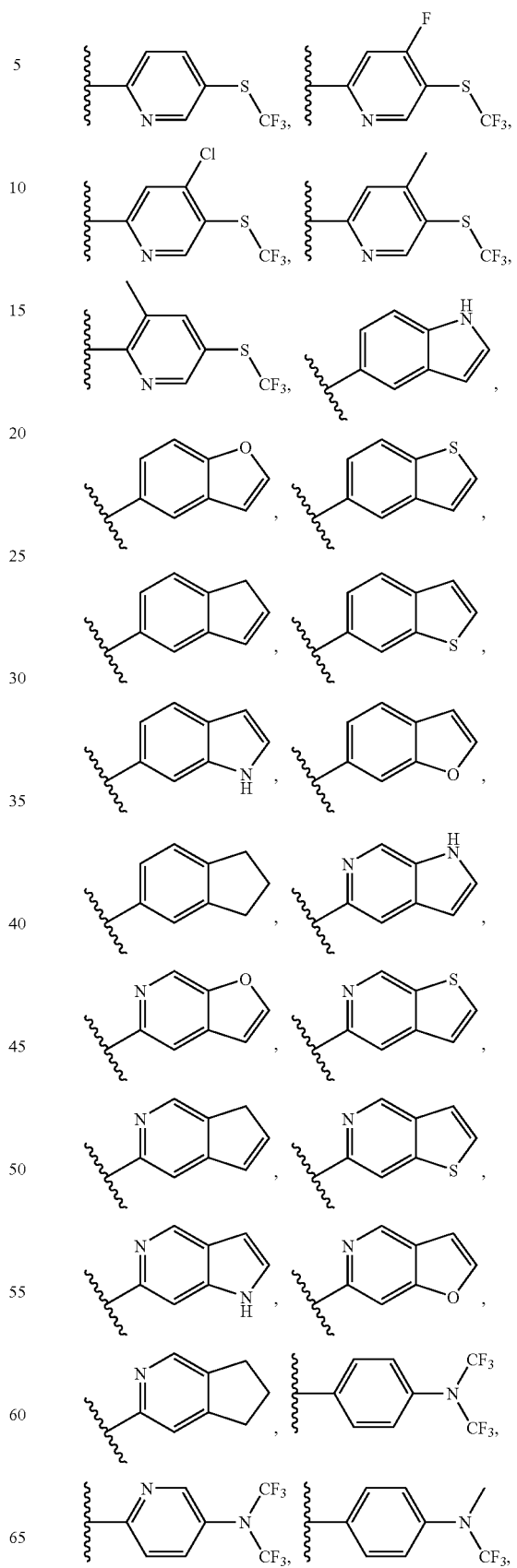

-continued
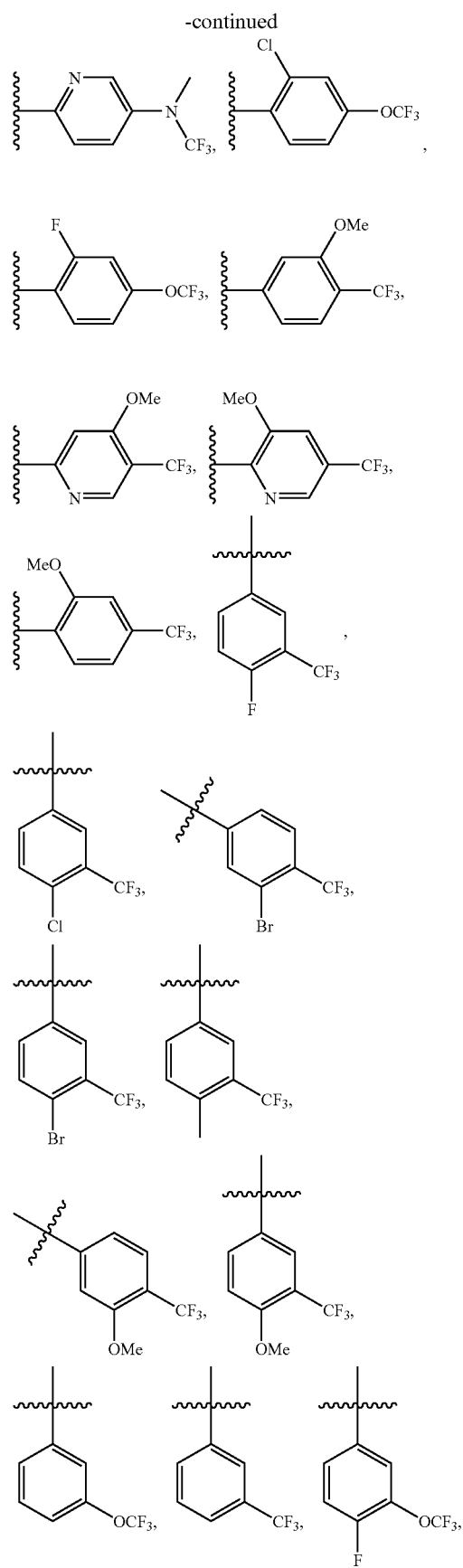
-continued
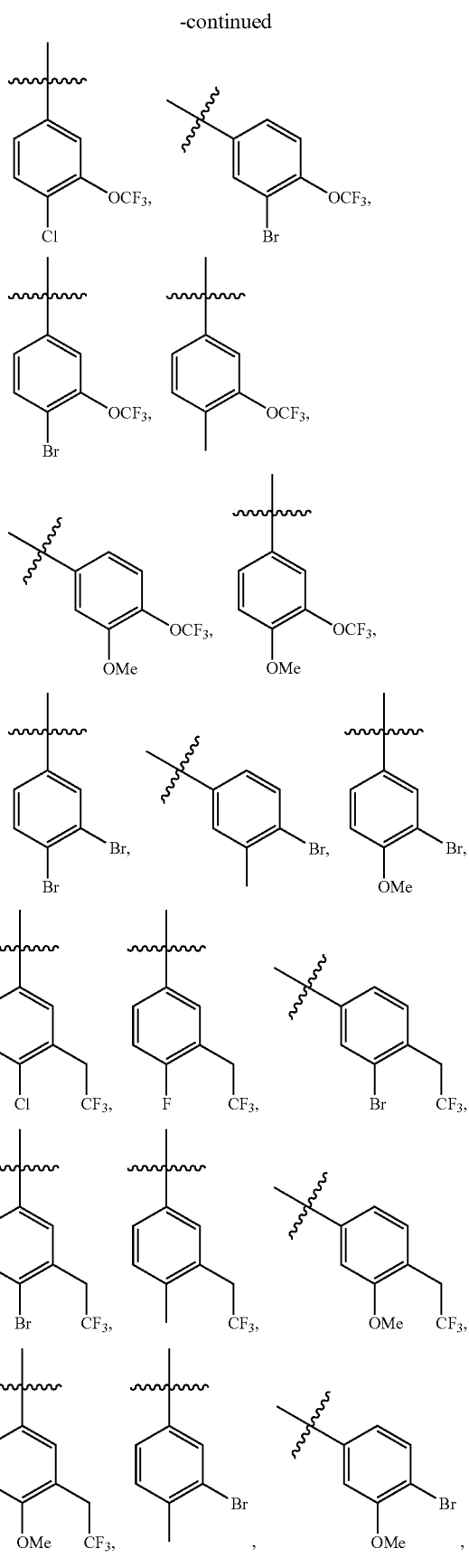

-continued

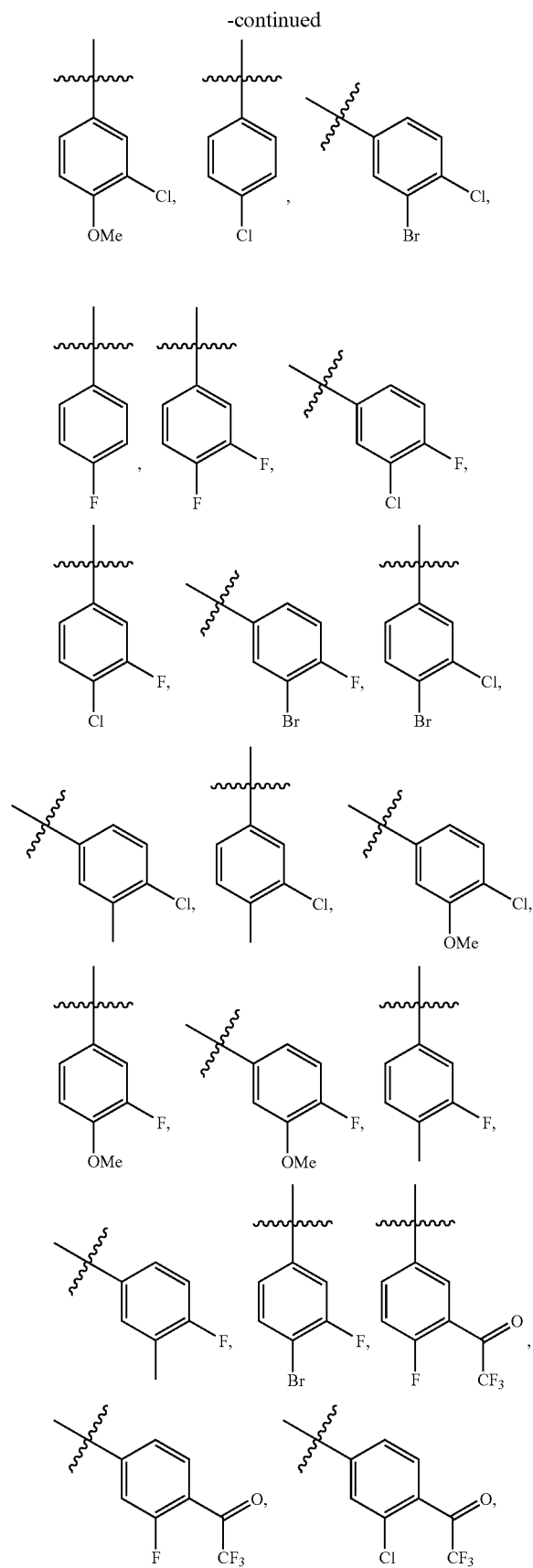

-continued

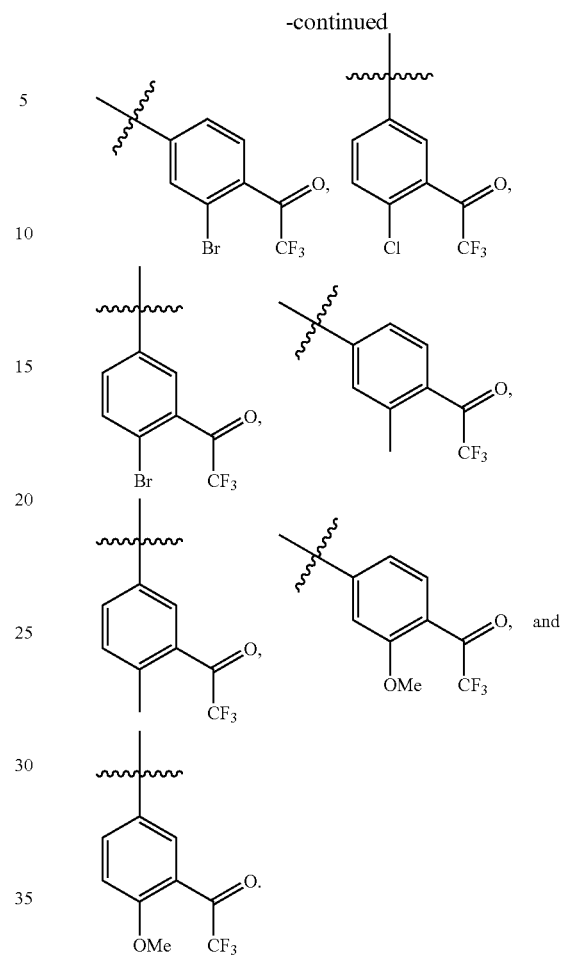

The compounds in Examples 1-117 have been shown to be PPAR modulators using the following assays. The other compounds listed above, some of which have not yet been made and/or tested, are predicted to have activity in these assays as well.

In Vitro Biological Activity Assay

Compounds may be screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same synthetic response element and to prevent endogenous receptor activation from complicating the interpretation of results. See, for example, Lehmann, J. M.; Moore, L. B.; Smith-Oliver, T. A; Wilkinson, W. O.; Willson, T. M.; Kliewer, S. A., An antidiabetic thiazolidinedione is a high affinity ligand for peroxisome proliferator-activated receptor δ (PPARδ), *J. Biol. Chem.*, 1995, 270, 12953-6. The ligand binding domains for murine and human PPAR-alpha, PPAR-gamma, and PPAR-delta are each fused to the yeast transcription factor GAL4 DNA binding domain. CV-1 cells were transiently transfected with expression vectors for the respective PPAR chimera along with a reporter construct containing four or five copies of the GAL4 DNA binding site driving expression of luciferase. After 8-16 h, the cells are replated into multi-well assay plates and the media is exchanged to phenol-red free DME medium supplemented with 5% delipidated calf serum. 4 hours after replating, cells were treated with either compounds or 1% DMSO for 20-24 hours. Luciferase activity was then assayed with Britelite (Perkin Elmer) following the manufacturer's protocol and measured with either the Perkin Elmer Viewlux or Molecular Devices Acquest (see, for example, Kliewer, S. A., et. al. Cell 1995, 83, 813-819). Rosiglitazone is used as a positive control in the PPARδ assay. Wy-14643 and GW7647 is used as a positive control in the PPARδ assay. GW501516 is used as the positive control in the PPARδ assay.

Compounds of Examples 1-117 were assayed to measure their biological activity with respect to their $EC_{50}$ values for modulating PPAR-alpha, PPAR-gamma, and PPAR-delta as set forth in Table 1.

TABLE 1

| | Biological Activity | | |
|---|---|---|---|
| Example # | PPAR alpha<br>A > 100 μM<br>B = 5-100 μM<br>C = <5 μM | PPAR delta<br>A > 100 μM<br>B = 5-100 μM<br>C = <5 μM | PPAR gamma<br>A > 100 μM<br>B = 5-100 μM<br>C = <5 μM |
| 1 | B | B | B |
| 2 | A | C | B |
| 3 | B | B | B |
| 4 | A | B | A |
| 5 | B | C | B |
| 6 | A | C | C |
| 7 | B | C | B |
| 8 | B | C | C |
| 9 | B | C | B |
| 10 | B | C | C |
| 11 | B | C | C |
| 12 | A | B | A/B |
| 13 | B | C | B |
| 14 | A | B | B |
| 15 | B | B | B |
| 16 | B | C | B |
| 17 | B | B | B |
| 18 | B | C | B |
| 19 | C | C | C |
| 20 | C | C | C |
| 21 | B | B | B |
| 22 | C | C | B |
| 23 | C | C | C |
| 24 | C | C | C |
| 25 | C | C | C |
| 26 | C | C | C |
| 27 | B | C | B |
| 28 | A | C | B |
| 29 | B | B | B |
| 30 | B | B | B |
| 31 | A | B | A |
| 32 | A | C | B |
| 33 | A | C | B |
| 34 | A | C | B |
| 35 | B | C | B |
| 36 | A | A | B |
| 37 | B | C | C |
| 38 | C | C | C |
| 39 | C | C | C |
| 40 | C | C | C |
| 41 | B | C | B |
| 42 | B | C | B |
| 43 | A | C | B |
| 44 | A | C | B |
| 45 | C | C | C |
| 46 | C | C | C |
| 47 | C | C | C |
| 48 | C | C | C |
| 49 | C | C | B |
| 50 | B | C | B |
| 51 | C | C | B |
| 52 | C | C | C |
| 53 | C | C | C |
| 54 | C | C | C |
| 55 | C | C | C |
| 56 | C | C | C |
| 57 | C | C | C |
| 58 | C | C | B |
| 59 | C | C | B |
| 60 | C | C | B |
| 61 | C | C | C |
| 62 | C | C | B |
| 63 | C | C | C |
| 64 | C | C | C |
| 65 | C | C | C |
| 66 | C | C | B |
| 67 | C | C | C |
| 68 | C | C | C |
| 69 | C | C | C |
| 70 | C | C | B |
| 71 | C | C | C |
| 72 | C | C | C |
| 73 | B | C | C |
| 74 | C | C | C |
| 75 | B | C | B |
| 76 | A | C | A |
| 77 | A | C | A |
| 78 | B | C | B |
| 79 | A | C | A |
| 80 | A | C | A |
| 81 | A | C | A |
| 82 | A | C | A |
| 83 | B | C | B |
| 84 | A | B | B |
| 85 | B | C | B |
| 86 | C | C | C |
| 87 | B | C | C |
| 88 | A | C | B |
| 89 | C | C | C |
| 90 | B | C | B |
| 91 | B | C | C |
| 92 | B | C | B |
| 93 | B | C | B |
| 94 | B | C | B |
| 95 | B | C | B |
| 96 | A | C | B |
| 97 | B | C | B |
| 98 | B | C | C |
| 99 | B | C | B |
| 100 | B | C | B |
| 101 | B | C | B |
| 102 | C | C | C |
| 103 | B | C | B |
| 104 | C | C | B |
| 105 | B | C | B |
| 106 | B | C | B |
| 107 | A | C | A |
| 108 | B | C | B |
| 109 | A | C | B |
| 110 | A | C | B |
| 111 | A | C | B |
| 112 | B | B | B |
| 113 | B | C | B |
| 114 | B | B | B |
| 115 | A | C | B |
| 116 | B | C | B |
| 117 | B | C | B |

In Vivo Assay

Evaluation of Pharmacological Efficacy of a Compound of the Invention in a Model of Diet-Induced Obesity (DIO) in Mice The DIO model in mice exhibits several features that are hallmark of metabolic syndrome in humans. Metabolic syndrome in humans is characterized by abdominal obesity, high triglycerides, impaired fasting glucose and hyperinsulinemia. In the DIO model, mice are fed high fat diet (HFD, Research diet D12492, Research Diet, NJ) diet (58% lard) for the entire period of the study. Compared to normal chow (NC, Harlan-Tekland #8604, WI) fed animals the HF fed mice develop several features of metabolic syndrome such as, hypertriglyceridemia, hyperinsulinemia and mild hyperglycemia, as early as two weeks, on this diet. Body mass analyses demonstrate that the mice also develop a striking increase in visceral obesity by weeks 3-4 of HF feeding. This model was used to evaluate the pharmacological effects of a compound of the invention selected from the group consisting of Examples 1-117 (referred to for the purposes of this study as "Compound (I)") in mitigating several features of HFD induced metabolic syndrome in rodents.

C57Bl/6j mice (n=5) were fed ad libitum with either the HFD (58% fat) or NC (5%) diet for 3 weeks prior to start of experiment, and throughout the course of the experiment (45 days). Starting on Day 1, mice were dosed BID with either Compound (I)+vehicle, vehicle alone, or GW501516, a known PPARδ modulator in clinical development by Glaxo-Wellcome, for the entire period of the study. Animals were the assessed for body weight gain, food intake, triglyceride (TG), insulin, and glucose levels under fasting and postprandial (PP) conditions. Animals were weighed twice weekly in the morning to determine body weight gain. Plasma or serum was separated from whole blood (Sarstedt) and TG levels were assayed with a TG kit (Thermo Electron Corporation, TX). Plasma insulin levels were assayed using the ultrasensitive mouse Insulin ELISA immunoassay (American Laboratory Products Company). Total cholesterol, HDLc and LDLc was measured to evaluate pharmacological efficacy at various time points during the study and serum transaminases were measured to evaluate any potential toxicity of the compound. These measurements were performed with a chemistry analyzer at Labcorp of America, NC. The pharmacological efficacy of the compound in the dose ranging study is summarized in Table 2:

TABLE 2

| Group | Diet | Dose, mg/kg | Compound or Vehicle | % change in body weight (d0 vs d40) | TG (mg/dl) | Insulin (ng/ml) |
|---|---|---|---|---|---|---|
| 1 | NC | — | Vehicle | 13.1 | 156 ± 33 | 0.6 ± 0.2 |
| 2 | NC | 4.5 | Compound (I) | 7.6 | 129 ± 17 | 0.3 ± 0.1 |
| 3 | HFD | — | Vehicle | 30.2 | 301 ± 40 | 1.4 ± 0.4 |
| 4 | HFD | 1.5 | Compound (I) | 13.8 | 264 ± 25 | 1.4 ± 0.2 |
| 5 | HFD | 3.0 | Compound (I) | 9.7 | 177 ± 33 | 0.9 ± 0.3 |
| 6 | HFD | 4.5 | Compound (I) | 10.1 | 175 ± 48 | 1 ± 0.2 |
| 7 | HFD | 1.5 | GW516 | 10.6 | 268 ± 56 | 1.3 ± 0.3 |

Compound (I) lowered hepatic glucose output in a glucose tolerance test (IPGTT) performed using a bolus of glucose (2 mg/kg) in mice fasted overnight and demonstrated improved insulin sensitivity over the HFD vehicle group in insulin tolerance testing (IPITT) conducted with insulin at 1 U/Kg. The compound had no effect on fasted or PP glucose levels but showed significant reduction in body weight gain, visceral obesity, triglyceride and insulin levels induced by the HFD. In addition we observed a significant reversal of HFD-induced insulin resistance in the mice treated with the compound.

From the foregoing description, one skilled in the art can easily ascertain the essential characteristics of this invention, and without departing from the spirit and scope thereof, can make various changes and modifications of the invention to adapt it to various usages and conditions.

We claim:

1. 4-[2,6-Dimethyl-4-(4-trifluoromethoxy-phenyl)-piperazine-1-sulfonyl]-indan-2-carboxylic acid.

2. 4-[cis-2,6-Dimethyl-4-(4-trifluoromethoxy-phenyl)-piperazine-1-sulfonyl]-indan-2-carboxylic acid.

3. A single enantiomer of 4-[cis-2,6-dimethyl-4-(4-trifluoromethoxy-phenyl)-piperazine-1-sulfonyl]-indan-2-carboxylic acid substantially free of the other enantiomer.

4. A pharmaceutically acceptable salt of 4-[cis-2,6-dimethyl-4-(4-trifluoromethoxy-phenyl)-piperazine-1-sulfonyl]-indan-2-carboxylic acid.

5. A pharmaceutical composition comprising:
At least one compound having the formula of

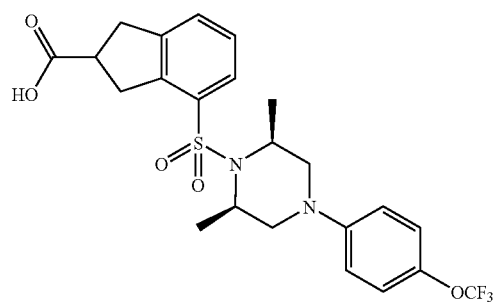

or a salt thereof; and
together with a pharmaceutically acceptable carrier.

6. A pharmaceutical composition comprising a compound as recited in claim 1 together with a pharmaceutically acceptable carrier.

7. A pharmaceutical composition comprising a compound as recited in claim 2 together with a pharmaceutically acceptable carrier.

8. A pharmaceutical composition comprising a compound as recited in claim 3 together with a pharmaceutically acceptable carrier.

9. A pharmaceutical composition comprising a compound as recited in claim 4 together with a pharmaceutically acceptable carrier.

* * * * *